(12) United States Patent
Li et al.

(10) Patent No.: US 11,045,553 B2
(45) Date of Patent: Jun. 29, 2021

(54) METHOD FOR PREPARING STABILIZED METAL ION LIGAND NANOCOMPLEX AND COMPOSITIONS THEREOF

(71) Applicant: AUBURN UNIVERSITY, Auburn, AL (US)

(72) Inventors: Feng Li, Auburn, AL (US); Wu Chen, Auburn, AL (US); Pengyu Chen, Auburn, AL (US)

(73) Assignee: AUBURN UNIVERSITY, Auburn, AL (US)

(*) Notice: Subject to any disclaimer, the term of this patent is extended or adjusted under 35 U.S.C. 154(b) by 29 days.

(21) Appl. No.: 16/222,500

(22) Filed: Dec. 17, 2018

(65) Prior Publication Data
US 2020/0230245 A1  Jul. 23, 2020

Related U.S. Application Data

(60) Provisional application No. 62/607,086, filed on Dec. 18, 2017.

(51) Int. Cl.
| | |
|---|---|
| C07F 1/08 | (2006.01) |
| A61K 47/52 | (2017.01) |
| A61K 47/69 | (2017.01) |
| A61K 31/325 | (2006.01) |
| A61K 31/337 | (2006.01) |
| A61K 31/704 | (2006.01) |
| A61K 49/18 | (2006.01) |
| A61K 33/24 | (2019.01) |
| A61K 33/242 | (2019.01) |

(Continued)

(52) U.S. Cl.
CPC ............ *A61K 47/52* (2017.08); *A61K 31/325* (2013.01); *A61K 31/337* (2013.01); *A61K 31/704* (2013.01); *A61K 33/24* (2013.01); *A61K 33/242* (2019.01); *A61K 33/243* (2019.01); *A61K 33/244* (2019.01); *A61K 47/6923* (2017.08); *A61K 49/1824* (2013.01); *C07F 1/08* (2013.01)

(58) Field of Classification Search
CPC ....................................................... A61K 33/24
See application file for complete search history.

(56) References Cited

U.S. PATENT DOCUMENTS

| | | | | |
|---|---|---|---|---|
| 2015/0273060 | A1* | 10/2015 | Zasadzinski | A61K 9/1271 604/20 |
| 2016/0166706 | A1* | 6/2016 | Xu | A61K 47/60 424/78.17 |
| 2016/0271271 | A1* | 9/2016 | Molokanova | A61P 21/00 |

FOREIGN PATENT DOCUMENTS

| | | | | |
|---|---|---|---|---|
| CN | 103222961 A | | 7/2013 | |
| WO | WO-2009117333 A1 | * | 9/2009 | ............ A61K 31/27 |

(Continued)

OTHER PUBLICATIONS

Rosales et al. Angew Chem Int. Ed., 50, 5509-5513 (Year: 2011).*

(Continued)

*Primary Examiner* — Mark S Kaucher
(74) *Attorney, Agent, or Firm* — Barnes & Thornburg LLP

(57) ABSTRACT

The present disclosure provides method of making a nanoparticle complex wherein the nanoparticle complex comprises a ligand and a metal cation. The disclosure also provides nanoparticle complexes, methods of treating a disease in a patient utilizing the nanoparticle complexes, methods of identifying a disease in a patient utilizing the nanoparticle complexes, and kits involving the nanoparticle complexes.

18 Claims, 48 Drawing Sheets

(51) Int. Cl.
*A61K 33/244* (2019.01)
*A61K 33/243* (2019.01)

(56) References Cited

FOREIGN PATENT DOCUMENTS

| WO | 2017077336 A1 | 5/2017 | |
|---|---|---|---|
| WO | WO-2017100925 A1 * | 6/2017 | ........... A61K 9/0019 |
| WO | 2018100560 A1 | 6/2018 | |
| WO | 2018100561 A1 | 6/2018 | |

OTHER PUBLICATIONS

Suzuki et al. Biochmica et Biophysica Acta, 1335, 3, 242-245 (Year: 1997).*

Charlier et al. Magnetic Resonance in Medicine, 55, 11, 215-218 (Year: 2005).*
PCT Search Report and Written Opinion prepared for PCT/US2018/066037, completed Mar. 27, 2019.
Berry et al., "Dithiocarbamate complexes as radiopharmaceuticals for medical imaging," Mini Rev Med Chem., Oct. 2012, vol. 12, Issue: 12, pp. 1174-1183.
Chen et al., "Disulfiram Copper Nanoparticles Prepared with a Stabilized Metal Ion Ligand Complex Method for Treating Drug-Resistant Prostate Cancers." ACS Applied Materials & Interfaces, 2018, vol. 10, pp. 41118-41128.
You et al., "Antitumor activity of PEG—PCL/dithiocarbamate-copper nanoparticles," ChinaNanomedicine Abstracts/Nanomedicine: Nanotechnology, Biology, and Medicine, 2016, vol. 12, pp. 449-575.
Shao et al., "Copper-enhanced cytotoxicity of PEG—PDTC nanomedicines," ChinaNanomedicine Abstracts/Nanomedicine: Nanotechnology, Biology, and Medicine, 2016, vol. 12, pp. 470-471.

* cited by examiner

| Sample | size (nm) | PDI |
|---|---|---|
| DSPE-PEG | 16 | 0.781 |
| DSPE-PEG+ Cu(DDC)2 | 38 | 0.191 |
| BSA | 5 | 0.301 |
| BSA+Cu(DDC)2 | 65 | 0.19 |
| TPGS | 12 | 0.056 |
| TPGS+Cu(DDC)2 | 47 | 0.203 |
| F127 | 9.5 | 0.295 |
| F127+Cu(DDC)2 | 79 | 0.407 |

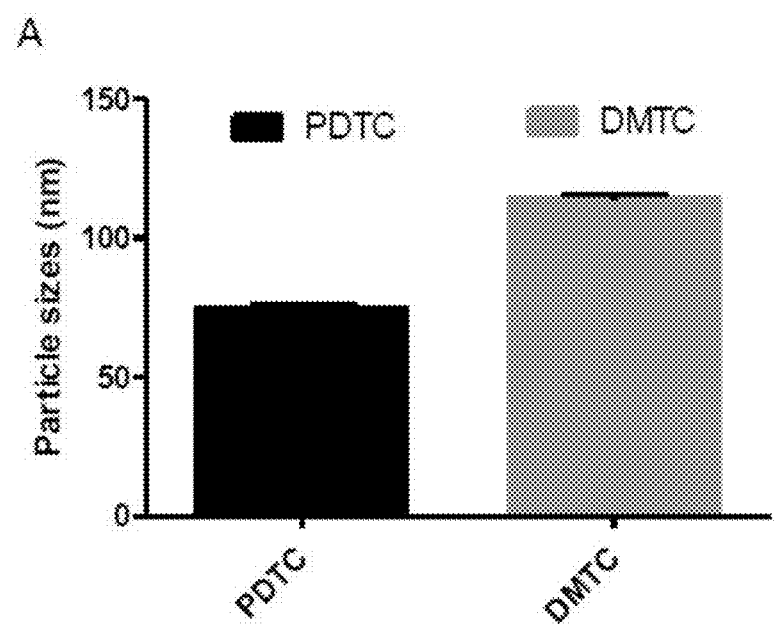
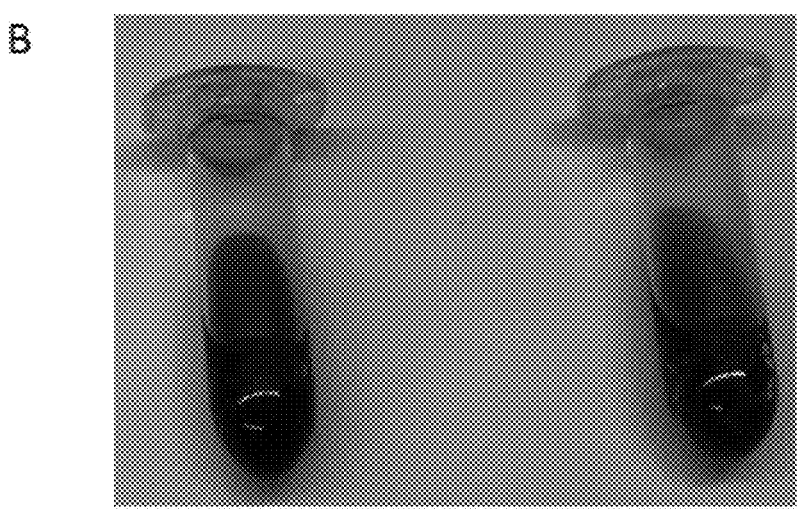
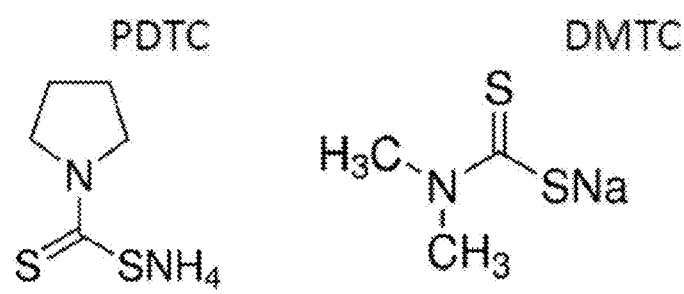
FIGURE 30A-30B

A

B

METHOD FOR PREPARING STABILIZED METAL ION LIGAND NANOCOMPLEX AND COMPOSITIONS THEREOF

CROSS-REFERENCE TO RELATED APPLICATIONS

This application claims the benefit under 35 USC § 119(e) of U.S. Provisional Application Ser. No. 62/607,086, filed on Dec. 18, 2017, the entire disclosure of which is incorporated herein by reference.

TECHNICAL FIELD

The invention relates to method of making nanoparticle complexes and the nanoparticle complexes themselves. The invention also includes methods utilizing the nanoparticle complexes for the treatment of disease or for identifying a disease in a patient, as well as kits for the nanoparticle complexes.

BACKGROUND AND SUMMARY OF THE INVENTION

Disulfiram (DSF) is a therapeutic agent most widely known for its efficacy as an alcohol-aversion drug. In recent years, DSF has also been explored as a cancer treatment. A complex formed by DSF and copper ions has been evaluated for anticancer activity. DSF/Cu has been shown to inhibit the proteasome/poly-Ub protein degradation pathway by targeting the nuclear protein localization 4 (NPL4) protein and could also inhibit cancer stem cells, as well as sensitize resistant cancer to chemotherapy drugs by inhibiting P-gp.

The anticancer activity of DSF/Cu is greatly dependent on the formation of the active metabolite, copper diethyldithiocarbamate ($Cu(DDC)_2$). Due to the poor in vivo stability and rapid degradation of DSF, the co-administration of DSF and copper to patients yields extremely low in vivo concentrations of $Cu(DDC)_2$ which significantly compromises the anticancer efficacy and results in poor clinical outcomes.

The direct administration of Cu(DDC)2 is a promising alternative for Cu/DSF combination therapy. However, efficient drug delivery remains a significant challenge for $Cu(DDC)_2$ and, thus far, has hindered its clinical use. Due to the low water solubility of $Cu(DDC)_2$, there is a great need to develop a new formulations designed to increase $Cu(DDC)_2$ solubility to provide acceptability for clinical use. Accordingly, the present disclosure provides nanoparticle complexes and methods of using the nanoparticle complexes, which exhibit desirable properties and provide related advantages for improvement in administration and treatment of animals with the complexes, for example $Cu(DDC)_2$ nanoparticle complexes. The present disclosure provides method of making a nanoparticle complex wherein the nanoparticle complex comprises a ligand and a metal cation. The disclosure also provides nanoparticle complexes, methods of treating a disease in a patient utilizing the nanoparticle complexes, methods of identifying a disease in a patient utilizing the nanoparticle complexes, and kits involving the nanoparticle complexes.

The nanoparticle complexes and aspects thereof according to the present disclosure provide several advantages compared to other compositions and methods known in the art. First, the method for making the nanoparticle complexes is easier than the complex mechanisms currently known in the art and is adaptable to a straightforward scale-up process. Second, the costs associated with the nanoparticle complexes and the methods of making the nanoparticle complexes is much lower than comparative compositions and methods.

Third, the nanoparticle complexes and associated aspects can utilize many different ligands, metal cations, and stabilizers. For example, various therapeutic agents and imaging agents can serve as ligands for the instant disclosure, several different metal cations are envisioned, and many safe, FDA-approved stabilizers can be included in the nanoparticle complexes. Use of stabilizers with the nanoparticle complexes of the present disclosure can provide improved stability of the complexes and prevent aggregation.

Fourth, the nanoparticle complexes of the present disclosure have properties that are advantageous compared to those known in the art. For instance, the nanoparticle complexes can be formulated at a particle size that allows for outstanding stability, low aggregation, and long-term storage properties. Further, the nanoparticle complexes provide excellent drug loading efficiencies and high drug concentrations. Moreover, the nanoparticle complexes offer enhanced efficacy and reduced toxicity to patients due to improvements in targeting and potency of the complexes. Finally, the nanoparticle complexes are able to be formulated without the use of dimethyl sulfoxide (DMSO), which is known to be toxic in certain instances.

The following numbered embodiments are contemplated and are non-limiting:

1. A method of making a nanoparticle complex, said method comprising the steps of:
   providing a first composition, wherein the first composition comprises at least one ligand;
   providing a second composition, wherein the second composition comprises a salt of the formula $M_nX_y$, wherein M is a metal cation and X is counterion, and wherein n is an integer from 1 to 3 and y is an integer from 1 to 5; and
   combining the first composition and the second composition to obtain the nanoparticle complex, wherein the nanoparticle complex comprises the ligand and M.
2. The method of clause 1, wherein the nanoparticle complex comprises a core of the first composition and the second composition.
3. The method of clause 1 or clause 2, wherein the first composition is a solution.
4. The method of any of clauses 1 to 3, wherein the ligand is an organic molecule is capable of forming a complex with the metal cation.
5. The method of clause 4, wherein the ligand and the metal cation are capable of forming a precipitation in solution without addition of a stabilizer.
6. The method of clause 4 or clause 5, wherein the organic molecule and the metal cation interact via a covalent interaction.
7. The method of clause 6, wherein the covalent interaction is an ionic bond.
8. The method of clause 6, wherein the covalent interaction is a coordinate bond.
9. The method of clause 4 or clause 5, wherein the organic molecule and the metal cation interact via a non-covalent interaction.
10. The method of clause 9, wherein the non-covalent interaction is a van der Waals force.
11. The method of clause 9, wherein the non-covalent interaction is a hydrogen bond.
12. The method of clause 9, wherein the non-covalent interaction is a hydrophobic interaction.

13. The method of clause 9, wherein the non-covalent interaction is an electrostatic interaction.
14. The method of clause 4 or clause 5, wherein the organic molecule comprises an atom or a functional group capable of donating an electron pair to the metal cation.
15. The method of clause 14, wherein the atom or the functional group is selected from the group consisting of S-donor, O-donor, N,O-donor, N-donor, P-donor, Lewis base, Shiff base, macrocycle, and N—N dimine donor.
16. The method of any of clauses 1 to 15, wherein the ligand is a therapeutic agent.
17. The method of clause 16, wherein the therapeutic agent is diethyldithiocarbamatetrihydrate (DDC).
18. The method of clause 16, wherein the therapeutic agent is 1-pyrrolidinecarbodithioic acid ammonium salt (PDTC).
19. The method of clause 16, wherein the therapeutic agent is sodium dimethyldithiocarbamate dihydrate (DMTC).
20. The method of clause 16, wherein the therapeutic agent is a dithiocarbamate derivative of the formula $(R_1R_2—N—C(S)S^-)X^+$.
21. The method of clause 20, wherein the X is NH4+, Li+, H+, Na+, K+.
22. The method of clause 20, wherein $R_1$ comprises an alkyl group or an ethyl group.
23. The method of clause 20, wherein $R_2$ comprises an alkyl group or an ethyl group.
24. The method of clause 20, wherein $R_1$ is —CH$_2$CH$_3$.
25. The method of clause 20, wherein $R_1$ is —CH$_3$.
26. The method of clause 20, wherein $R_2$ is —CH$_2$CH$_3$.
27. The method of clause 20, wherein $R_2$ is —CH$_3$.
28. The method of clause 20, wherein $R_1$ is pyrrolidine.
29. The method of clause 20, wherein $R_2$ is pyrrolidine.
30. The method of clause 16, wherein the therapeutic agent is a derivative of a compound selected from the group consisting of selenothiocarbamate, diselenocarbamate, thiocarbamate, carbamate, phosphino-dithioformate, dithiophosphate, xanthate, thioxanthate, and dithiocarboxylate.
31. The method of clause 16, wherein the therapeutic agent is selected from the group consisting of disulfiram, sodium diethyldithiocarbamatetrihydrate, pyrrolidinecarbodithioic acid ammonium salt, sodium dimethyldithiocarbamate dehydrate, 2-(Di-2-pyridinylmethylene)hydrazinecarbodithioic acid or its salt, pamidronate dithiocarbamate or its salt, finasteride dithiocarbamate or its salt, clioquinol, 2-(Di-2-pyridinylmethylene)hydrazinecarbodithioic acid or its salt, pyrithione, plumbagin, 8-hydroxyquinoline, 1,10-phenanthroline(PHEN), 2,2'-bipyridine, 2-hydroxy-1-naphthaldehyde-L-ornithine, 2,4-dihydroxybenzaldehyde-L-ornithine, quinoline-2-carboxaldehyde, taurine salicylic Schiff-base, L-methionine-o-vanillin Schiff base, valine-2-hydroxy-1-naphthaldehyde Schiff base, 2,4-diiodo-6-((pyridine-2-ylmethylamino) methyl)phenol, 3-indole acetic acid, 3-indole propionic acid, tri(hydroxymethyl)phosphine, methylated glycine, DL-alanine, 2,2-dimethyglycine, 4-amino-1,4-dihidro-3-(2-pyridyl)-5-thioxo-1,2,4-triazole, 3-aminopyridine-2-carboxaldehyde thiosemicarbazone, di-2-pyridylketone thiosemicarbazones, di-2-pyridylketone thiosemicarbazones, Piperazine-1,4-bisdithiocarbamate, 2-hydroxylethyl (isopropyl) dithiocarbamte, benzyl(methyl) dithiocarbamate, PBT2, glyoxal-bis(thiosemicarbazone), glyoxal bis(4-methylthiosemicarbazonato), diacetyl-bis(4-methylthiosemicarbazonato), elesclomol, pyrithione, metformin, aspirin, and doxorubicin.
32. The method of clause 16, wherein the therapeutic agent is selected from the group consisting of paclitaxel, docetaxel, and doxorubicin.
33. The method of any of clauses 1 to 15, wherein the ligand is an imaging agent.
34. The method of clause 33, wherein the imaging agent is selected from the group consisting of dicyanomethylene-4H-pyran, IR820, merocyanine, ICG, NaYF$_4$, ZW800-1Cy5.5, Cy5.5, Cy7, IRDye680, IRDye800, Alexa Fluor 750, Cyanine-type, IRDye800CW, gold nanoclusters, and poly(benzo[1,2-b:3,4-b']difuran-alt-fluorothieno-[3,4-b]thiophene).
35. The method of clause 33, wherein the imaging agent is an infrared dye.
36. The method of clause 33, wherein the imaging agent is a metallic dye.
37. The method of clause 33, wherein the imaging agent is a MRI contrast agent.
38. The method of any of clauses 1 to 15, wherein the ligand is a photosensitizer.
39. The method of clause 38, wherein the photosensitizer is selected from the group consisting of porfimer sodium, 5-aminolevulinic acid (ALA), methyl aminolevulinate (MAL), hexaminolevulinate (HAL), benzoporphyrin derivative monoacid ring A (BPD-MA), meta-tetra(hydroxyphenyl) chlorin (m-THPC), tin ethyl etiopurpurin, N-aspartyl chlorin e6 (NPe6), 2-(1-Hexyloxyethyl)-2-devinylpyropheophorbide (HPPH), palladium bacteriopheophorbide (WST09), WST11, motexafin lutetium (Lu-Tex), aluminum phthalocyanine tetrasulfonate (AlPcS4), and silicon phthalocyanine (Pc4).
40. The method of any of clauses 1 to 39, wherein the first composition comprises two ligands.
41. The method of clause 40, wherein the first ligand is a therapeutic agent and the second ligand is an imaging agent.
42. The method of clause 41, wherein the first ligand is a first therapeutic agent and the second ligand is a second therapeutic agent.
43. The method of clause 42, wherein the second therapeutic agent is selected from the group consisting of nucleic acids, DNA, RNA, peptides, proteins, antibodies, cytokines, and small molecule chemical drugs.
44. The method of clause 42, wherein the second therapeutic agent is incorporated through the interaction with the nanoparticle complex.
45. The method of clause 42, wherein the second therapeutic agent is incorporated through the interaction with the stabilizer.
46. The method of clause 42, wherein the second therapeutic agent comprises a functional group that interacts with the nanoparticle complex.
47. The method of clause 46, wherein the functional group is introduced to the second therapeutic agent to enhance interaction with the nanoparticle complex.
48. The method of clause 46, wherein the second therapeutic agent is selected from the group consisting of an anticancer agent and an immunomodulation agent.
49. The method of any of clauses 1 to 48, wherein the second composition is a solution.
50. The method of any of clauses 1 to 49, wherein M has a 3+ charge.

51. The method of any of clauses 1 to 49, wherein M has a 2+ charge.
52. The method of any of clauses 1 to 49, wherein M has a 1+ charge.
53. The method of any of clauses 1 to 49, wherein M is a Group 4 (IV B) metal selected from the group consisting of titanium, zirconium, and hafnium.
54. The method of any of clauses 1 to 49, wherein M is a Group 5 (V B) metal selected from the group consisting of Vanadium, Niobium, and Tantalum.
55. The method of any of clauses 1 to 49, wherein M is a Group 6 (VI B) metal selected from the group consisting of Chromium, Molybdenum, and Tungsten.
56. The method of any of clauses 1 to 49, wherein M is a Group 7 metal selected from the group consisting of Manganese, Technetium, and Rhenium.
57. The method of any of clauses 1 to 49, wherein M is a Group 8 (VIIIB) metal selected from the group consisting of Iron, Ruthenium, and Osmium.
58. The method of any of clauses 1 to 49, wherein M is a Group 9 (VIIIB) metal selected from the group consisting of Cobalt, Rhodium, and Iridium.
59. The method of any of clauses 1 to 49, wherein M is a Group 10 (VIII) metal selected from the group consisting of Nickel, Palladium, and Platinum.
60. The method of any of clauses 1 to 49, wherein M is a Group 11 (I B) metal selected from the group consisting of Copper, Silver, and Gold.
61. The method of any of clauses 1 to 49, wherein M is a Group 12 (II B) metal selected from the group consisting of Zinc, Cadmium, and Mercury.
62. The method of any of clauses 1 to 49, wherein M is selected from the group consisting of titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, and mercury.
63. The method of any of clauses 1 to 49, wherein M is a radioactive metal cation.
64. The method of any of clauses 1 to 49, wherein M is selected from the group consisting of Sc-44, Ti-46, V-48, Mn-52, Co-55, Cu-64, Ga-68, and Zr-89.
65. The method of any of clauses 1 to 49, wherein X is selected from the group consisting of chloride, iodide, fluoride, bromide, nitrate, sulfate, arsenate, arsenite, hydrogen sulfate, thiosulfate, sulfite, perchlorate, chlorate, chlorite, hypochlorite, carbonate, bicarbonate, acetate, cyanide, cyanate, thiocyanate, hydroxide, phosphate, hydrogen phosphate, dihydrogen phosphate, nitrite, iodate, bromate, hypobromite, chromate, dichromate, and permanganate.
66. The method of any of clauses 1 to 49, wherein n is 1 and y is 1.
67. The method of any of clauses 1 to 49, wherein n is 1 and y is 2.
68. The method of any of clauses 1 to 49, wherein n is 1 and y is 3.
69. The method of any of clauses 1 to 49, wherein n is 2 and y is 1.
70. The method of any of clauses 1 to 49, wherein n is 3 and y is 1.
71. The method of any of clauses 1 to 70, wherein the second composition further comprises one or more stabilizers.
72. The method of any of clauses 1 to 71, wherein the method further comprises a step of providing a third composition comprising one or more stabilizers.
73. The method of clause 72, wherein the method further comprises a step of combining the third composition with the first composition and the second composition.
74. The method of clause 73, wherein the nanoparticle complex further comprises the stabilizer.
75. The method of clause 74, wherein the stabilizer is attached to the surface of the nanoparticle complex.
76. The method of clause 74, wherein the stabilizer is attached to the core of the nanoparticle complex.
77. The method of any of clauses 72 to 76, wherein the third composition is a solution.
78. The method of any of clauses 72 to 77, wherein the third composition comprises a hydrophilic composition.
79. The method of clause 78, wherein the hydrophilic composition does not form liposomes.
80. The method of any of clauses 72 to 77, wherein the third composition comprises an amphiphilic composition.
81. The method of clause 80, wherein the amphiphilic composition does not form liposomes.
82. The method of clause 80, wherein the amphiphilic composition does not form micelles.
83. The method of any of clauses 72 to 77, wherein the stabilizer is an amphiphilic composition.
84. The method of clause 83, wherein the amphiphilic composition comprises at least one hydrophilic component and at least one hydrophobic component.
85. The method of clause 83 or clause 84, wherein the amphiphilic composition comprises an anionic surfactant.
86. The method of clause 83 or clause 84, wherein the amphiphilic composition comprises a Zwitterionic surfactant.
87. The method of clause 83 or clause 84, wherein the amphiphilic composition comprises a cationic surfactant.
88. The method of clause 83 or clause 84, wherein the amphiphilic composition comprises a non-ionic surfactant.
89. The method of clause 83 or clause 84, wherein the amphiphilic composition comprises a poly ester type surfactant.
90. The method of clause 83 or clause 84, wherein the amphiphilic composition comprises an alkanolamide type surfactant.
91. The method of clause 83 or clause 84, wherein the amphiphilic composition comprises an APG type surfactant.
92. The method of clause 83 or clause 84, wherein the amphiphilic composition comprises an alkoxylate type surfactant.
93. The method of clause 83 or clause 84, wherein the amphiphilic composition comprises a fatty acid alkyl ester surfactant.
94. The method of clause 83 or clause 84, wherein the amphiphilic composition is prepared by conjugating one or more hydrophobic materials to one or more hydrophilic materials.
95. The method of clause 94, wherein the hydrophilic material is selected from the group consisting of Poly (N-isopropylacrylamide) (PNIPAM) and Polyacrylamide (PAM), Poly(2-oxazoline) and Polyethylenimine (PEI), Poly(acrylic acid), Polymethacrylate and Other Acrylic Polymers, Poly(ethylene glycol) and Poly(ethylene oxide), Poly(vinyl alcohol) (PVA) and Copolymers, Poly(vinylpyrrolidone) (PVP) and Copolymers, Polyelectrolytes, hyaluronic acid, heparin, chondroitin sulfate, chitosan, polyglutamate, poly-lysine, poly-histidine, hydrophilic peptide, hydrophilic protein, nucleic acid, and poly-saccharide.
96. The method of clause 94, wherein the hydrophilic material has a molecular weight between about 1000 to about 1,000,000.
97. The method of clause 94, wherein the hydrophobic material comprises a drug, an imaging agent, a fatty acid, a phospholipid, a cholesterol, a cholic acid, or analogs thereof.
98. The method of clause 83 or clause 84, wherein the amphiphilic composition is a copolymer.
99. The method of clause 98, wherein the copolymer is PEG-PLA.
100. The method of clause 98, wherein the copolymer is PEG-PCL.
101. The method of clause 83 or clause 84, wherein the amphiphilic composition comprises a copolymer comprising an A-B type, an A-B-A type, or a B-A-B type.
102. The method of clause 101, wherein A is a hydrophilic block polymer selected from the group consisting of Methoxy poly(ethylene glycol), Poly[N-(2-hydroxypropyl) methacrylamide] (pHPMA), and Poly(methacrylic acid).
103. The method of clause 102, wherein the hydrophilic block polymer is a linear polymer, a branched polymer, or a dendrimer.
104. The method of any of clauses 101 to 103, wherein B is a hydrophobic block polymer selected from the group consisting of poly(lactide), poly(lactide-co-glycolide), poly(caprolactone), poly(aspartic acid), Poly(lysine), Poly(styrene), Poly(benzyl-aspartate), poly(benzyl-aspartate), poly(propylene oxide), Poly(isoprene), and Poly(carbonate ester).
105. The method of clause 104, wherein the hydrophobic block polymer is a linear polymer, a branched polymer, or a dendrimer.
106. The method of clause 83 or clause 84, wherein the amphiphilic composition is an amphiphilic peptide.
107. The method of clause 106, wherein the amphiphilic peptide is a synthetic peptide.
108. The method of clause 106, wherein the amphiphilic peptide is produced with recombinant technology from a mammalian cell.
109. The method of clause 106, wherein the amphiphilic peptide is produced with recombinant technology from a non-mammalian cell.
110. The method of clause 83 or clause 84, wherein the amphiphilic composition is an amphiphilic protein.
111. The method of clause 110, wherein the amphiphilic protein is produced with recombinant technology from a mammalian cell.
112. The method of clause 110, wherein the amphiphilic protein is produced with recombinant technology from a non-mammalian cell.
113. The method of any of clauses 72 to 77, wherein the stabilizer is a hydrophilic polymer.
114. The method of clause 113, wherein the hydrophilic polymer is a polymer comprising a sulfate group.
115. The method of clause 114, wherein the polymer comprising a sulfate group is dextran sulfate.
116. The method of clause 114, wherein the polymer comprising a sulfate group is heparin sulfate.
117. The method of clause 114, wherein the polymer comprising a sulfate group is chondroitin sulfate.
118. The method of clause 114, wherein the polymer comprising a sulfate group is alginate sulfate.
119. The method of clause 113, wherein the hydrophilic polymer is a polymer comprising a dithiocarbamate group.
120. The method of any of clauses 71 to 119 wherein the stabilizer does not comprise PEG5000.
121. The method of any of clauses 71 to 120, wherein the stabilizer does not comprise PE2000.
122. The method of any of clauses 1 to 121, wherein the step of combining the first composition and the second composition is performed via vortexing.
123. The method of any of clauses 1 to 122, wherein the step of combining the first composition and the second composition is performed using a mixing device.
124. The method of clause 123, wherein the mixing device is a vortex device.
125. The method of clause 123, wherein the mixing device is a microfluidics mixer.
126. The method of clause 123, wherein the mixing device is a propeller mixer.
127. The method of clause 123, wherein the mixing device is a turbine mixer.
128. The method of clause 123, wherein the mixing device is a blender.
129. The method of clause 123, wherein the mixing device is a sonicator.
130. The method of clause 123, wherein the mixing device is a homogenizer.
131. The method of clause 123, wherein the mixing device is a sprayer.
132. The method of clause 123, wherein the mixing device is an eletrosprayer.
133. The method of any of clauses 72 to 132, wherein the combining of the first composition and the second composition is performed prior to the combination with the third composition.
134. The method of any of clauses 72 to 132, wherein the combining of the first composition and the second composition is performed simultaneously with the combination with the third composition.
135. The method of any of clauses 1 to 134, wherein the nanoparticle complex further comprises a targeting moiety on a surface of the nanoparticle complex.
136. The method of clause 135, wherein the targeting moiety is selected from the group consisting of small molecules, peptide, proteins, antibody, nucleic acids, and polymers.
137. The method of clause 135, wherein the targeting moiety is a tumor targeting moiety.
138. The method of clause 137, wherein the tumor targeting moiety is capable of binding to a protein or a receptor on the tumor.
139. The method of clause 137, wherein the tumor targeting moiety is capable of binding to a protein or a receptor on a microenvironment of the tumor.
140. The method of any of clause 135 to 139, wherein the targeting moiety is attached to the nanoparticle complex via a covalent bond.
141. The method of any of clause 135 to 139, wherein the targeting moiety is attached to the nanoparticle complex via a non-covalent interaction.
142. The method of any of clause 135 to 139, wherein the targeting moiety is attached to the stabilizer via a covalent bond.

143. The method of any of clause 135 to 139, wherein the targeting moiety is attached to the stabilizer via a non-covalent interaction.
144. The method of any of clauses 1 to 143, wherein the nanoparticle complex further comprises a second therapeutic agent.
145. The method of clause 144, wherein the second therapeutic agent is selected from the group consisting of nucleic acids, DNA, RNA, peptides, proteins, antibodies, cytokines, and small molecule chemical drugs.
146. The method of clause 144 or clause 145, wherein the second therapeutic agent is incorporated through the interaction with the nanoparticle complex.
147. The method of clause 144 or clause 145, wherein the second therapeutic agent is incorporated through the interaction with the stabilizer.
148. The method of clause 144 or clause 145, wherein the second therapeutic agent comprises a functional group that interacts with the nanoparticle complex.
149. The method of clause 148, wherein the functional group is introduced to the second therapeutic agent to enhance interaction with the nanoparticle complex.
150. The method of any of clauses 144 to 149, wherein the second therapeutic agent is selected from the group consisting of an anticancer agent and an immunomodulation agent.
151. The method of any of clauses 1 to 150 wherein the nanoparticle complex has a particle size between about 10 nm to about 250 nm.
152. The method of clause 151, wherein the nanoparticle complex has a particle size between about 25 nm to about 100 nm.
153. The method of clause 151, wherein the nanoparticle complex has a particle size between about 25 nm to about 50 nm.
154. The method of clause 151, wherein the nanoparticle complex has a particle size between about 50 nm to about 100 nm.
155. The method of any of clauses 1 to 154, wherein the nanoparticle complex has a concentration between about 0.1 mg/ml and about 200 mg/ml.
156. The method of clause 155, wherein the nanoparticle complex has a concentration of the ligand between about 1 mg/ml and about 5 mg/ml.
157. The method of clause 155, wherein the nanoparticle complex has a concentration of the ligand between about 2 mg/ml and about 4 mg/ml.
158. The method of clause 155, wherein the nanoparticle complex has a concentration of the ligand of about 2 mg/ml.
159. The method of clause 155, wherein the nanoparticle complex has a concentration of the ligand of about 4 mg/ml.
160. The method of clause 155, wherein the nanoparticle complex has a concentration of the ligand between about 10 mg/ml and about 150 mg/ml.
161. The method of clause 155, wherein the nanoparticle complex has a concentration of the ligand between about 10 mg/ml and about 50 mg/ml.
162. The method of clause 155, wherein the nanoparticle complex has a concentration of the ligand between about 50 mg/ml and about 100 mg/ml.
163. The method of clause 155, wherein the nanoparticle complex has a concentration of the ligand between about 100 mg/ml and about 150 mg/ml.
164. The method of any of clauses 1 to 163, wherein the method further comprises a step of removing one or more of aggregates and particles from the combination of the first composition and the second composition.
165. The method of clause 164, wherein the step of removing one or more of aggregates and particles is performed via filtration.
166. The method of clause 164, wherein the step of removing one or more of aggregates and particles is performed via centrifugation.
167. The method of any of clauses 1 to 166, wherein the method further comprises a step of removing one or more of aggregates and particles from the combination of the first composition, the second composition, and the third composition.
168. The method of clause 167, wherein the step of removing one or more of aggregates and particles is performed via filtration.
169. The method of clause 167, wherein the step of removing one or more of aggregates and particles is performed via centrifugation.
170. The method of any of clauses 1 to 169 wherein the method further comprises a step of lyophilizing the nanoparticle complex.
171. The method of any of clauses 1 to 170 wherein dimethyl sulfoxide (DMSO) is not used for making the nanoparticle complex.
172. A nanoparticle complex comprising at least one ligand and a metal cation, wherein the nanoparticle complex is formed from the method of clause 1.
173. The nanoparticle complex of clause 172, wherein the nanoparticle complex is the nanoparticle complex of any one of clauses 1 to 171.
174. A method of treating a disease in a patient in need thereof, said method comprising the step of administering a therapeutically effective amount of a nanoparticle complex to the patient; wherein the nanoparticle complex comprises at least one ligand and a metal cation.
175. The method of clause 174, wherein the disease is cancer.
176. The method of clause 175, wherein the cancer is selected from a bone cancer, a muscle cancer, a brain cancer, a nervous system cancer, a breast cancer, a prostate cancer, an endocrine system cancer, an eye cancer, a gastrointestinal cancer, a genitourinary cancer, a gynecologic cancer, a head and neck cancer, a hematopoetic cancer, a skin cancer, a thoracic and respiratory cancer, an HIV/AIDS-related cancer, or an unsorted cancer.
177. The method of clause 175, wherein the cancer is breast cancer.
178. The method of clause 175, wherein the cancer is prostate cancer.
179. The method of any one of clauses 175 to 178, wherein the cancer is a relapsed cancer.
180. The method of any one of clauses 175 to 178, wherein the cancer is a metastatic cancer.
181. The method of any one of clauses 175 to 180, wherein the cancer is resistant or non-responsive to chemotherapy, hormone therapy, radiotherapy, or immunotherapy.
182. The method of clause 174, wherein the disease is an infectious disease.
183. The method of clause 182, wherein the infectious disease is a bacterial infection.
184. The method of clause 182, wherein the infectious disease is a viral infection.

185. The method of clause 182, wherein the infectious disease is a fungal infection.
186. The method of any one of clauses 174 to 185, wherein the method further comprises administration of a second therapeutic agent.
187. The method of any one of clauses 174 to 186, wherein the administration to the patient is a parenteral administration.
188. The method of clause 187, wherein the parenteral administration is an intravenous administration.
189. The method of clause 187, wherein the parenteral administration is an intramuscular administration.
190. The method of clause 187, wherein the parenteral administration is a subcutaneous administration.
191. The method of clause 187, wherein the parenteral administration is an intradermal administration.
192. The method of clause 187, wherein the parenteral administration is an intratumor administration.
193. The method of any one of clauses 174 to 186, wherein the administration to the patient is a transdermal administration.
194. The method of any one of clauses 174 to 186, wherein the administration to the patient is an oral administration.
195. The method of any one of clauses 174 to 186, wherein the administration to the patient is an inhalation administration.
196. The method of any one of clauses 174 to 186, wherein the administration to the patient is a local administration.
197. The method of any one of clauses 174 to 186, wherein the nanoparticle complex is the nanoparticle complex of any one of clauses 1 to 171.
198. A method of identifying a disease in a patient, said method comprising the step of administering a nanoparticle complex to the patient;
wherein the nanoparticle complex comprises at least one ligand and a metal cation.
199. The method of clause 198, wherein the disease is cancer.
200. The method of clause 199, wherein the cancer is selected from a bone cancer, a muscle cancer, a brain cancer, a nervous system cancer, a breast cancer, a prostate cancer, an endocrine system cancer, an eye cancer, a gastrointestinal cancer, a genitourinary cancer, a gynecologic cancer, a head and neck cancer, a hematopoetic cancer, a skin cancer, a thoracic and respiratory cancer, an HIV/AIDS-related cancer, or an unsorted cancer.
201. The method of clause 199, wherein the cancer is breast cancer.
202. The method of clause 199, wherein the cancer is prostate cancer.
203. The method of any of clauses 199 to 202, wherein the cancer is a relapsed cancer.
204. The method of any of clauses 199 to 202, wherein the cancer is a metastatic cancer.
205. The method of any of clauses 199 to 202, wherein the cancer is resistant or non-responsive to chemotherapy, hormone therapy, radiotherapy, or immunotherapy 206. The method of clause 198, wherein the disease is an infectious disease.
207. The method of clause 206, wherein the infectious disease is a bacterial infection.
208. The method of clause 206, wherein the infectious disease is a viral infection.
209. The method of clause 206, wherein the infectious disease is a fungal infection.
210. The method of any of clauses 198 to 209, wherein the administration to the patient is a parenteral administration.
211. The method of clause 210, wherein the parenteral administration is an intravenous administration.
212. The method of clause 210, wherein the parenteral administration is an intramuscular administration.
213. The method of clause 210, wherein the parenteral administration is a subcutaneous administration.
214. The method of clause 210, wherein the parenteral administration is an intradermal administration.
215. The method of clause 210, wherein the parenteral administration is an intratumor administration.
216. The method of any of clauses 198 to 209, wherein the administration to the patient is a transdermal administration.
217. The method of any of clauses 198 to 209, wherein the administration to the patient is an oral administration.
218. The method of any of clauses 198 to 209, wherein the administration to the patient is an inhalation administration.
219. The method of any of clauses 198 to 209, wherein the administration to the patient is a local administration.
220. The method of any of clauses 198 to 219, wherein the nanoparticle complex is accumulated specifically in a disease organ or tissue.
221. The method of clause 220, wherein the accumulated nanoparticle complex is capable of visualizing a tumor for image-guided surgery on the patient.
222. The method of any of clauses 198 to 221, wherein the nanoparticle complex comprises a probe or contrast agent to facilitate the visualization of disease site and monitor disease progression.
223. The method of any of clauses 198 to 222, wherein the nanoparticle complex is formed from the method of any of clauses 1 to 171.
224. The method of any of clauses 198 to 222, wherein the nanoparticle complex is the nanoparticle complex of any one of clauses 1 to 171.
225. A kit comprising a first composition, a second composition, and instructions for combining the first composition and the second composition;
wherein the first composition comprises at least one ligand, and
wherein the second composition comprises a salt of the formula $M_nX_y$,
wherein M is a metal cation and X is counterion, and wherein n is an integer from 1 to 3 and y is an integer from 1 to 5.
226. The kit of clause 225, wherein the kit further comprises a third composition comprising one or more stabilizers.
227. The kit of clause 225 or clause 226, wherein the kit further comprises a mixing device.
228. The kit of any one of clauses 225 to 228, wherein the kit forms a nanoparticle complex of any one of clauses 1 to 171.

BRIEF DESCRIPTION OF THE DRAWINGS

FIGS. 30A-30B show nanoparticle complexes prepared according to the disclosed methods using copper metal ions and various ligands including 1-Pyrrolidinecarbodithioic acid ammonium salt (PDTC) and Sodium Dimethyldithiocarbamate Dihydrate (DMTC), using Pluronic® F-127 (1%) as a stabilizer. (A) shows particle size; (B) shows exemplary photos.

Figure 1:
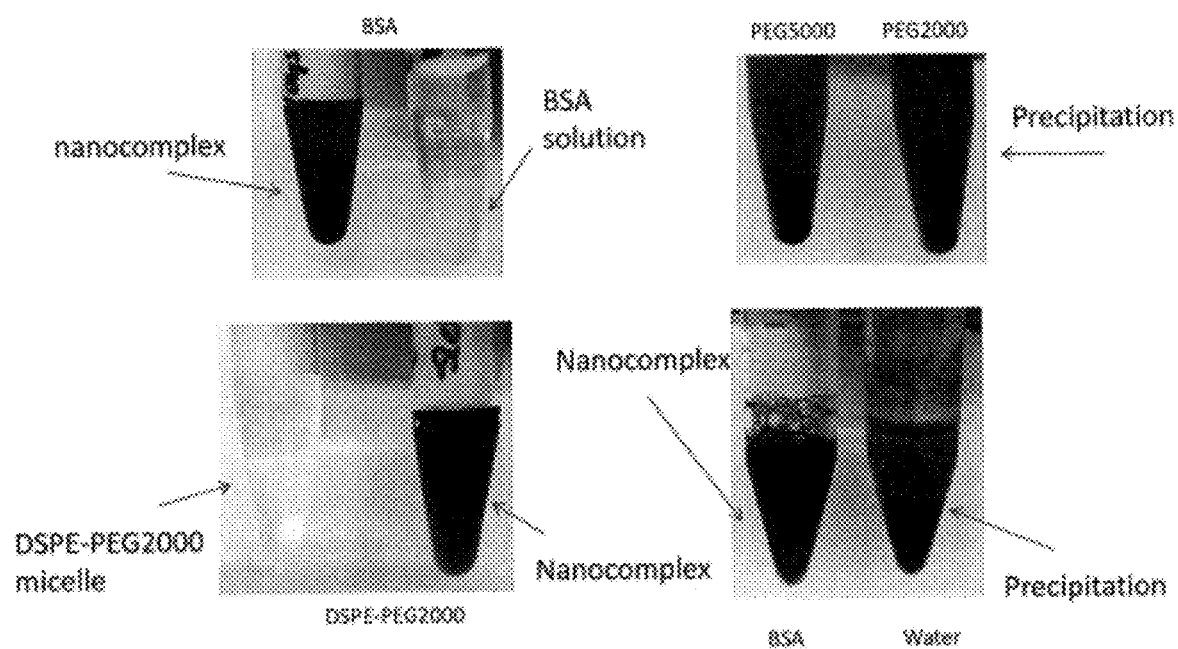
FIG. 1 shows the formation of $Cu(DDC)_2$ nanoparticle complexes with a stabilizer. A stable nanoparticle complex was formed in the presence of stabilizers (e.g., BSA, DSPE- PEG2000, etc.) Precipitation forms in the absence of a stabilizer, and results suggest that PEG2000 and PEG5000 are less desirable stabilizers.

Various embodiments of the invention are described herein as follows. In one embodiment described herein, a method of making a nanoparticle complex is provided. The method comprises the steps of providing a first composition, wherein the first composition comprises at least one ligand; providing a second composition, wherein the second composition comprises a salt of the formula MnXy, wherein M is a metal cation and X is counterion, and wherein n is an integer from 1 to 3 and y is an integer from 1 to 5; and combining the first composition and the second composition to obtain the nanoparticle complex, wherein the nanoparticle complex comprises the ligand and M. In some embodiments, a nanoparticle complex comprising at least one ligand and a metal cation is provided. In certain embodiments, the nanoparticle complex comprising at least one ligand and a metal cation is formed from the method of making.

In another embodiment, a method of treating a disease in a patient in need thereof is provided. The method comprises the step of administering a therapeutically effective amount of a nanoparticle complex to the patient, wherein the nanoparticle complex comprises at least one ligand and a metal cation.

In another embodiment, a method of identifying a disease in a patient is provided. The method comprises the step of administering a therapeutically effective amount of a nanoparticle complex to the patient, wherein the nanoparticle complex comprises at least one ligand and a metal cation.

In another embodiment, a kit is provided. The kit comprises a first composition, a second composition, and instructions for combining the first composition and the second composition, wherein the first composition comprises at least one ligand, and wherein the second composition comprises a salt of the formula MnXy, wherein M is a metal cation and X is counterion, and wherein n is an integer from 1 to 3 and y is an integer from 1 to 5.

In illustrative embodiments, a method of making a nanoparticle complex is provided. The term "nanoparticle" refers to a particle having a size measured on the nanometer scale. As used herein, the "nanoparticle" refers to a particle having a structure with a size of less than about 1,000 nanometers. As used herein, the term "nanoparticle complex" refers to a combination of the ligand and M that is a nanoparticle.

The first composition comprises at least one ligand. As used herein, the term "ligand" refers to an organic molecule that can be used to formulate the nanoparticle complex. For example, a ligand can include therapeutic agents, imaging agents, photosynthesizers, and the like.

The second composition comprises a salt of the formula $M_nX_y$, wherein M is a metal cation and X is counterion, wherein n is an integer from 1 to 3 and y is an integer from 1 to 5. The method of making a nanoparticle complex comprises the step of combining the first composition and the second composition to obtain the nanoparticle complex, wherein the nanoparticle complex comprises the ligand and M.

In some embodiments, the nanoparticle complex comprises a core of the first composition and the second composition. In these embodiments, the first composition and the second composition are included in the interior ("core") of the nanoparticle complex. In certain embodiments, the first composition is a solution. In various aspects, the second composition is a solution.

In various embodiments, the ligand is an organic molecule is capable of forming a complex with the metal cation. In certain embodiments, the ligand and the metal cation are capable for forming a precipitation in solution without addition of a stabilizer.

In some embodiments, the organic molecule and the metal cation interact via a covalent interaction. In certain embodiments, the covalent interaction is an ionic bond. In other embodiments, the covalent interaction is a coordinate bond.

In some embodiments, the organic molecule and the metal cation interact via a non-covalent interaction. In certain embodiments, the non-covalent interaction is a van der Waals force. In other embodiments, the non-covalent interaction is a hydrogen bond. In yet other embodiments, the non-covalent interaction is a hydrophobic interaction. In other embodiments, the non-covalent interaction is an electrostatic interaction.

In some embodiments, the organic molecule comprises an atom or a functional group capable of donating an electron pair to the metal cation. In certain aspects, the atom or the functional group is selected from the group consisting of S-donor, O-donor, N,O-donor, N-donor, P-donor, Lewis base, Shiff base, macrocycle, and N—N dimine donor.

In certain aspects, the atom or the functional group is selected from the group consisting of wherein the functional group is a chelate selected from the group consisting of Triazacyclononane, Tetraazacyclododecane, 1,8-Diamino-3,6,10,13,16,19-hexaazabicyclo[6,6,6]-eicosane, 1,4,8,11-Tetraazabicyclo[6.6.2]hexadecane, 1,4,8,11-Tetraazabicyclo[6.6.2]hexadecane-4,11-diacetic acid, 1,1,1-Trifluoroacetylacetone, 1,4,7-Trimethyl-1,4,7-triazacyclononane, 2,2'-Bipyrimidine, Acetylacetone, Alizarin, Amidoxime, Amidoxime group, Aminoethylethanolamine, Aminomethylphosphonic acid, Aminopolycarboxylic acid, ATMP, BAPTA, Bathocuproine, BDTH2, Benzotriazole, Bidentate, Bipyridine, 2,2'-Bipyridine, Bis(dicyclohexylphosphino)ethane, 1,2-Bis(dimethylarsino)benzene, 1,2-Bis(dimethylphosphino)ethane, 1,4-Bis(diphenylphosphino)butane, 1,2-Bis(diphenylphosphino)ethane, Calixarene, Carcerand, Catechol, Cavitand, Chelating resin, Chelex 100, Citrate, Citric acid, Clathrochelate, Corrole, Cryptand, 2.2.2-Cryptand, Cyclam, Cyclen, Cyclodextrin, Deferasirox, Deferiprone, Deferoxamine, Denticity, Dexrazoxane, Diacetyl monoxime, Trans-1,2-Diaminocyclohexane, 1,2-Diaminopropane, 1,5-Diaza-3,7-diphosphacyclooctanes, 1,4-Diazacycloheptane, Dibenzoylmethane, Diethylenetriamine, Diglyme, 2,3-Dihydroxybenzoic acid, Dimercaprol, 2,3-Dimercapto-1-propanesulfonic acid, Dimercaptosuccinic acid, 1,2-Dimethylethylenediamine, 1,1-Dimethylethylenediamine, Dimethylglyoxime, DIOP, Diphenylethylenediamine, 1,5-Dithiacyclooctane, Domoic acid, DOTA, DOTA-TATE, DTPMP, EDDHA, EDDS, EDTA, EDTMP, EGTA, 1,2-Ethanedithiol, Ethylenediamine, Ethylenediaminediacetic acid, Ethylenediaminetetraacetic acid, Etidronic acid, Fluo-4, Fura-2, Gallic acid, Gluconic acid, Glutamic acid, Glyoxal-bis(mesitylimine), Glyphosate, Hexafluoroacetylacetone, Homocitric acid, Iminodiacetic acid, Indo-1, Isosaccharinic acid, Kainic acid, Ligand, Malic acid, Metal acetylacetonates, Metallacrown, Nitrilotriacetic acid, Oxalic acid, Oxime, Pendetide, Penicillamine, Pentetic acid, Phanephos, Phenanthroline, O-Phenylenediamine, Phosphonate, Phthalocyanine, Phytochelatin, Picolinic acid, Polyaspartic acid, Porphine, Porphyrin, 3-Pyridylnicotinamide, 4-Pyridylnicotinamide, Pyrogallol, Salicylic acid, Sarcophagine, Sodium citrate, Sodium diethyldithiocarbamate, Sodium polyaspartate, Terpyridine, Tetramethylethylenediamine, Tetraphenylporphyrin, Thenoyltrifluoroacetone, Thioglycolic acid, TPEN, 1,4,7-Triazacyclononane, Tributyl phosphate, Tridentate, Triethylenetetramine, Triphos, Trisodium citrate, 1,4,7-Trithiacyclononane, and TTFA.

In various embodiments, the ligand is a therapeutic agent. As used herein, a "therapeutic agent" refers to any substance that, when administered in a therapeutically effective amount to a patient, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease.

In some embodiments, the therapeutic agent is diethyldithiocarbamatetrihydrate (DDC). DDC is a metabolite of disulfiram (DSF), which is a therapeutic agent most widely known for its efficacy as an alcohol-aversion drug. The chemical structure of DDC is:

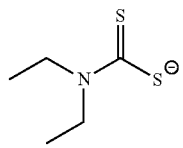

As used herein, the term "diethyldithiocarbamatetrihydrate" or "DDC" refers to DDC base, pharmaceutically acceptable salts of DDC, other salts of DDC, and metabolites of DDC. The term "pharmaceutically acceptable salt" refers to an addition salt that exists in conjunction with the acidic or basic portion of DDC. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. For example, pharmaceutically acceptable salts of DDC include but are not limited to DDC-$NH_4$, DDC-Li, DDC-H, DDC-Na, DDC-K, as well as hydrate and anhydrous forms.

Pharmaceutically acceptable salts of an acid addition nature are formed when a therapeutic agent and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when a therapeutic agent and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In some embodiments, the therapeutic agent is 1-pyrrolidinecarbodithioic acid ammonium salt (PDTC). PDTC is a therapeutic agent used for a variety of biochemical applications. The chemical structure of PDTC is:

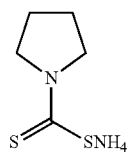

As used herein, the term "1-pyrrolidinecarbodithioic acid ammonium salt" or "PDTC" refers to DDC base, pharmaceutically acceptable salts of PDTC, other salts of PDTC, and metabolites of PDTC. The term "pharmaceutically acceptable salt" refers to an addition salt that exists in conjunction with the acidic or basic portion of PDTC.

In some embodiments, the therapeutic agent is sodium dimethyldithiocarbamate dihydrate (DMTC). DMTC is a therapeutic agent used for a variety of biochemical applications. The chemical structure of DMTC is:

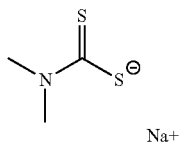

Na+

As used herein, the term "sodium dimethyldithiocarbamate dihydrate" or "DMTC" refers to DMTC base, pharmaceutically acceptable salts of DMTC, other salts of DMTC, and metabolites of DMTC. The term "pharmaceutically acceptable salt" refers to an addition salt that exists in conjunction with the acidic or basic portion of DMTC.

In certain embodiments, the therapeutic agent is a dithiocarbamate derivative of the formula $(R_1R_2\text{—}N\text{—}C(S)S^-)$ $X^+$. In some embodiments, the X is $NH_4^+$, $Li^+$, $H^+$, $Na^+$, $K^+$. In other embodiments, $R_1$ comprises an alkyl group or an ethyl group. In yet other embodiments, $R_2$ comprises an alkyl group or an ethyl group. In some embodiments, $R_1$ is —$CH_2CH_3$. In other embodiments, $R_1$ is —$CH_3$. In yet other embodiments, $R_2$ is —$CH_2CH_3$. In some embodiments, $R_2$ is —$CH_3$. In other embodiments, $R_1$ is pyrrolidine In yet other embodiments, $R_2$ is pyrrolidine.

In various embodiments, the therapeutic agent is a derivative of a compound selected from the group consisting of selenothiocarbamate, diselenocarbamate, thiocarbamate, carbamate, phosphino-dithioformate, dithiophosphate, xanthate, thioxanthate, and dithiocarboxylate.

In other embodiments, the therapeutic agent is selected from the group consisting of disulfiram, sodium diethyldithiocarbamatetrihydrate, pyrrolidinecarbodithioic acid ammonium salt, sodium dimethyldithiocarbamate dehydrate, 2-(Di-2-pyridinylmethylene)hydrazinecarbodithioic acid or its salt, pamidronate dithiocarbamate or its salt, finasteride dithiocarbamate or its salt, clioquinol, 2-(Di-2-pyridinylmethylene)hydrazinecarbodithioic acid or its salt, pyrithione, plumbagin, 8-hydroxyquinoline, 1,10-phenanthroline (PHEN), 2,2'-bipyridine, 2-hydroxy-1-naphthaldehyde-L-ornithine, 2,4-dihydroxybenzaldehyde-L-ornithine, quinoline-2-carboxaldehyde, taurine salicylic Schiff-base, L-methionine-o-vanillin Schiff base, valine-2-hydroxy-1-naphthaldehyde Schiff base, 2,4-diiodo-6-((pyridine-2-ylmethylamino) methyl)phenol, 3-indole acetic acid, 3-indole propionic acid, tri(hydroxymethyl)phosphine, methylated glycine, DL-alanine, 2,2-dimethyglycine, 4-amino-1,4-dihidro-3-(2-pyridyl)-5-thioxo-1,2,4-triazole, 3-aminopyridine-2-carboxaldehyde thiosemicarbazone, di-2-pyridylketone thiosemicarbazones, di-2-pyridylketone thiosemicarbazones, Piperazine-1,4-bisdithiocarbamate, 2-hydroxylethyl (isopropyl) dithiocarbamte, benzyl(methyl) dithiocarbamate, PBT2, glyoxal-bis(thiosemicarbazone), glyoxal bis(4-methylthiosemicarbazonato), diacetyl-bis(4-methylthiosemicarbazonato), elesclomol, pyrithione, metformin, aspirin, and doxorubicin.

In yet other embodiments, the therapeutic agent is selected from the group consisting of paclitaxel, docetaxel, and doxorubicin.

In some aspects, the therapeutic agent is an S-Donor System selected from Thiosemicarbazones (TSCs), Thiosemicarbazides, Dithiocarbamates (DTCs), Thioureas, and Dithiolates. In other aspects, the therapeutic agent is an O-Donor System such as Pyridine N-Oxides or κ2 O,O-Donor Systems. In other aspects, the therapeutic agent is a N,O-Donor System selected from Phenol Analogues, 8-Hydroxyquinoline, Naphthoquinones, Carboxylates, and Triethanolamines. In other aspects, the therapeutic agent is an N-Donor System selected from Pyrazoles, Pyrazole-Pyridine Systems, Imidazoles, Triazoles, Tetrazoles, Oxazoles, Indoles, Schiff Base Systems, κ2 N,N' Systems, κ2 N,O Systems, κ2 S,N Systems, κ3 N,N',N" Systems, κ3 N,N',O Systems, Hydrazones, κ3 N,O,O' Systems, κ3 N,O,S Systems, and κ4 N,N',N",O Systems. In other aspects the therapeutic agent is a Polydentate and/or Macrocyclic System such as Tridentate Ligands or Tetradentate and Macrocyclic Ligands. In other aspects, the therapeutic agent is a P-Donor Phosphine System. In other aspects, the therapeutic agent is a C-Donor N-Heterocyclic Carbene System selected from N—N Diimine (N—N) Systems, (N—N)/Amino Acids Systems, Clip-phen Systems, (N—N)2(X) Systems, and (terpy)(N—N) and (terpy)2 Systems.

In certain embodiments, the ligand is an imaging agent. An "imaging agent" is well known to persons skilled in the art. In some aspects, wherein the imaging agent is selected from the group consisting of dicyanomethylene-4H-pyran, IR820, merocyanine, ICG, $NaYF_4$, ZW800-1Cy5.5, Cy5.5, Cy7, IRDye680, IRDye800, Alexa Fluor 750, Cyanine-type, IRDye800CW, gold nanoclusters, and poly(benzo[1,2-b:3, 4-b']difuran-alt-fluorothieno-[3,4-b]thiophene). In other aspects, the imaging agent is an infrared dye. In some aspects, the imaging agent is a metallic dye. In certain aspects, the imaging agent is a MRI contrast agent.

In certain embodiments, the ligand is a photosensitizer. A "photosensitizer" is well known to persons skilled in the art. In various embodiments, the photosensitizer is selected from the group consisting of porfimer sodium, 5-aminolevulinic acid (ALA), methyl aminolevulinate (MAL), hexaminolevulinate (HAL), benzoporphyrin derivative monoacid ring A (BPD-MA), meta-tetra(hydroxyphenyl) chlorin (m-THPC), tin ethyl etiopurpurin, N-aspartyl chlorin e6 (NPe6), 2-(1-Hexyloxyethyl)-2-devinylpyropheophorbide (HPPH), palladium bacteriopheophorbide (WST09), WST11, motexafin lutetium (Lu-Tex), aluminum phthalocyanine tetrasulfonate (AlPcS4), and silicon phthalocyanine (Pc4).

In certain embodiments, the first composition comprises two ligands. In some embodiments, the first ligand is a therapeutic agent and the second ligand is an imaging agent. In other embodiments, the first ligand is a first therapeutic agent and the second ligand is a second therapeutic agent. In some embodiments, the second therapeutic agent is selected from the group consisting of nucleic acids, DNA, RNA, peptides, proteins, antibodies, cytokines, and small molecule chemical drugs. In other embodiments, the second therapeutic agent is incorporated through the interaction with the nanoparticle complex. In yet other embodiments, the second therapeutic agent is incorporated through the interaction with the stabilizer.

In some embodiments, the second therapeutic agent comprises a functional group that interacts with the nanoparticle complex. In various aspects, the functional group is introduced to the second therapeutic agent to enhance interaction with the nanoparticle complex. In other aspects, the second therapeutic agent is selected from the group consisting of an anticancer agent and an immunomodulation agent.

In certain embodiments, the M of the formula $M_nX_y$ has a 3+ charge. In other embodiments, M has a 2+ charge. In yet other embodiments, M has a 1+ charge.

In some embodiments, M is a Group 4 (IV B) metal selected from the group consisting of titanium, zirconium, and hafnium. In other embodiments, M is a Group 5 (V B) metal selected from the group consisting of Vanadium, Niobium, and Tantalum. In yet other embodiments, M is a Group 6 (VI B) metal selected from the group consisting of Chromium, Molybdenum, and Tungsten. In some embodiments, M is a Group 7 metal selected from the group consisting of Manganese, Technetium, and Rhenium. In other embodiments, M is a Group 8 (VIIIB) metal selected from the group consisting of Iron, Ruthenium, and Osmium. In yet other embodiments, M is a Group 9 (VIIIB) metal selected from the group consisting of Cobalt, Rhodium, and Iridium. In some embodiments, M is a Group 10 (VIII) metal selected from the group consisting of Nickel, Palladium, and Platinum. In other embodiments, M is a Group 11 (I B) metal selected from the group consisting of Copper, Silver, and Gold. In yet other embodiments, M is a Group 12 (II B) metal selected from the group consisting of Zinc, Cadmium, and Mercury.

In some embodiments, M is selected from the group consisting of titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, and mercury. In some aspects, M is a radioactive metal cation. In other aspects, M is selected from the group consisting of Sc-44, Ti-46, V-48, Mn-52, Co-55, Cu-64, Ga-68, and Zr-89.

In certain embodiments, the X of the formula $M_nX_y$ is selected from the group consisting of chloride, iodide, fluoride, bromide, nitrate, sulfate, arsenate, arsenite, hydrogen sulfate, thiosulfate, sulfite, perchlorate, chlorate, chlorite, hypochlorite, carbonate, bicarbonate, acetate, cyanide, cyanate, thiocyanate, hydroxide, phosphate, hydrogen phosphate, dihydrogen phosphate, nitrite, iodate, bromate, hypobromite, chromate, dichromate, and permanganate.

In certain aspects, in the formula $M_nX_y$, n is 1 and y is 1. In other aspects, n is 1 and y is 2. In yet other aspects, n is 1 and y is 3. In other aspects, n is 2 and y is 1. In yet other aspects, n is 3 and y is 1.

In certain embodiments. the second composition further comprises one or more stabilizers. In illustrative embodiments, the method further comprises a step of providing a third composition comprising one or more stabilizers. In some embodiments, the third composition is a solution. In some aspects, the method further comprises a step of combining the third composition with the first composition and the second composition. In some embodiments, the nanoparticle complex further comprises the stabilizer after combination of the third composition with the first composition and the second composition. In some embodiments, the stabilizer is attached to the surface of the nanoparticle complex. In other embodiments, the stabilizer is attached to the core of the nanoparticle complex.

In certain aspects, the stabilizer can comprise an amphiphilic composition such as those listed as FDA approved "Generally Recognized as Safe: (GRAS), as well as other excipients with acceptable safety profiles, including PEG-PLA, PEG-PCL, DSPE-PEG, TPGS, Poloxamer 188, and Pluronic F-127.

In certain embodiments, the third composition comprises a hydrophilic composition. In some aspects, the hydrophilic composition does not form liposomes. In other aspects, the hydrophilic composition does not form micelles.

In certain embodiments, the third composition comprises an amphiphilic composition. In some aspects, the amphiphilic composition does not form liposomes.

In various embodiments, the stabilizer is an amphiphilic composition. In some embodiments, the amphiphilic composition comprises at least one hydrophilic component and at least one hydrophobic component. In some embodiments, the amphiphilic composition comprises an anionic surfactant. In certain aspects, the anionic surfactant is selected from the group consisting of alkyl carboxylates-fatty acid salts, carboxylate fluoro surfactants, alkyl sulfates (e.g., sodium lauryl sulfate), alkyl ether sulfates (e.g., sodium laureth sulfate), docusates (e.g., dioctyl sodium sulfosuccinate), alkyl benzene sulfonates, alkyl aryl ether phosphates, alkyl ether phosphates, sodium lauryl sulphate BP, branched alkyl sulphate, sodium dodecyl sulphate, LITHIUM DODECYL SULFATE, Sodium octyl sulfate, Decyltrimethylammonium chloride, CETYLDIMETHYLETHYLAMMONIUM BROMIDE, Potassium oleate, Sodium pentanesulfonate, Sodium dodecyl sulfate, BUTYLNAPHTHALENESULFONIC ACID SODIUM SALT, Morpholineethanesulfonic acid, Sodium 1-butanesulfonate, SODIUM DECYL SULFATE, LIGNOSULFONIC ACID CALCIUM SALT, Sodium dodecylbenzenesulphonate, Sodium stearate, Magnesium stearate, 1-DODECANESULFONIC ACID SODIUM SALT, Sodium allylsulfonate, 3-(N,N-Dimethylpalmitylammonio) propanesulfonate, Sulfonated castor oil, 2,6-DIMORPHOLIN-4-YLPYRIMIDINE-4-CARBOXYLIC ACID, disodium methylenebisnaphthalenesulphonate, sodium oleyl sarcosinate, LY 171883, Sodium alkylbenzene sulfonate, Silk softener, Hydroxyaluminum distearate, SODIUM DIISOBUTYL SULFOSUCCINATE, DODECYLBENZENESULFONIC ACID SODIUM SALT, DICYCLOHEXYL SULFOSUCCINATE SODIUM SALT, Disodium 4-dodecyl-2,4'-oxydibenzenesulfonate, Linear Alklybezene Sulfonates, Organosilicon surfactant, SULFONATED ALIPHATIC POLYESTER, SODIUM-N-METHYL-N-OLEYL TAURATE, DI-N-HEXYL SODIUM SULFOSUCCINATE, Dibasic Lead Stearate, Sodium n-octylsufonate, dodecyl triethanolamine sulfate, SODIUM DIAMYL SULFOSUCCINATE, Manganous stearate, CALCIUM DODECYLBENZENE SULFONATE, disodium 4-[2-[(1-oxoundec-10-enyl)amino]ethyl] 2-sulphonatosuccinate, Fluorocarbon surfactant, Sodium poly[(naphthaleneformaldehyde) sulfonate], 1-HEXADECANESULFONIC ACID SODIUM SALT, Ammonium lauryl sulfate, 1-PENTANESULFONIC ACID SODIUM SALT MONOHYDRATE, Sodium lignosulfonate, Dodecylbenzenesulphonic acid, Sodium lauryl polyoxyethylene ether sulfate, amidoaminosurfactans, Jiuma plate amino-acid surfactant, cleaner LS, sodium nonylphenol polyoxyethylene ether sulfate, SODIUM DODECYL SULFATE, fatty alcohol ammonium sulfate, lauryl polyoxyethylene ether triethanol amine salt, dodecyl phenyl ammonium sulfate, sodium pyrrolidone carbonate, N-acyl glutamate potassium salt, sodium polyalkyl phenyl polyoxyethylene ether sulfate, stearyltoluene sodium sulfonate, sec-alkyl sodium sulfate, sec-alkyl sodium sulfate, nonylphenyl polyoxyethylene ether sulfate triethanolamine, sopa, glyceryl ethercarboxylic acid salt, calcium stearyl lactate, monoethanolamine dodecyl sulfate, alkoxy ethanolamido sulfosuccinate sodium salt, mmonium dodecylbenzenesulphonate, dodecay diethanol amine sulfate, levelling agent S, and sodium dibenzyl amine enzene sulfonate.

In other embodiments, the amphiphilic composition comprises a Zwitterionic surfactant. In certain aspects, the Zwitterionic (amphoteric) surfactant is selected from the group consisting of lauryl betaine, BETAINE CITRATE, SODIUM LAUROAMPHOACETATE, Sodium hydroxymethylglycinate, (carboxymethyl)dimethyl-3-[(1-oxododecyl) amino]propylammonium hydroxide, RENNIN, Betaines, coco alkyldimethyl, (carboxymethyl)dimethyloleylammonium hydroxide, Cocoamidopropyl betaine, (carboxylatomethyl)dimethyl(octadecyl)ammonium, phospholipid, and lecithin.

In yet other embodiments, the amphiphilic composition comprises a cationic surfactant. In certain aspects, the cationic surfactant (ammonium salt or quaternary ammonium type) is selected from the group consisting of Tetramethylammonium acetate, Tetrabutylammonium hydrogen sulfate, Dodecyltrimethylammonium chloride, Benzalkonium chloride, Tetramethylammonium fluoride, Dioctadecyl dimethyl ammonium chloride, N-Hexadecyltrimethylammonium chloride, Benzyltriethylammonium chloride, Tetraethylammonium bromide, Trimethylstearylammonium Chloride, Tetrabutylammonium perchlorate, Stearyldimethylbenzylammonium chloride, Methyl trioctyl ammonium chloride, Cetrimide, Didecyl dimethyl ammonium chloride, Tetramethylammonium iodide, Tetrabutyl ammonium chloride, Dodecyl trimethyl ammonium bromide, N,N-Dimethyl-N-2-propenyl-2-propen-1-aminium chloride polymer with 2-propenamide, Tridodecyl methyl ammonium chloride, Quaternary ammonium compounds, benzyl-C12-14-alkyldimethyl chlorides, Tetrabutylammonium cyanoborohydride, BENZALKONIUM CHLORIDE, alkyl dimethyl benzyl ammonium chloride (n=14), Behenyl Trimethyl Ammonium Chloride, Flocculant ST, Benzyltrimethylammonium iodide, Tetrabutylammonium chloride monohydrate, DICOCO DIMETHYL AMMONIUM CHLORIDE, Octadecylamine N-oleoyl Sarcosinate, N,N-Dihexadecyl-N-methyl-1-hexadecanaminium chloride, benzyltrimeehyl ammonium chloride, TETRAMETHYLAMMONIUM FLUORIDE TETRAHYDRATE, Tetrabutylammonium fluoride, Dimethyldioctadecylammonium bromide, Tetramethylammonium sulfate, and Octadecy trimethyl ammonium bromide.

In other embodiments, the amphiphilic composition comprises a non-ionic surfactant. In certain aspects, the non-ionic surfactant is selected from the group consisting of polyol ester, Alkanolamide, APG type, Alkoxylates type, and Fatty Acid Alkyl Esters.

In yet other embodiments, the amphiphilic composition comprises a poly ester type surfactant. In certain aspects, the polyol ester type surfactant is selected from the group consisting of POLYETHYLENE GLYCOL MONOOLEYL ETHER, TRILAURIN, POE (20) ISOHEXADECYL ETHER, Glycerol tristearate, Sorbitan monopalmitate, TRIOLEIN, Hydroxypropyl methyl cellulose, Polyoxyethylene stearate, Docosanamide, SORBITAN TRIOLEATE, Polyoxyethylene lauryl ether, MONOOLEIN, Polyoxyethylene sorbitan monopalmitate, Propyleneglycol alginate, GLYCEROL MONOHYDROXYSTEARATE, Fatty acids, lanolin, iso-Presters, ACETYLATED SUCROSE DISTEARATE, dibenzyl biphenyl polyoxyethylene ether, additive AC1210, POLY(ETHYLENE GLYCOL) (N) DISTEARATE, PENTAERYTHRITOL TETRARICINOLEATE 10G [R], Isooctadecanoic acid, ester with 1,2,3-propanetriol, SUCROSE DISTEARATE, SORBITAN TRISTEARATE, glycerine monostearate, Fatty alcohol polyoxyethylene ether N=3, $C^\{12\~18\}$ fatty alcohol polyoxyethylene (35) ether, coconut oil alcohol acylamide, MONOMYRISTIN, ethylene glycol monostearate, MONOCAPRYLIN, glycerine monolaurate, Hydroxyethyl Cellulose, Glycerides coco mono, Fatty alcohol polyoxyethylene ether O-10, DILAURIN, MONOMYRISTIN, TRIDECETH-4, FATTY ACID METHYL ESTER MIX C8-C22, Trimethylolpropane t, SUCROSE COCOATE, CETYL LACTATE, BRIJ® 76, Sucrose stearate, Pentaerythrityl tetrastearate, Isopropyl myristate, MONOLAURIN, Glycerides lard mono-acetates, 1-Glyceryl caprate, Peregal 0-25, Deemulsifier SP-169, Additive AC1815, Tween 20, Tween 40, Tween 60, Tween 80, Tween 65, Tween 85, Span 8, Span 40, Span 60, Span 80, and Span 65.

In other embodiments, the amphiphilic composition comprises an alkanolamide type surfactant. In certain aspects, the alkanolamide type surfactant is Empilan CIS, 2-[bis(2-hydroxyethyl)amino]ethyl stearate.

In yet other embodiments, the amphiphilic composition comprises an APG type surfactant. (d) In certain aspects, the APG type surfactant is selected from the group consisting of alkyl phenyl polyoxyethylene ether, alkyl polyglucoside, dodecyl polyglucoside, and Alkyl polyglucoside.

In other embodiments, the amphiphilic composition comprises an alkoxylate type surfactant. In certain aspects, the alkoxylates type surfactant is selected from the group consisting of SORBITAN SESQUIOLEATE, Emulsifier FM, Emulsifier LAE-9, Emulsifier EL-40, Emulsifier (S-185), POE (2) OLEYL AMINE, polyoxyethylene (10) castor oil ether, $C^\{8\~9\}$ alkyl phenyl polyoxyethylene (8) ether, Emulsifier OP-4, octyl phenyl polyoxyethylene (3) ether, Emulsifier OP-40, $C^\{8\~9\}$ alkyl phenyl polyoxyethylene (15) ether, castor oil polyoxyethylene (90) ether, Emulsifier EL-60, castor oil poloxyethylene (30) ether, octyl phenyl polyoxyethylene (30) ether, HEXAETHYLENE GLYCOL MONOOCTYL ETHER, and nonyl phenyl polyoxyethylene (9) ether.

In yet other embodiments, the amphiphilic composition comprises a fatty acid alkyl ester surfactant. In certain aspects, the Fatty Acid Alkyl Ester surfactant is selected from the group consisting of MYRISTYL MYRISTATE, Isooctyl palmitate, and DECYL OLEATE. In certain embodiments, the amphiphilic composition is prepared by conjugating one or more hydrophobic materials to one or more hydrophilic materials. In some embodiments, the hydrophilic material is selected from the group consisting of Poly(N-isopropylacrylamide) (PNIPAM) and Polyacrylamide (PAM), Poly(2-oxazoline) and Polyethylenimine (PEI), Poly(acrylic acid), Polymethacrylate and Other Acrylic Polymers, Poly(ethylene glycol) and Poly(ethylene oxide), Poly(vinyl alcohol) (PVA) and Copolymers, Poly(vinylpyrrolidone) (PVP) and Copolymers, Polyelectrolytes, hyaluronic acid, heparin, chondroitin sulfate, chitosan, polyglutamate, poly-lysine, poly-histidine, hydrophilic peptide, hydrophilic protein, nucleic acid, and poly-saccharide. In other embodiments, the hydrophilic material has a molecular weight between about 1000 to about 1,000,000 g/mol. In yet other embodiments, the hydrophobic material comprises a drug, an imaging agent, a fatty acid, a phospholipid, a cholesterol, a cholic acid, or analogs thereof.

In certain aspects, the amphiphilic composition is a copolymer. In some embodiments, the copolymer is poly(ethylene glycol)-poly(L-lactide) (PEG-PLA). In other embodiments, the copolymer is poly(ethylene glycol)-poly(ε-caprolactone) (PEG-PCL).

In various embodiments, the amphiphilic composition comprises a copolymer comprising an A-B type, an A-B-A type, or a B-A-B type. In some embodiments, A is a hydrophilic block polymer selected from the group consisting of Methoxy poly(ethylene glycol), Poly[N-(2-hydroxypropyl) methacrylamide] (pHPMA), and Poly(methacrylic acid). In one embodiment, the hydrophilic block polymer is a linear polymer, a branched polymer, or a dendrimer. In some embodiments, B is a hydrophobic block polymer selected from the group consisting of poly(lactide), poly(lactide-co-glycolide), poly(caprolactone), poly(aspartic acid), Poly(lysine), Poly(styrene), Poly(benzyl-aspartate), poly(benzyl-aspartate), poly(propylene oxide), Poly(isoprene), and Poly(carbonate ester). In one embodiment, the hydrophobic block polymer is a linear polymer, a branched polymer, or a dendrimer.

In some aspects, the amphiphilic composition is an amphiphilic peptide. In some embodiments, the amphiphilic peptide is a synthetic peptide. In other embodiments, the amphiphilic peptide is produced with recombinant technology from a mammalian cell. In yet other embodiments, the amphiphilic peptide is produced with recombinant technology from a non-mammalian cell.

In some aspects, the amphiphilic composition is an amphiphilic protein. In some embodiments, the amphiphilic protein is produced with recombinant technology from a mammalian cell. In other embodiments, the amphiphilic protein is produced with recombinant technology from a non-mammalian cell.

In certain embodiments, the stabilizer is a hydrophilic polymer. In some aspects, the hydrophilic polymer is a polymer comprising a sulfate group. In some embodiments, the polymer comprising a sulfate group is dextran sulfate. In other embodiments, the polymer comprising a sulfate group is heparin sulfate. In yet other embodiments, the polymer comprising a sulfate group is chondroitin sulfate. In other embodiments, the polymer comprising a sulfate group is alginate sulfate.

In some aspects, the hydrophilic polymer is a polymer comprising a dithiocarbamate group. In certain aspects, the hydrophilic polymer is a synthetic hydrophilic polymer with dithiocarbamate functional group (e.g. PEG-dithiocarbamate). In other aspects, the hydrophilic polymer is a natural hydrophilic polymer with dithiocarbamate functional group (e.g. chitosan dithiocarbamate).

In certain embodiments, the stabilizer is a hydrophilic material. In some embodiments, the hydrophilic material can comprise cysteine, lysine, histidine, arginine, selenocysteine, or proline residues. For example, the hydrophilic material can be a synthetic polypeptide, a polypeptide produced with recombinant technology from mammalian or non-mammalian cells, a protein isolated from natural sources or produced with recombinant technology from mammalian or non-mammalian cells, a synthetic hydrophilic polymer conjugated with amino acid, or a natural hydrophilic polymer conjugated with amino acid.

In certain embodiments, the stabilizer does not comprise PEG5000. In other embodiments, the stabilizer does not comprise PEG2000.

For the disclosed method, the combination of compositions can be accomplished in various means. In certain aspects, the step of combining the first composition and the second composition is performed via vortexing. In some aspects, the step of combining the first composition and the second composition is performed using a mixing device. In some embodiments, the mixing device is a vortex device. In other embodiments, the mixing device is a microfluidics mixer. In yet other embodiments, the mixing device is a propeller mixer. In some embodiments, the mixing device is a turbine mixer. In other embodiments, the mixing device is a blender. In yet other embodiments, the mixing device is a sonicator. In some embodiments, the mixing device is a homogenizer. In other embodiments, the mixing device is a sprayer. In yet other embodiments, the mixing device is an eletrosprayer.

In some aspects, the combining of the first composition and the second composition is performed prior to the combination with the third composition. In other aspects, the combining of the first composition and the second composition is performed simultaneously with the combination with the third composition.

In certain embodiments, the nanoparticle complex further comprises a targeting moiety on a surface of the nanoparticle complex. In some embodiments, the targeting moiety is selected from the group consisting of small molecules, peptide, proteins, antibody, nucleic acids, and polymers. In various embodiments, the targeting moiety is a tumor targeting moiety. In some embodiments, the tumor targeting moiety is capable of binding to a protein or a receptor on the tumor. In other embodiments, the tumor targeting moiety is capable of binding to a protein or a receptor on a microenvironment of the tumor.

In various embodiments, the targeting moiety is attached to the nanoparticle complex via a covalent bond. In other embodiments, the targeting moiety is attached to the nanoparticle complex via a non-covalent interaction. In yet other embodiments, the targeting moiety is attached to the stabilizer via a covalent bond. In other embodiments, the targeting moiety is attached to the stabilizer via a non-covalent interaction.

In certain aspects, the nanoparticle complex further comprises a second therapeutic agent. In some embodiments, the second therapeutic agent is selected from the group consisting of nucleic acids, DNA, RNA, peptides, proteins, antibodies, cytokines, and small molecule chemical drugs. In other embodiments, the second therapeutic agent is incorporated through the interaction with the nanoparticle complex. In yet other embodiments, the second therapeutic agent is incorporated through the interaction with the stabilizer. In some embodiments, the second therapeutic agent comprises a functional group that interacts with the nanoparticle complex. In some aspects, the functional group is introduced to the second therapeutic agent to enhance interaction with the nanoparticle complex. In other embodiments, the second therapeutic agent is selected from the group consisting of an anticancer agent and an immunomodulation agent.

In certain embodiments, the nanoparticle complex has a particle size between about 10 nm to about 250 nm. In some embodiments, the nanoparticle complex has a particle size between about 25 nm to about 100 nm. In other embodiments, the nanoparticle complex has a particle size between about 25 nm to about 50 nm. In yet other embodiments, the nanoparticle complex has a particle size between about 50 nm to about 100 nm.

In certain embodiments, the nanoparticle complex has a concentration between about 0.1 mg/ml and about 200 mg/ml. In some embodiments, the nanoparticle complex has a concentration of the ligand between about 10 mg/ml and about 150 mg/ml. In some embodiments, the nanoparticle complex has a concentration of the ligand between about 1 mg/ml and 5 mg/ml. In some embodiments, the nanoparticle complex has a concentration of the ligand between about 2 mg/ml and 4 mg/ml. In some embodiments, the nanoparticle complex has a concentration of the ligand of about 2 mg/ml. In some embodiments, the nanoparticle complex has a concentration of the ligand of about 4 mg/ml. In other embodiments, the nanoparticle complex has a concentration of the ligand between about 10 mg/ml and about 50 mg/ml. In yet other embodiments, the nanoparticle complex has a concentration of the ligand between about 50 mg/ml and about 100 mg/ml. In other embodiments, the nanoparticle complex has a concentration of the ligand between about 100 mg/ml and about 150 mg/ml.

In certain embodiments, the method further comprises a step of removing one or more of aggregates and particles from the combination of the first composition and the second composition. In certain embodiments, the method further comprises a step of removing one or more of aggregates and particles from the combination of the first composition, the second composition, and the third composition. In some embodiments, the step of removing one or more of aggregates and particles is performed via filtration. In other embodiments, the step of removing one or more of aggregates and particles is performed via centrifugation.

In certain aspects, wherein the method further comprises a step of lyophilizing the nanoparticle complex. Methods of lyophilizing are well known to the skilled artisan. In various aspects, dimethyl sulfoxide (DMSO) is not used for making the nanoparticle complex.

In illustrative embodiments, a nanoparticle complex comprising at least one ligand and a metal cation is provided. The nanoparticle complex is formed from the method of making described herein. Any of the previously described embodiments regarding the method of making a nanoparticle complex are applicable to the nanoparticle complex.

In illustrative embodiments, a method of treating a disease in a patient in need thereof is provided. The method comprises the step of administering a therapeutically effective amount of a nanoparticle complex to the patient, wherein the nanoparticle complex comprises at least one ligand and a metal cation. Any of the previously described embodiments regarding the nanoparticle complex and methods associated with the nanoparticle complex are applicable to the method of treating a disease in a patient.

In various embodiments, the disease is cancer. In some embodiments, the cancer is selected from a bone cancer, a muscle cancer, a brain cancer, a nervous system cancer, a breast cancer, a prostate cancer, an endocrine system cancer, an eye cancer, a gastrointestinal cancer, a genitourinary cancer, a gynecologic cancer, a head and neck cancer, a hematopoetic cancer, a skin cancer, a thoracic and respiratory cancer, an HIV/AIDS-related cancer, or an unsorted cancer. In other embodiments, the cancer is breast cancer. In yet other embodiments, the cancer is prostate cancer. In other embodiments, the cancer is a relapsed cancer. In yet other embodiments, the cancer is a metastatic cancer. In some embodiments, the cancer is resistant or non-responsive to chemotherapy, hormone therapy, radiotherapy, or immunotherapy.

In various embodiments, the disease is an infectious disease. In some embodiments, the infectious disease is a bacterial infection. In other embodiments, the infectious disease is a viral infection. In yet other embodiments, the infectious disease is a fungal infection.

In various embodiments, the method further comprises administration of a second therapeutic agent. In certain embodiments, the administration to the patient is a parenteral administration. In some embodiments, the parenteral administration is an intravenous administration. In other embodiments, the parenteral administration is an intramuscular administration. In yet other embodiments, the parenteral administration is a subcutaneous administration. In some embodiments, the parenteral administration is an intradermal administration. In other embodiments, the parenteral administration is an intratumor administration.

In certain embodiments, the administration to the patient is a transdermal administration. In some embodiments, the administration to the patient is an oral administration. In other embodiments, the administration to the patient is an inhalation administration. In yet other embodiments, the administration to the patient is a local administration.

In illustrative embodiments, a method of identifying a disease in a patient is provided. The method comprises the step of administering a therapeutically effective amount of a nanoparticle complex to the patient, wherein the nanoparticle complex comprises at least one ligand and a metal cation. Any of the previously described embodiments regarding the nanoparticle complex and methods associated with the nanoparticle complex are applicable to the method of identifying a disease in a patient.

In various embodiments, the disease is cancer. In some embodiments, the cancer is selected from a bone cancer, a muscle cancer, a brain cancer, a nervous system cancer, a breast cancer, a prostate cancer, an endocrine system cancer, an eye cancer, a gastrointestinal cancer, a genitourinary cancer, a gynecologic cancer, a head and neck cancer, a hematopoetic cancer, a skin cancer, a thoracic and respiratory cancer, an HIV/AIDS-related cancer, or an unsorted cancer. In other embodiments, the cancer is breast cancer. In yet other embodiments, the cancer is prostate cancer. In other embodiments, the cancer is a relapsed cancer. In yet other embodiments, the cancer is a metastatic cancer. In some embodiments, the cancer is resistant or non-responsive to chemotherapy, hormone therapy, radiotherapy, or immunotherapy.

In various embodiments, the disease is an infectious disease. In some embodiments, the infectious disease is a bacterial infection. In other embodiments, the infectious disease is a viral infection. In yet other embodiments, the infectious disease is a fungal infection.

In certain embodiments, the administration to the patient is a parenteral administration. In some embodiments, the parenteral administration is an intravenous administration. In other embodiments, the parenteral administration is an intramuscular administration. In yet other embodiments, the parenteral administration is a subcutaneous administration. In some embodiments, the parenteral administration is an intradermal administration. In other embodiments, the parenteral administration is an intratumor administration.

In certain embodiments, the administration to the patient is a transdermal administration. In some embodiments, the administration to the patient is an oral administration. In other embodiments, the administration to the patient is an inhalation administration. In yet other embodiments, the administration to the patient is a local administration.

In certain embodiments, the nanoparticle complex is accumulated specifically in a disease organ or tissue. In some embodiments, the accumulated nanoparticle complex is capable of visualizing a tumor for image-guided surgery on the patient. In other embodiments, the nanoparticle complex comprises a probe or contrast agent to facilitate the visualization of disease site and monitor disease progression.

In illustrative embodiments, a kit is provided. The kit comprises a first composition, a second composition, and instructions for combining the first composition and the second composition, wherein the first composition comprises at least one ligand, and wherein the second composition comprises a salt of the formula $MnXy$, wherein M is a metal cation and X is counterion, and wherein n is an integer from 1 to 3 and y is an integer from 1 to 5. Any of the previously described embodiments regarding the nanoparticle complex and methods associated with the nanoparticle complex are applicable to the kit.

In some embodiments, the kit further comprises a third composition comprising one or more stabilizers. In various embodiments, the kit further comprises a mixing device.

EXAMPLE 1

Preparation of Nanoparticle Complexes

The nanoparticle complexes comprise at least one ligand and a metal cation. In this example, a $Cu(DDC)_2$ nanoparticle complex can be prepared from sodium diethyldithiocarbamatetrihydrate (DOC-Na) and copper chloride ($CuCl_2$).

The $Cu(DDC)_2$ nanocomplex was prepared in the instant example by combining a sodium diethyldithiocarbamatetrihydrate (DOC-Na) and copper chloride aqueous ($CuCl_2$) solution containing a stabilizer. The molar ratio between DOC-Na and $CuCl_2$ was 2:1.

DDC-Na was dissolved in 2% (w/v) DSPE-PEG2k micelle solution to get DOC-Na solution (2.84 mg/ml). $CuCl_2$ was dissolved in 2% (w/v) DSPE-PEG2k micelle solution to get $CuCl_2$ solution (0.75 mg/ml). The DOC-Na solution and $CuCl_2$ solution were combined and vortexed for 1 minute to form a $Cu(DDC)_2$ nanocomplex. The theoretical concentration of $Cu(DDC)_2$ prepared with this method is 1 mg/ml. The resulting formulation was centrifuges at 10,000 rpm for 10 minutes and filter with 0.45 uM membrane to remove large aggregations.

Figures 10A, 10B:
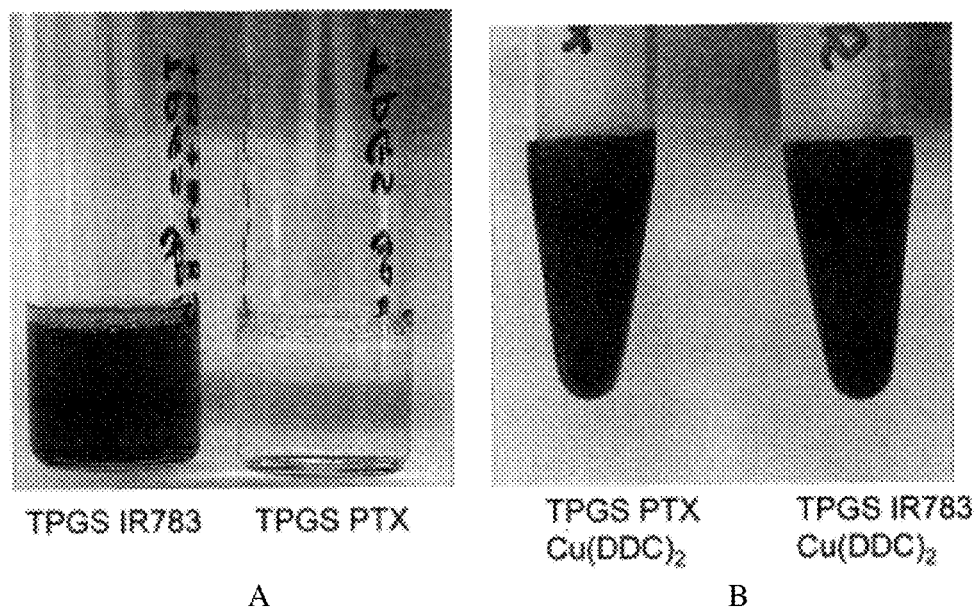
FIG. 10A shows solutions of TPGS IR783 (an infrared fluorescence dye) and paclitaxel (a chemotherapy drug).
FIG. 10B shows $Cu(DDC)_2$ nanoparticle complexes loaded with TPGS IR783 and paclitaxel.
Figure 11:
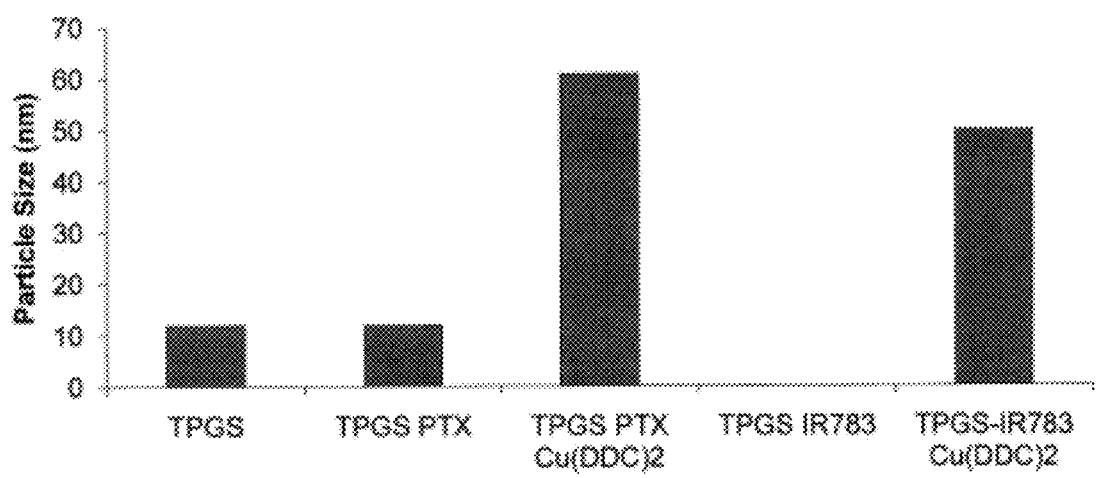
FIG. 11 shows the particle size of $Cu(DDC)_2$ nanoparticle complexes loaded with TPGS IR783 (an infrared fluorescence dye) and paclitaxel (a chemotherapy drug). TPGS was used as a stabilizer.

Furthermore, $Cu(DDC)_2$ nanoparticle complexes were prepared in the instant example using various other stabilizer materials by replacing DSPE.PEG2K with Pluronic® F-127 (F127), d-a-Tocopheryl polyethylene glycol 1000 succinate (TPGS), mPEG5000, mPEG2000, Bovine Serum Albumin (BSA). A higher concentration of $Cu(DDC)_2$ nanocomplex was also prepared by increasing DDC-Na and $CuCl_2$, respectively, prior to mixing. To prepare multifunctional nanocomplex containing IR783 (an infrared dye for tumor imaging) or paclitaxel (an anticancer drug), a TPGS micelle containing 0.5 mg/ml IR783 or 1 mg/ml paclitaxel was prepared, then used as stabilizers to prepare $Cu(DDC)_2$ nanocomplex according to the methods of the instant example. FIGS. 10A and 10B show the nanoparticle complexes containing IR783 and paclitaxel, respectively. FIG. 11 shows the particle size of $Cu(DDC)_2$ nanoparticle complexes loaded with TPGS IR783 and paclitaxel.

Various stabilizers, including DSPE-PEG2k, TPGS, F127, BSA, PEG5000, and PEG2000, were evaluated for formation of $Cu(DDC)_2$ nanoparticle complexes. In the absence of a stabilizer, DOC-Na and $CuCl_2$ were observed to form large $Cu(DDC)_2$ precipitation in DI water (see FIG. 1). The majority of stabilizers demonstrated outstanding performance, except for PEG5000 and PEG2000, which both failed to form $Cu(DDC)_2$ nanoparticle complexes.

EXAMPLE 2

Evaluation of Nanoparticle Complex Particle Size

The particle size of nanoparticle complexes can be evaluated. In this example, $Cu(DDC)_2$ nanoparticle complexes were evaluated.

The particle size of $Cu(DDC)_2$ nanoparticle complexes was measured with a Malvern Zetasizer Nano ZS. Briefly, $Cu(DDC)_2$ nanoparticle complexes (100-200 ul) were added into a microcuvette. The particle size and distribution were determined based on dynamic light scattering (DLS) at 173 degree scattering angle. Furthermore, morphology of $Cu(DDC)_2$ nanoparticle complexes can be observed using a transmission electron microscope. Samples can be loaded on a copper grid and stained with 1% uranyl acetate.

Figure 2:
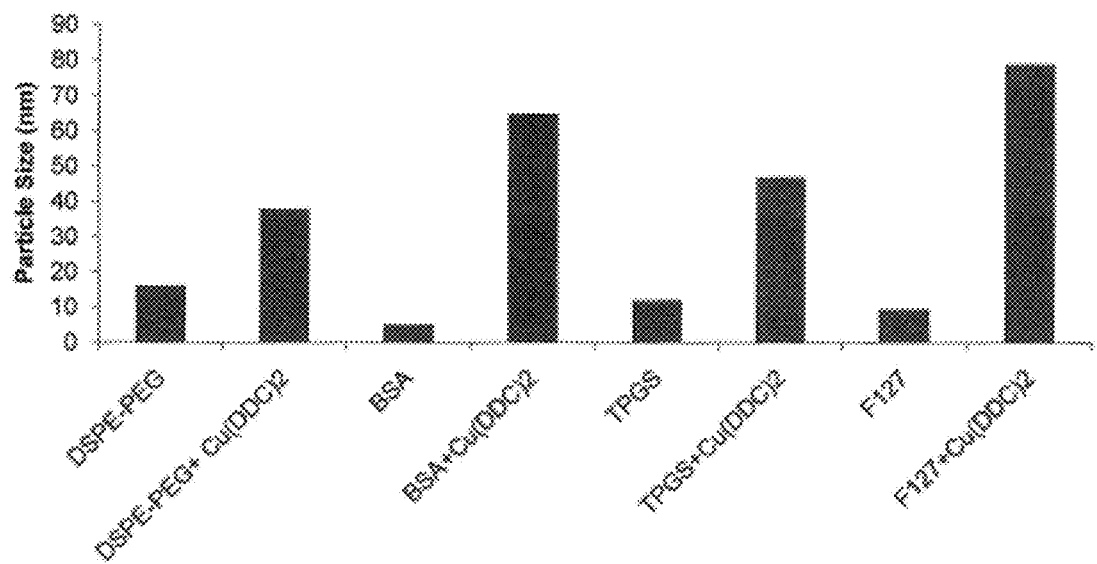
FIG. 2 shows the particle size of stabilizers and $Cu(DDC)_2$ nanoparticle complexes. The size of stabilizer micelles or solutions as well as $Cu(DDC)_2$ nanoparticle complexes prepared with different stabilizers were determined with dynamic light scattering. The $Cu(DDC)_2$ concentration was 1 mg/ml.

The particle size of $Cu(DDC)_2$ nanoparticle complexes was observed as dependent on the type of stabilizer used (see FIG. 2). The tunable particle size ranging from 38-85 nm could be prepared by selecting different stabilizers. The results also demonstrated that the particle size of $Cu(DDC)_2$ nanoparticle complexes was significantly larger than the pure stabilizer samples. In most cases, particle size distribution become more narrow (smaller POI) after the formation of $Cu(DDC)_2$ nanoparticle complexes. These results indicate a strong interaction between stabilizer and the $Cu(DDC)_2$ in the nanoparticle complex.

The stabilizers evaluated in the instant example can be divided into three major categories: i) amphiphilic materials (e.g., TPGS, F-127, DSPE-PEG), ii) proteins (e.g., BSA), and iii) hydrophilic polymers (e.g., PEG5000, PEG2000). Although PEG5000 and PEG2000 are historically used as nanoparticle stabilizers, they were not able to form stable nanoparticle complexes in the instant example. Both amphiphilic materials and proteins demonstrated excellent performance.

Without being limited by any theory, it is possible that these molecules can form micelle functions in order to guide the formation of $Cu(DDC)_2$ nanoparticle complexes. After the nanoparticle complexes reach a certain size, these materials can form a protection layer on the surface of the nanoparticle complexes to prevent their aggregation and further increase of particle size. This result may account for the stability of $Cu(DDC)_2$ nanoparticle complexes during storage.

Significant changes of particle size for at least 24 hours at room temperature were not observed. Due to the hydrophobic nature of $Cu(DDC)_2$, the hydrophobic portion of the stabilizer has a strong interaction with the $Cu(DDC)_2$ nanoparticle complexes and thus form a strong protective layer with the hydrophilic part in the interface between the nanoparticle complexes and aqueous medium.

The particle size of $Cu(DDC)_2$ nanoparticle complexes is about 38-85 nm, depending on the stabilizers used. The nanoparticle complexes generally has a narrow size distribution. The observed particle size (less than 100 nm) is considered to be a good candidate for passive tumor targeting through enhanced permeability and retention (EPR) effects. The stabilizer to be utilized can also be chemically modified to attach tumor targeting ligands such as folate, peptides, antibodies, and aspartames. The attachment of these targeting ligands can further enhance tumor targeting through active tumor targeting.

EXAMPLE 3

Evaluation of Nanoparticle Complex Concentrations

The concentrations of nanoparticle complexes can be evaluated. In this example, $Cu(DDC)_2$ nanoparticle complexes were evaluated.

The concentration of $Cu(DDC)_2$ was determined with a UV-VIS spectrometer. Briefly, a sample of $Cu(DDC)_2$ nanoparticle complexes was diluted with dimethylformamide (DMF) and the absorbance at 435 nm was determined. The $Cu(DDC)_2$ concentration was calculated based on the standard curve generated with a series different concentrations of $Cu(DDC)_2$ dissolved in DMF.

Figure 4:
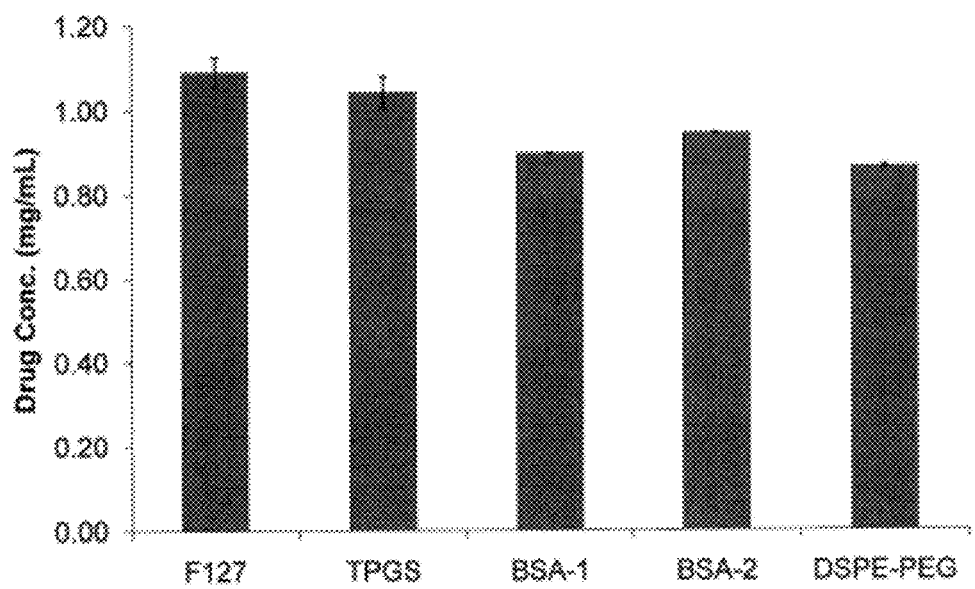
FIG. 4 shows the $Cu(DDC)_2$ concentrations of different $Cu(DDC)_2$ nanoparticle complexes. The theoretical $Cu(DDC)_2$ concentration was 1 mg/ml.
Figure 6:
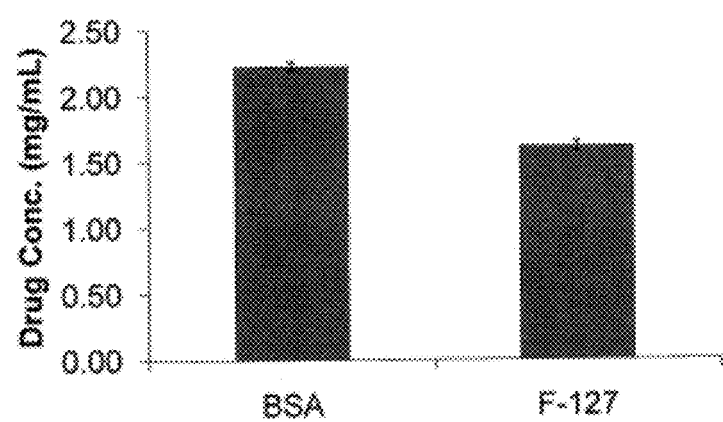
FIG. 6 shows the $Cu(DDC)_2$ concentrations of different $Cu(DDC)_2$ nanoparticle complexes. The theoretical $Cu(DDC)_2$ concentration was 2 mg/ml.

Results demonstrate that the nanoparticle complexes have a $Cu(DDC)_2$ concentration close to their theoretical drug concentration (i.e., 1 mg/ml). FIG. 4 shows no significant difference between nanoparticle complexes formulated with different stabilizers. FIG. 6 compares concentrations of nanoparticle complexes formulated with either BSA or F127 stabilizers (theoretical drug concentration 2 mg/ml).

Figure 5:
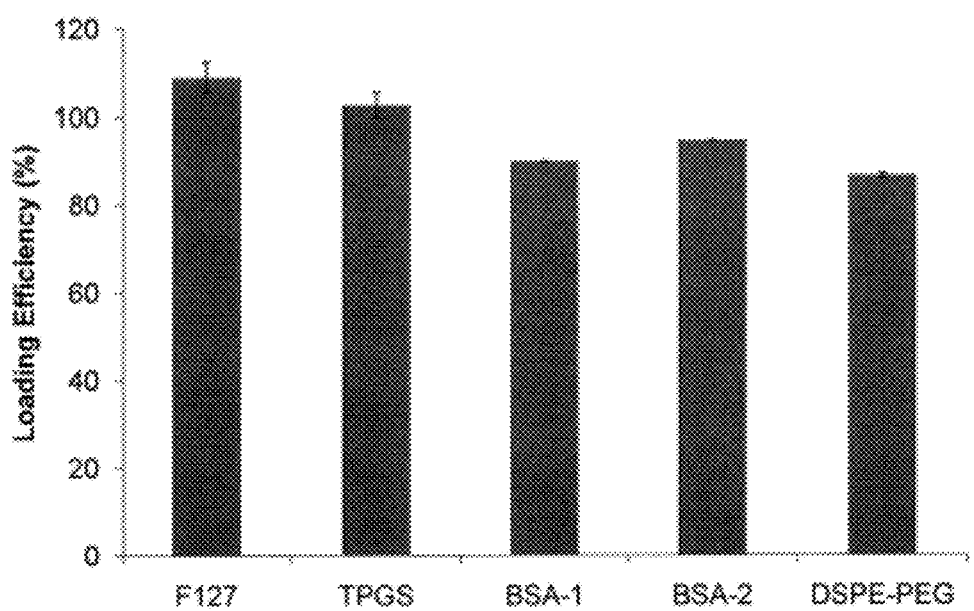
FIG. 5 shows the loading efficiency of different $Cu(DDC)_2$ nanoparticle complexes. The theoretical $Cu(DDC)_2$ concentration was 1 mg/ml.
Figure 7:
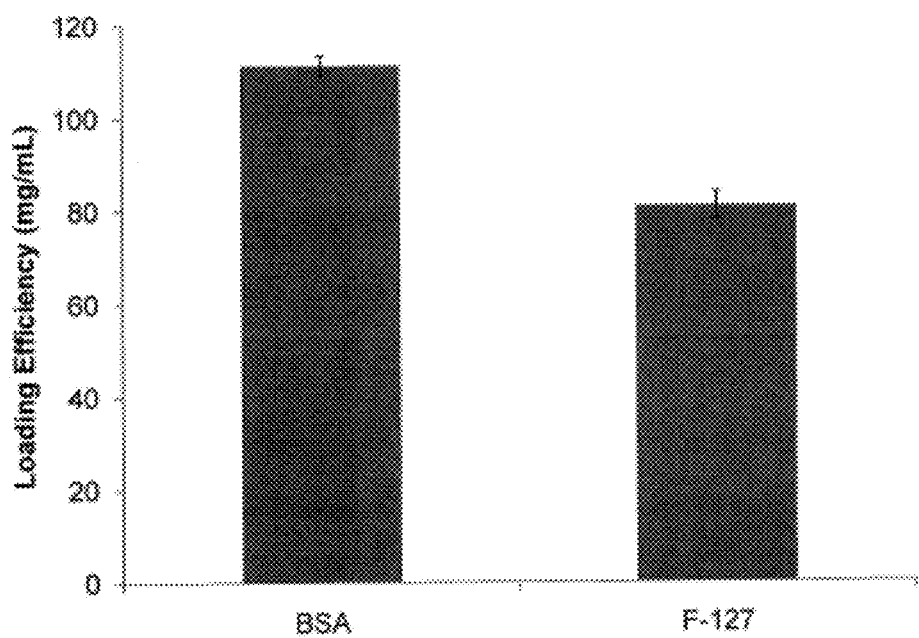
FIG. 7 shows the loading efficiency of different $Cu(DDC)_2$ nanoparticle complexes. The theoretical $Cu(DDC)_2$ concentration was 2 mg/ml.

Excellent drug loading efficiency or yield (close to 100%) was observed among the various nanoparticle complex formulations (see FIG. 5). These findings demonstrate high efficiency of forming $Cu(DDC)_2$ nanoparticle complexes with minimal occurrence of large precipitations. FIG. 7 compares loading efficiency of nanoparticle complexes formulated with either BSA or F127 stabilizers (theoretical drug concentration 2 mg/ml).

Figure 3:
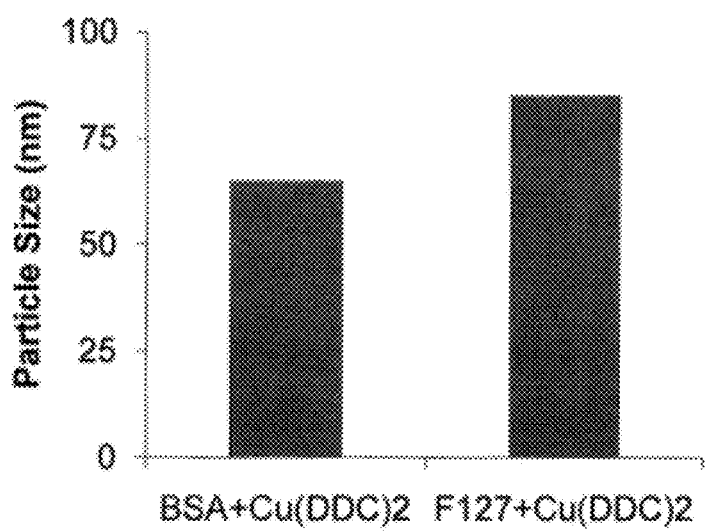
FIG. 3 shows the size of $Cu(DDC)_2$ nanoparticle complexes stabilized by BSA or F127. $Cu(DDC)_2$ concentration was 2 mg/ml.

A further increase of the theoretical drug concentration to 2 mg/ml was evaluated, with $Cu(DDC)_2$ nanoparticle complexes formation using the stabilizers BSA and F127. Similar high drug loading efficiency was observed and $Cu(DDC)_2$ concentrations were observed to be approximate to the theoretical drug concentration of 2 mg/ml. Further, the particle size did not significantly increase $Cu(DDC)_2$ concentration when theoretical drug concentration was increased from 1 mg/ml to 2 mg/ml. (see FIG. 3).

The drug loading efficiency of higher theoretical drug concentrations, and with using other stabilizers, can be evaluated to determine maximum drug loading capacity and the most efficient stabilizers to achieve the highest drug concentrations and loading efficiencies.

EXAMPLE 4

Therapeutic Effect of Nanoparticle Complex in Cancer Cells

The therapeutic effect of nanoparticle complexes on in vitro cancer cells can be evaluated. In this example, $Cu(DDC)_2$ nanoparticle complexes were evaluated.

MCF-7 breast cancer cells were cultured with a medium composed of RPMI 1640+10% Fetal Bovine Serum+1% Antibiotic-Antimycotic in a cell culture incubator (37° C., 5% $CO_2$). One day before evaluation, test cells were seeded into a 96-well plate.

Thereafter, a series of different concentrations of $Cu(DDC)_2$ nanoparticle complexes diluted in cell culture medium was prepared and placed into each well (approximately 100 µL/well). Cells were treated for 72 hours and observed via microscopy for morphology changes. The anticancer effects were also determined using an MTT assay. The absorbance was determined with a microplate spectrophotometer at a wavelength of 570 nm and a reference wavelength of 630 nm. Cell toxicity was calculated using the following equation:

$$\text{Viable Cells (\%)} = (A_{Test}/A_{control}) \times 100\%$$

The therapeutic effect of nanoparticle complexes on other cancer cells, such as prostate cancer cells, lung cancer cells, colon cancer cells, drug resistant cancer cells, and others can also be evaluated.

Figure 8:
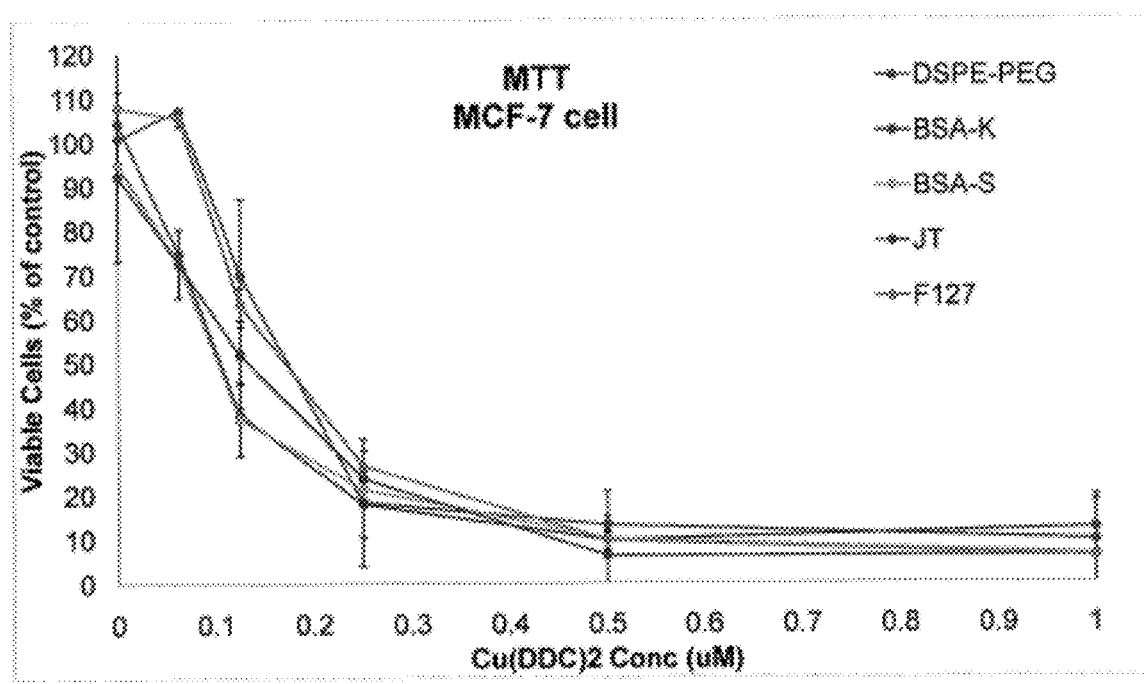
FIG. 8 shows the anticancer activities of different $Cu(DDC)_2$ nanoparticle complexes. For the "JT" embodiment, $Cu(DDC)_2$ micelles were prepared using a film dispersion method with $Cu(DDC)_2$ chemical.
Figure 9:
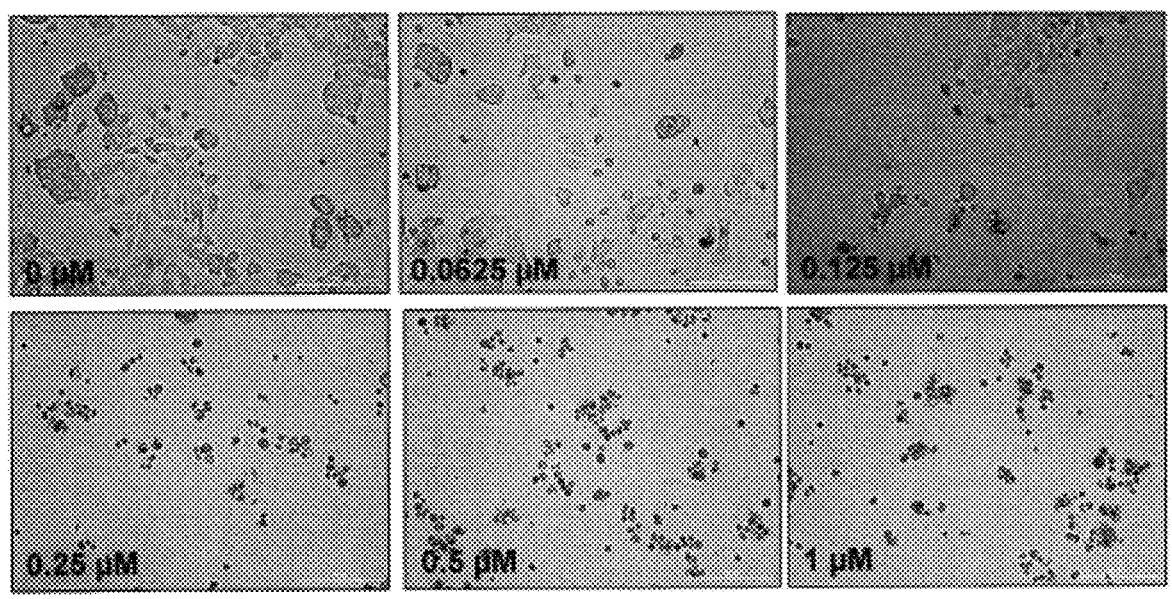
FIG. 9 shows the anticancer activities of different concentrations of $Cu(DDC)_2$ nanoparticle complexes. The change of cell morphology after treating with various concentrations of $Cu(DDC)_2$ nanoparticle complexes for 72 hours is presented. The various concentrations of a DSPE-PEG $Cu(DDC)_2$ nanoparticle complex are shown in the boxes.

As shown in FIG. 8, $Cu(DDC)_2$ nanoparticle complexes demonstrated potent anticancer activities. For example, concentration-dependent anticancer activities were observed on MCF-7 breast cancer cell lines. Further, the viability of cells decreased with an increase of drug concentration, with an $IC_{50}$ of approximately 100 nM. At concentrations above 250 nM, most of the treated cells were round-up and died (see FIG. 9). The activity between nanoparticle complexes prepared with pre-made $Cu(DDC)_2$ with nanocomplex formulations were evaluated, and all groups demonstrated similar anticancer activities.

EXAMPLE 5

Preparation of Lyophilized Nanoparticle Complex

The nanoparticle complexes can be lyophilized (e.g., freeze dried). In this example, lyophilized $Cu(DDC)_2$ nanoparticle complexes can be prepared.

$Cu(DDC)_2$ nanoparticle complexes can be frozen overnight at −80° C. Then, a sample of the frozen nanoparticle complexes can be freeze dried for 2 days until a dry sample cake is formed. The stability of freeze dried $Cu(DDC)_2$ nanoparticle complexes can be determined. Briefly, freeze dried samples can be kept at room temperature, at −4° C., and at −30° C. Thereafter, the samples can be reconstituted with DI water after time periods of 1 week, 1 month, 3 months, and 6 months. The reconstituted samples can be characterized by evaluating drug concentration and particle size.

EXAMPLE 6

Preparation of $Cu(DDC)_2$ Loaded Micelles

For comparison to the nanoparticle complexes of the present disclosure, $Cu(DDC)_2$ loaded micelles were prepared and evaluated. In the instant example, $Cu(DDC)_2$ loaded micelles were prepared with a film-dispersion method as known in the art. Briefly, 40 mg micelle-forming materials and a given amount of $Cu(DDC)_2$ were dissolved in 0.5 mL dichloromethane ($CH_2Cl_2$), and the solvent was removed under reduced pressure to form a film. The resulting film was hydrated in 1 mL deionized water and sonicated for 5 minutes. Unloaded $Cu(DDC)_2$ was removed by centrifugation at 12,000 rpm for 5 minutes. The supernatant was collected and filtered with 0.45-µM membrane filters.

Figure 12A:
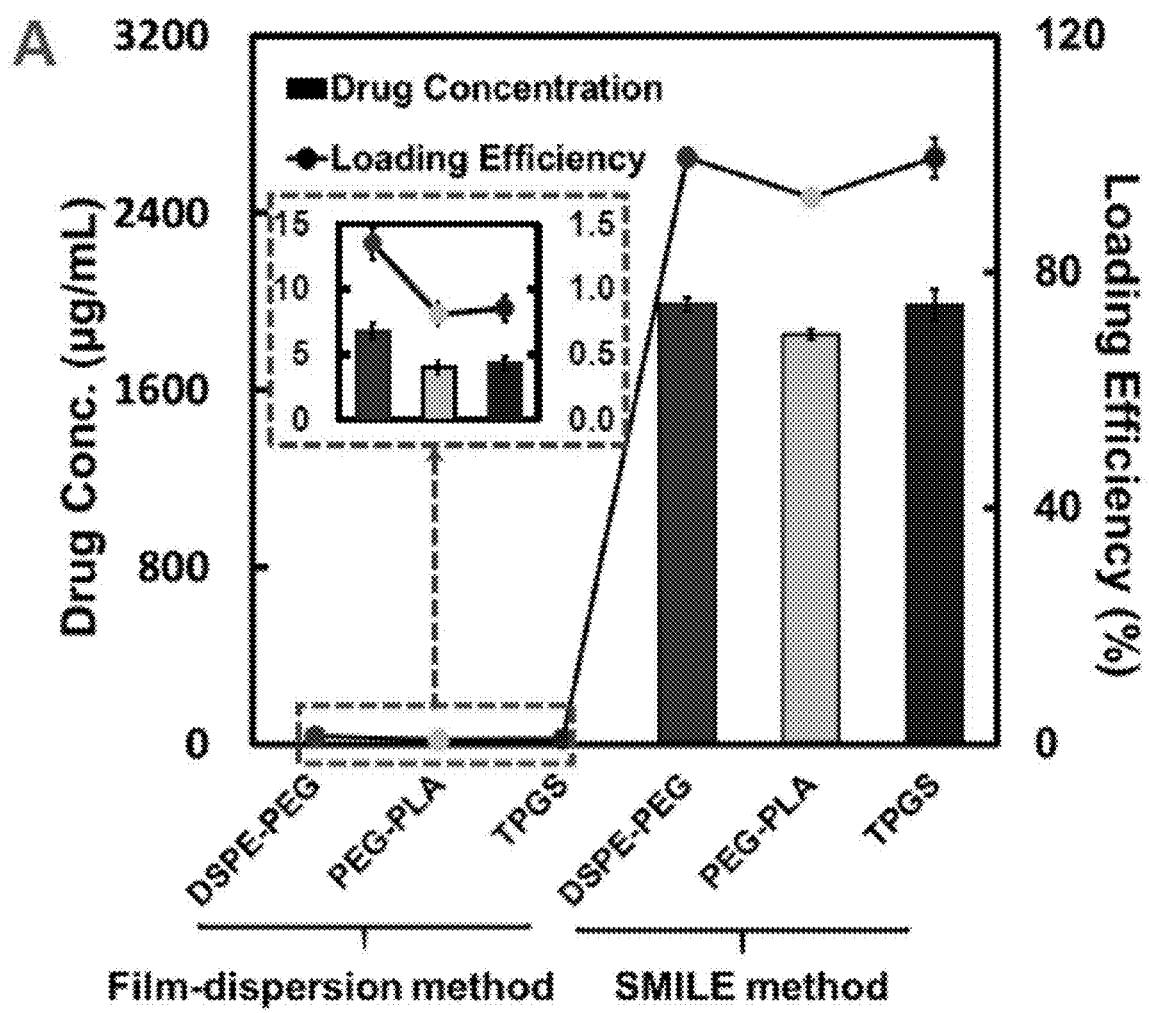
FIGS. 12A-12D show (A) Drug concentration and loading efficiency of $Cu(DDC)_2$ micelles prepared with a film-dispersion method (polymer 20 mg/mL) and $Cu(DDC)_2$ nanoparticle complexes prepared with a SMILE method (polymer 10 mg/mL). Results are the mean±SD (n=3). (B) Particle size and PDI of $Cu(DDC)_2$ nanoparticle complexes (2 mg/mL) prepared with different stabilizers (10 mg/mL). Results are the mean±SD (n=3). (C) Photos of $CuCl_2$, DDC-Na, and $Cu(DDC)_2$ nanoparticle complexes with different stabilizers (e.g., PEG-PLA, DSPE-PEG). Precipitations formed in water without a stabilizer or with a poor stabilizer (e.g., PEG2000). (D) The UV-visible spectrum of $Cu(DDC)_2$, DDC-Na, and $CuCl_2$.

Evaluation of $Cu(DDC)_2$ loaded micelles prepared using the film-dispersion method resulted in extremely low drug loading efficiency. The drug concentrations varied among different polymers tested, but none of them achieved satisfactory drug concentration and loading efficiency. The resulted drug concentration was below 10 ug/mL and drug loading efficiency was below 2% (see FIG. 12A; left columns and inserted panel).

EXAMPLE 7

Preparation of $Cu(DDC)_2$ Nanoparticle Complexes

For comparison, $Cu(DDC)_2$ nanoparticle complexes were prepared by combining sodium diethyldithiocarbamatetrihydrate (DDC-Na) and copper chloride aqueous ($CuCl_2$) solution containing a stabilizer. The molar ratio between DDC-Na and $CuCl_2$ was 2:1. Briefly, DDC-Na and $CuCl_2$ were dissolved in 1% (w/v) stabilizer to get a DDC-Na solution and a $CuCl_2$ solution, respectively. Then, DDC-Na solution and $CuCl_2$ solution were combined and vortexed for 1 minute to form $Cu(DDC)_2$ nanoparticle complexes. The resulting nanoparticle complex formulation was centrifuged at 10,000 rpm for 10 minutes and filtered with the 0.45 uM membrane to remove large aggregations. As demonstrated in the following examples, $Cu(DDC)_2$ nanoparticle complexes were prepared with a high drug concentration (2 mg/mL) and a high loading efficiency (close to 100%) and various stabilizers (e.g., DSPE-PEG, PEG-PLA, and TPGS) were evaluated (see FIG. 12A).

EXAMPLE 8

Particle Size, Morphology, Drug Concentration, and Loading Efficiency Evaluation of Nanoparticle Complexes In this example, $Cu(DDC)_2$ nanoparticle complexes were evaluated. The particle size and size distribution of nanoparticle complexes were determined by dynamic light scattering (DLS) using the Malvern Nano ZS. Briefly, a $Cu(DDC)_2$ nanoparticle complex sample (200 µL) was added to a micro-cuvette. The particle size and size distribution were determined based on DLS at a 173-degree scattering angle.

The morphology of nanoparticle complexes was characterized using a High Resolution Transmission Electron Microscope (HRTEM, JEM-2100F, JEOL). Samples were loaded onto a grid and stained with 1% uranyl acetate. The grid was visualized under the electron microscope.

The concentration of $Cu(DDC)_2$ nanoparticle complexes was determined with a UV-VIS spectrometer. Briefly, $Cu(DDC)_2$ nanoparticle complex samples were diluted with dimethylformamide (DMF) and the absorbance at 435 nm was determined. The $Cu(DDC)_2$ concentration was calculated based on the standard curve generated with different concentrations of $Cu(DDC)_2$. Drug loading efficiency was calculated using the following equation.

Drug Loading Efficiency (%)=(Actual Drug Concentration/Theoretical Drug Concentration)×100%

Figure 12B:
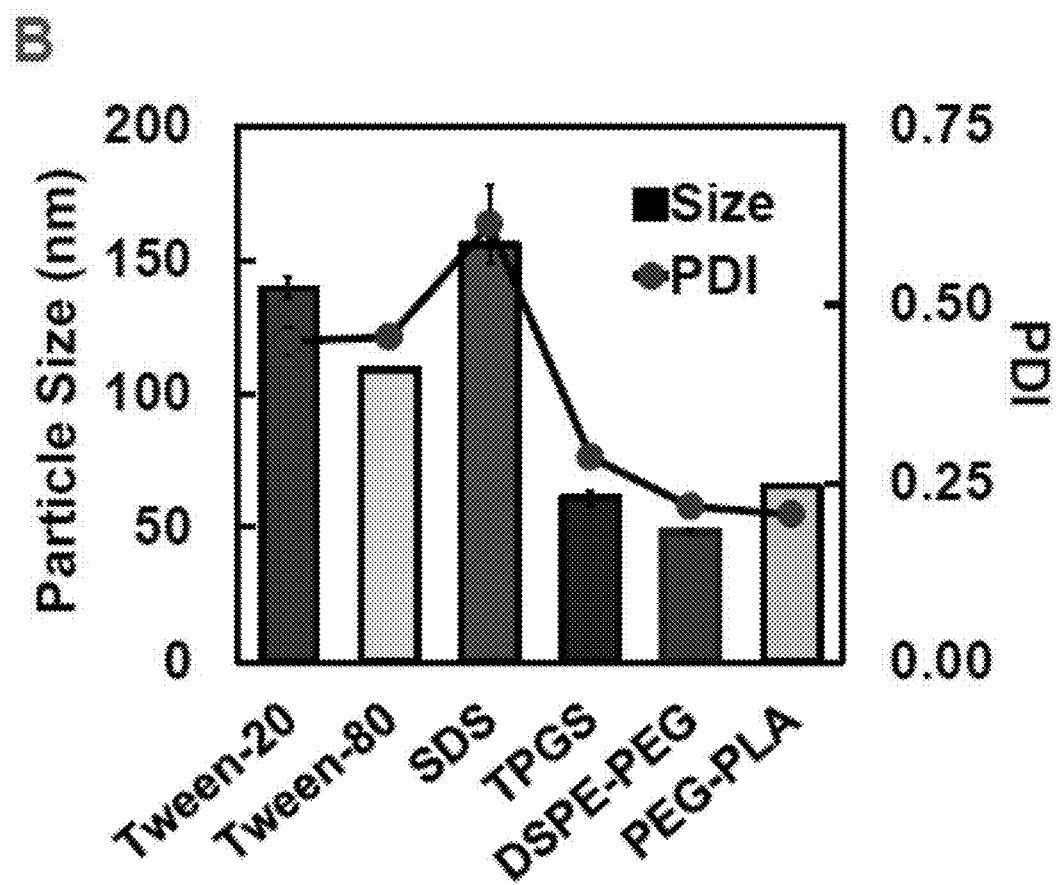
Figure 12C:
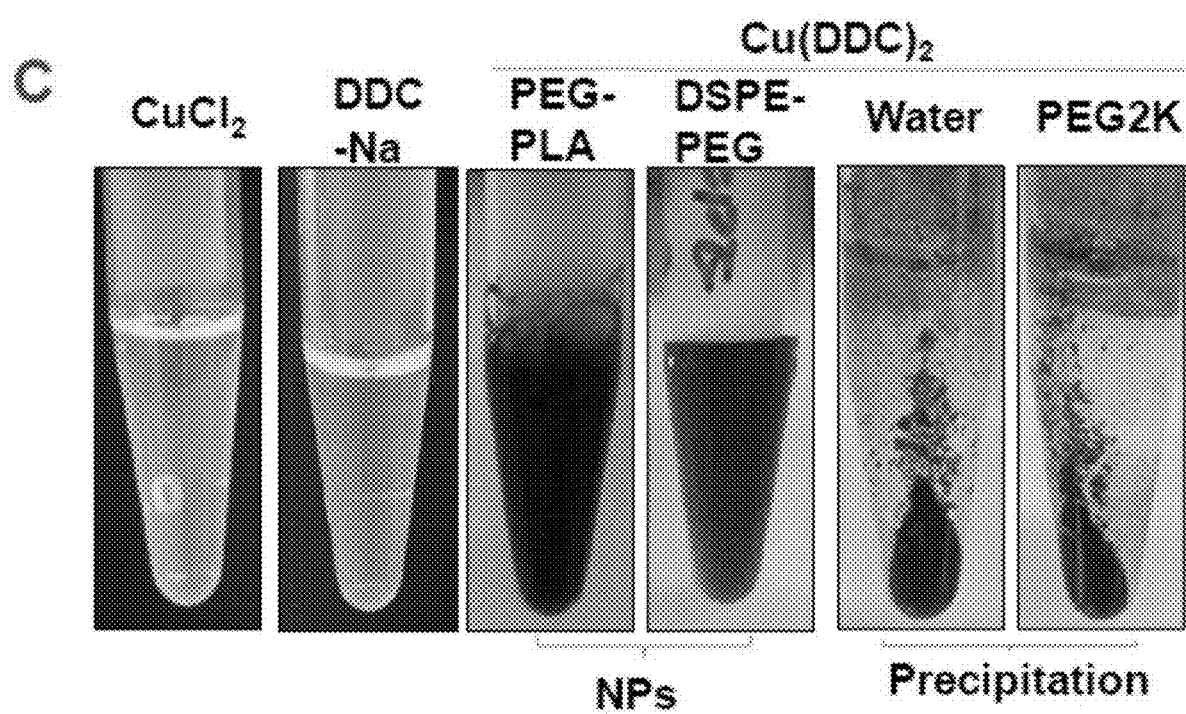
Figure 12D:
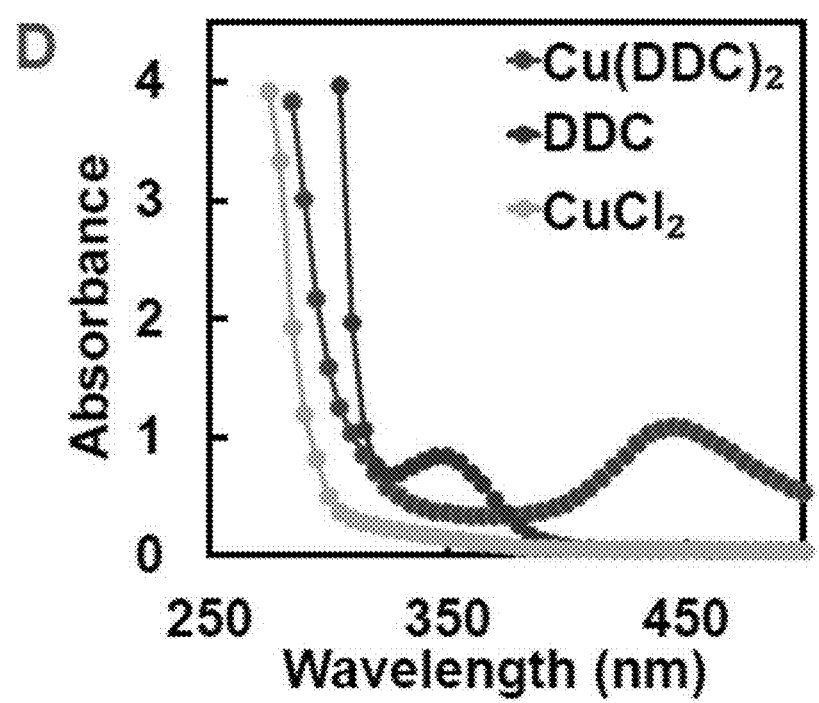

The formation of $Cu(DDC)_2$ nanoparticle complexes was confirmed by colorimetric visualization and by UV-VIS spectroscopy. The formed, stable $Cu(DDC)_2$ nanoparticle complexes demonstrated a dark color in the presence of various stabilizers (e.g., PEG-PLA, DSPE-PEG), while precipitation formed with a poor stabilizer or without a stabilizer (FIG. 12C). The UV-Vis spectrum showed that the $Cu(DDC)_2$ has a characteristic peak around 450 nm, which is absent in pure DDC-Na or $CuCl_2$ solutions (FIG. 12D).

The effects of theoretical drug concentrations and different stabilizers on actual drug concentrations and loading efficiencies were evaluated (FIGS. 19A-19B and 20A-20B). At the theoretical drug concentrations of 2 mg/mL or 4 mg/mL, both TPGS and DSPE-PEG at concentrations ranging from 0.5% to 4%, could all generate nanoparticle complexes with high drug loading efficiency (close to 100%). The drug loading efficiency was slightly lower in 4 mg/mL theoretical drug concentration groups compared to the 2 mg/mL groups. When the polymer stabilizer concentrations were at high levels (e.g., 2% or 4% of TPGS and DSPE-PEG, respectively), those groups with lower theoretical drug concentrations (e.g., 0.5 mg/mL and 1 mg/mL of $Cu(DDC)_2$) showed significantly decreased $Cu(DDC)_2$ drug loading efficiencies. However, when the polymer stabilizer concentrations were at low levels (e.g., 0.5% or 1%), those groups with similar low theoretical drug concentrations (e.g., 0.5 mg/mL and 1 mg/mL of $Cu(DDC)_2$) showed much higher drug loading efficiencies.

Figures 21A, 21B:
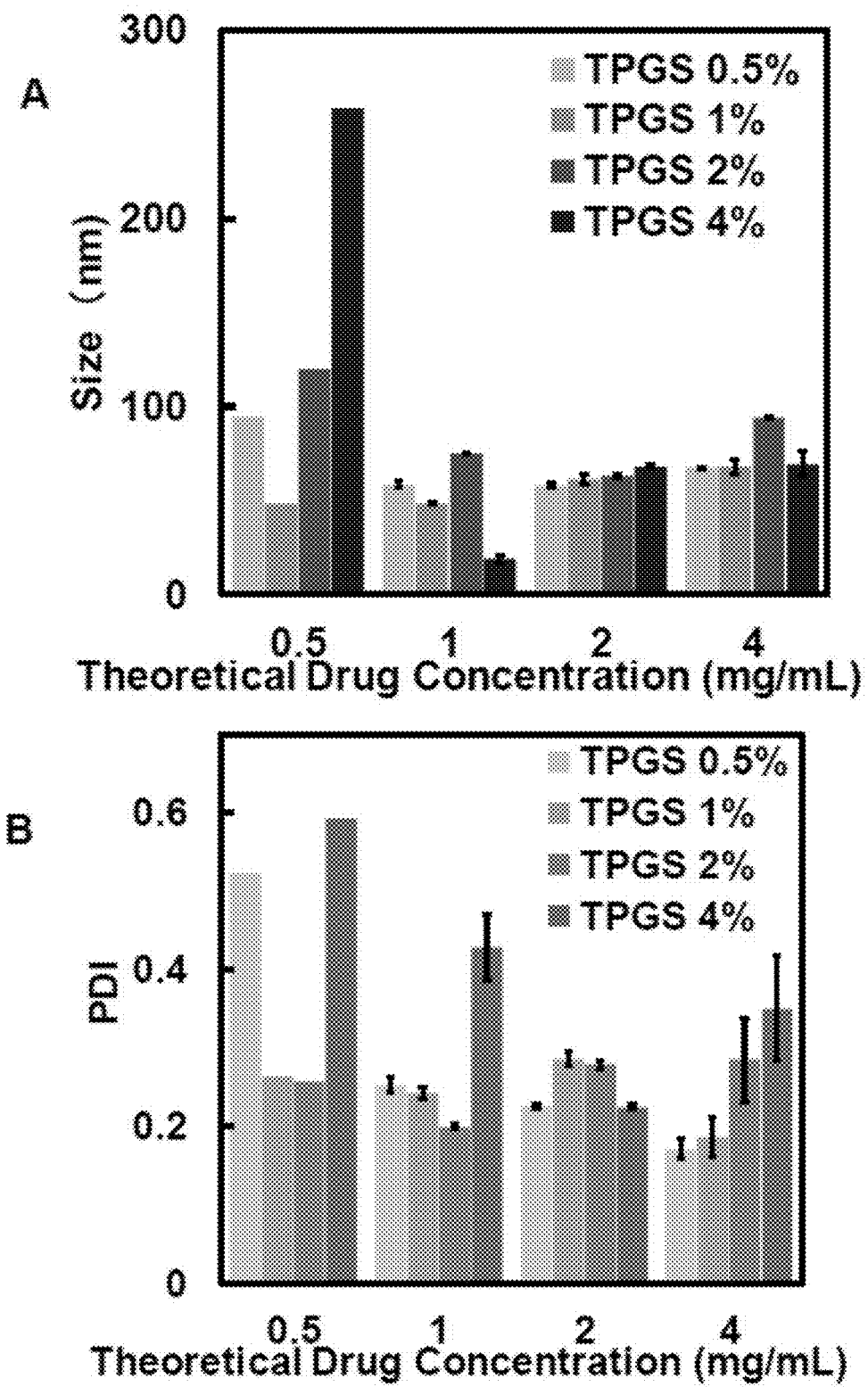
FIGS. 21A-21B show the effects of theoretical drug concentration and TPGS concentration on nanoparticle complex particle size (A) and polydispersity index (PdI) (B). Results are the mean±SD (n=3).
Figures 22A, 22B:
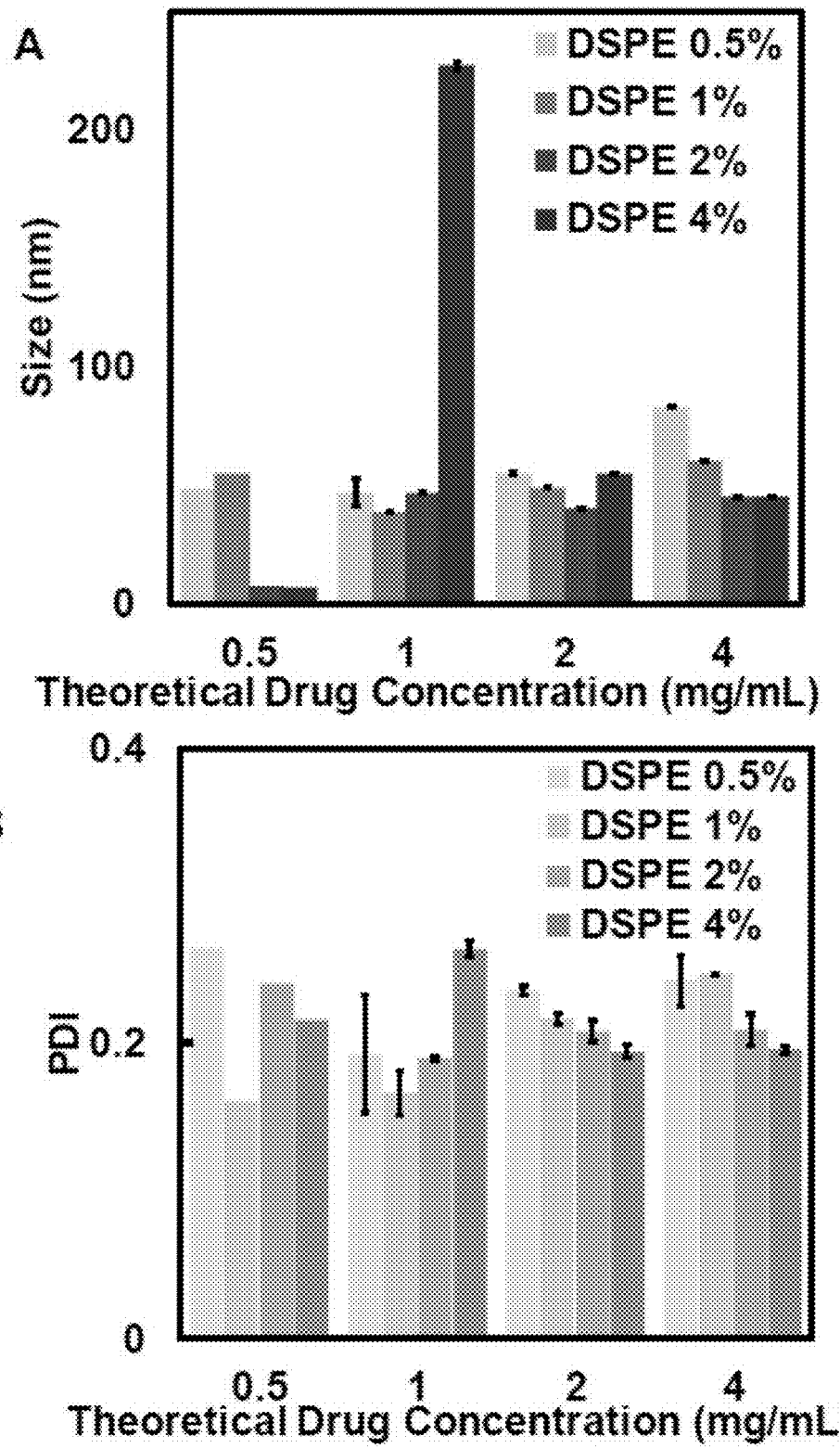
FIGS. 22A-22B show the effects of theoretical drug concentration and DSPE-PEG concentration on nanoparticle complex particle size (A) and polydispersity index (PdI) (B). Results are the mean±SD (n=3).

The effects of theoretical drug concentration and stabilizer concentration on the particle size and polydispersity index (PDI) were also evaluated. When the theoretical drug concentration was 2 mg/mL or 4 mg/mL, nanoparticle complexes exhibited a size of 60-70 nm if prepared with TPGS stabilizer at the concentrations ranging from 0.5% to 4%. These nanoparticle complexes also showed a good size distribution as indicated by the small PDI value (FIGS. 21A-21B). However, when the theoretical drug concentration was set to be 1 mg/mL or 0.5 mg/mL, the particle size varied significantly depending on the concentrations of TPGS used. These nanoparticle complexes also showed large PDI values indicating a broad particle size distribution. A similar trend was also observed in nanoparticle complexes prepared with DSPE-PEG as the stabilizer. Nanoparticle complexes of well-controlled particle size were prepared when theoretical drug concentrations were 2 mg/mL or 4 mg/mL with DSPE-PEG at concentrations ranging from 0.5% to 4%. The particle sizes were in the range of 40 nm to 80 nm, depending on the DSPE-PEG and drug concentrations (FIG. 22A-22B). All of these formulated nanoparticle complexes demonstrated a narrow particle size distribution (small PDI value). At lower theoretical drug concentrations (0.5 mg/mL or 1 mg/mL), nanoparticle complexes showed a large variation of particle sizes and large PDI values.

These results suggest that the interaction between DDC- and $Cu^{2+}$ during the complex formation is important for the nanoparticle complex preparation. This interaction can be influenced by the concentrations of DDC- and $Cu^{2+}$.

Figure 23:
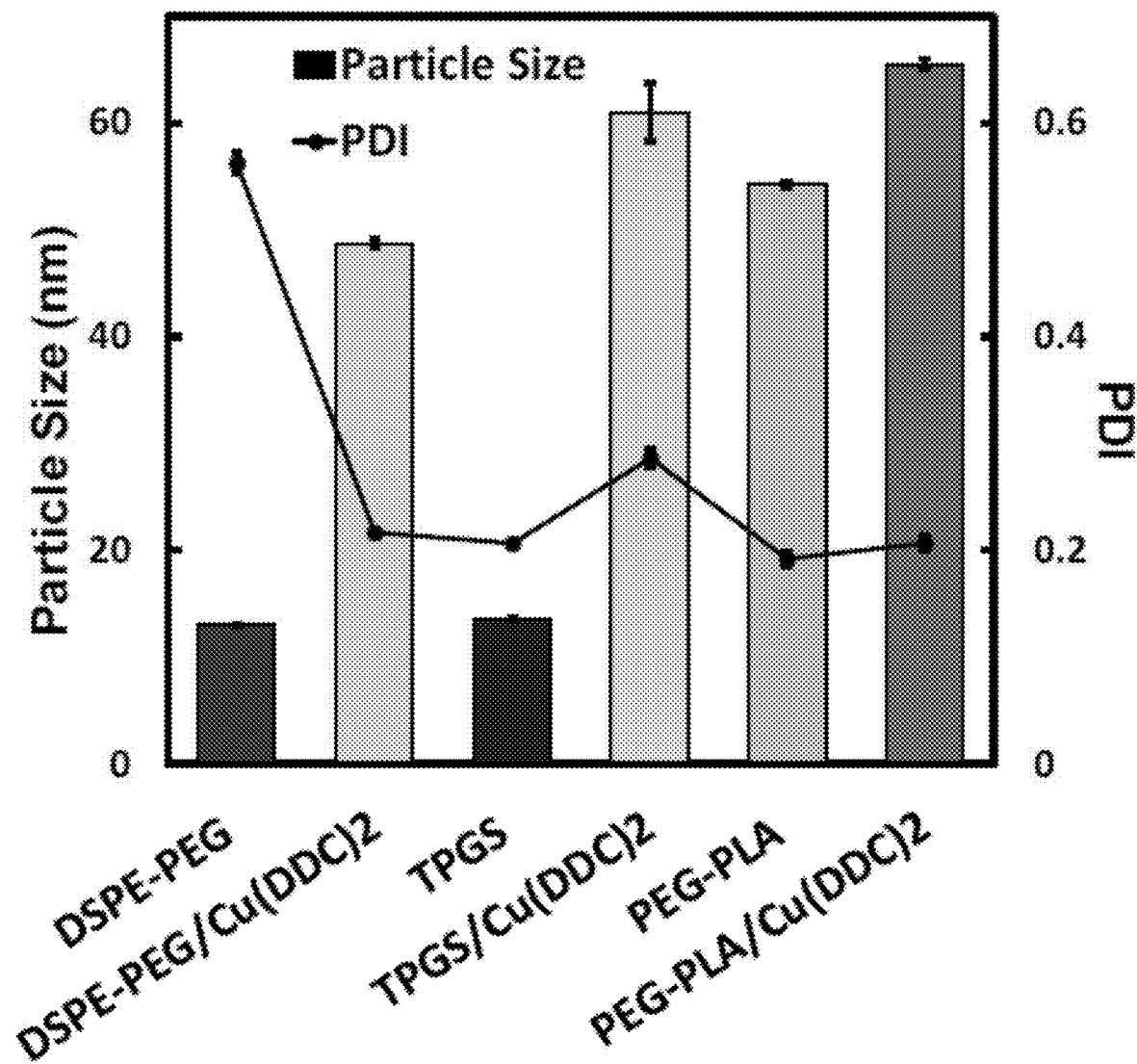
FIG. 23 shows the particle size of 2 mg/mL Cu(DDC)$_2$ nanoparticle complexes and corresponding stabilizers without Cu(DDC)$_2$. Polymer concentrations were 1%. Results are the mean±SD (n=3).
Figures 24A, 24B:
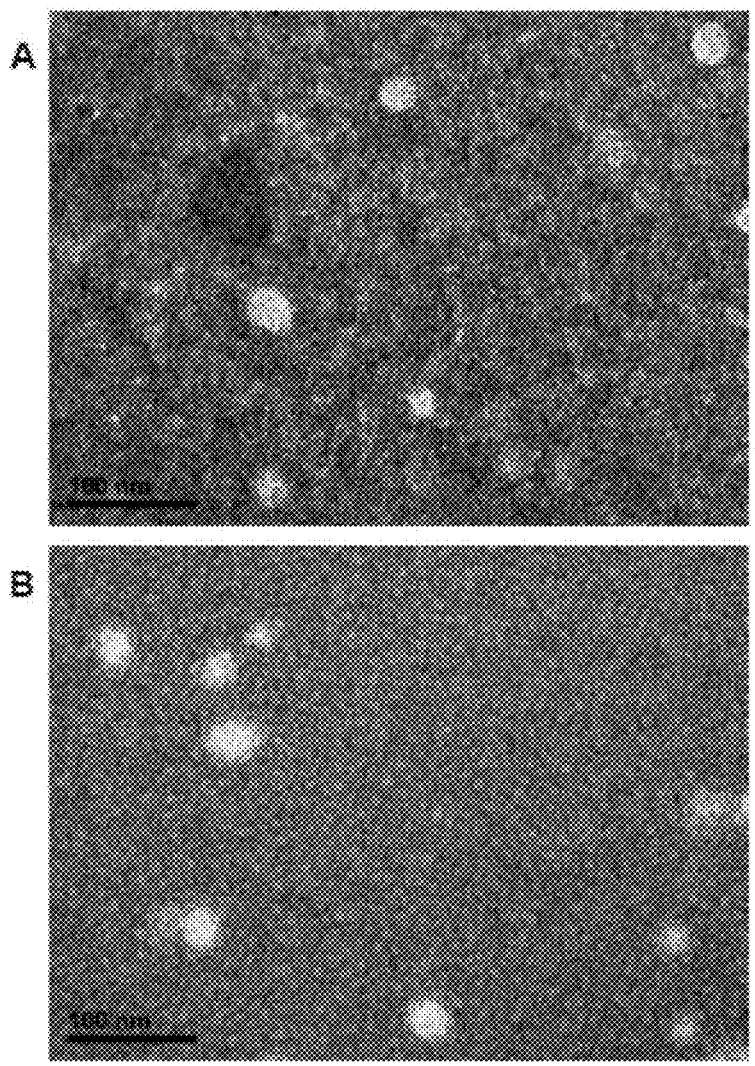
FIGS. 24A-24B show results from transmission electron microscopy (TEM) of (A) PEG-PLA micelles and (B) PEG-PLA/Cu(DDC)$_2$ nanoparticle complexes. Samples were stained with stained with 1% uranyl acetate.

The preparation of $Cu(DDC)_2$ nanoparticle complexes with additional stabilizers (e.g., Tween-20, Tween-80, and Sodium dodecyl sulfate (SDS)) was also evaluated. All of the evaluated stabilizers could be successfully used to prepare $Cu(DDC)_2$ nanoparticle complexes with particle sizes ranging from 50 nm to 150 nm. The selection of stabilizers had an impact on the particle size and PDI (FIG. 12B). Compared with the micelle solutions of DSPE and TPGS, the corresponding $Cu(DDC)_2$ nanoparticle complexes showed significant larger particle sizes. In contrast, the PEG-PLA micelle and PEG-PLA/$Cu(DDC)_2$ nanoparticle complexes had similar particle sizes (FIG. 23). The blank PEG-PLA and PEG-PLA/$Cu(DDC)_2$ nanoparticle complexes were characterized using the TEM, indicating spherical morphology and similar particle sizes (FIGS. 24A-24B).

EXAMPLE 9

Nuclear Magnetic Resonance (NMR) Evaluation of Nanoparticle Complexes

Figures 13A, 13B, 13C:
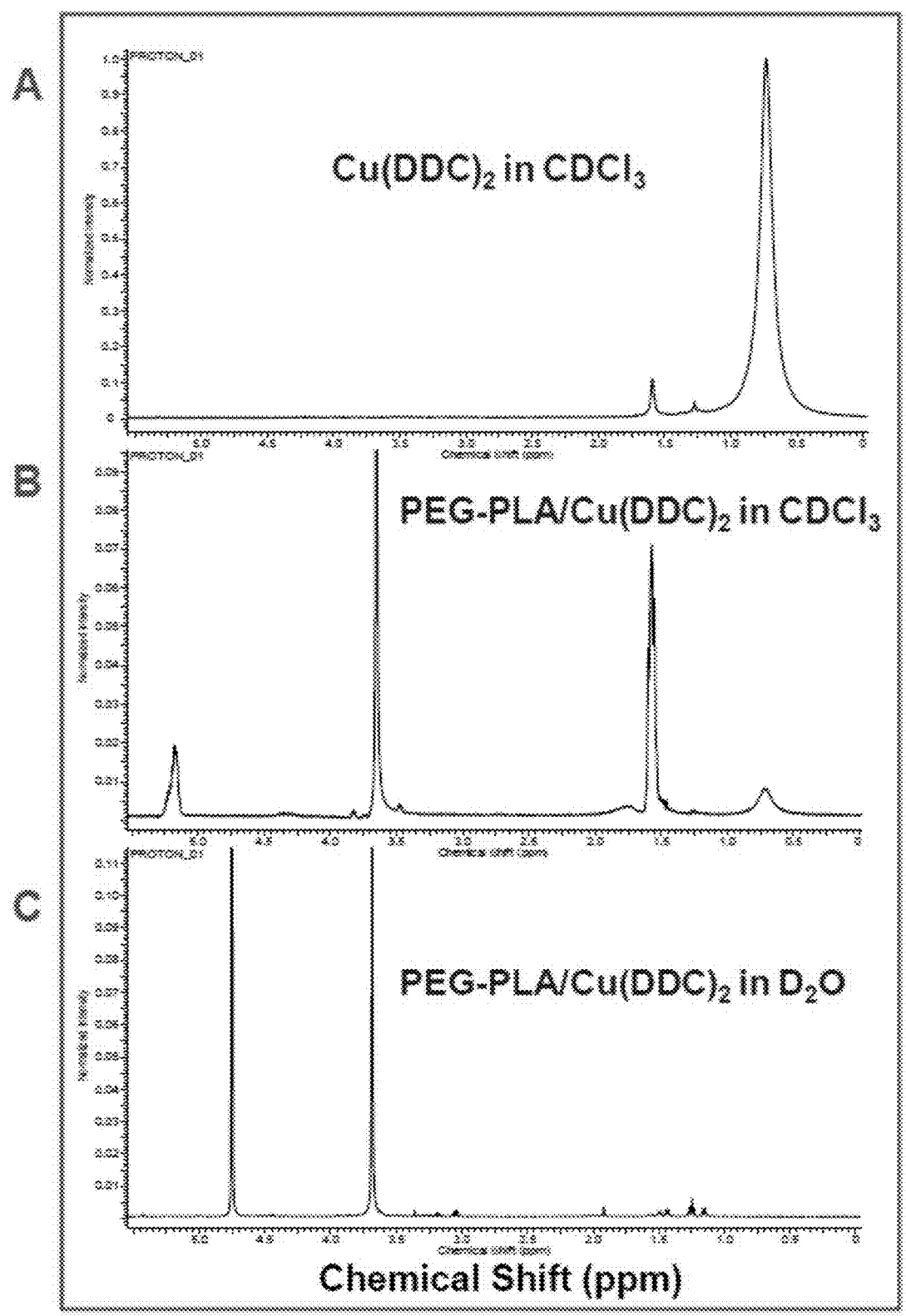
FIGS. 13A-13C show the core-shell structure of PEG-PLA $Cu(DDC)_2$ nanoparticle complexes. (A) $^1$H-NMR of $Cu(DDC)_2$ in $CDCl_3$; (B) $^1$H-NMR of PEG-PLA and $Cu(DDC)_2$ dissolved in $CDCl_3$; (C) $^1$H-NMR of PEG-PLA/$Cu(DDC)_2$ nanoparticle complexes formed in $D_2O$. PEG-PLA and $Cu(DDC)_2$ concentrations in B and C were 10 mg/mL and 2 mg/ml, respectively.

In this example, $Cu(DDC)_2$ nanoparticle complexes were evaluated. $^1$H NMR spectra were recorded on a Varian (400 MHz) using deuterated chloroform ($CDCl_3$) or deuterated water ($D_2O$) as a solvent. In this example, $^1$H NMR spectroscopy confirmed the formation of nanoparticle complexes and the structure of PEG-PLA $Cu(DDC)_2$ nanoparticle complexes was evaluated (FIG. 13A-13C). When all the components were dissolved in $CDCl_3$, peaks from the hydrophilic PEG block (3.6 ppm), the hydrophobic PLA block (5.1 and 1.7 ppm), and $Cu(DDC)_2$ (0.7 ppm) were all observed. When PEG-PLA $Cu(DDC)_2$ nanoparticle complexes were prepared in $D_2O$, peaks corresponding to hydrophobic PLA block and $Cu(DDC)_2$ were significantly diminished in contrast to the strong peaks for hydrophilic PEG block. These results demonstrated that the PEG-PLA/Cu$(DDC)_2$ nanoparticle complexes had a core-shell structure with $Cu(DDC)_2$ embedded inside the hydrophobic core of PEG-PLA micelles. The PEG-PLA surrounding $Cu(DDC)_2$ nanoparticle complexes stabilized the nanoparticle complexes and can prevent aggregation formation.

EXAMPLE 10

Stability Evaluation of Nanoparticle Complexes

In this example, $Cu(DDC)_2$ nanoparticle complexes were evaluated. Serum Stability: $Cu(DDC)_2$ nanoparticle complexes were mixed and incubated with 10% fetal bovine serum (FBS) at room temperature. The particle size was determined with DLS at the different time points. Long-term storage stability: Cu(DDC)$_2$ nanoparticle complexes were kept at room temperature and drug concentrations were determined on different days during storage.

Figure 14A:
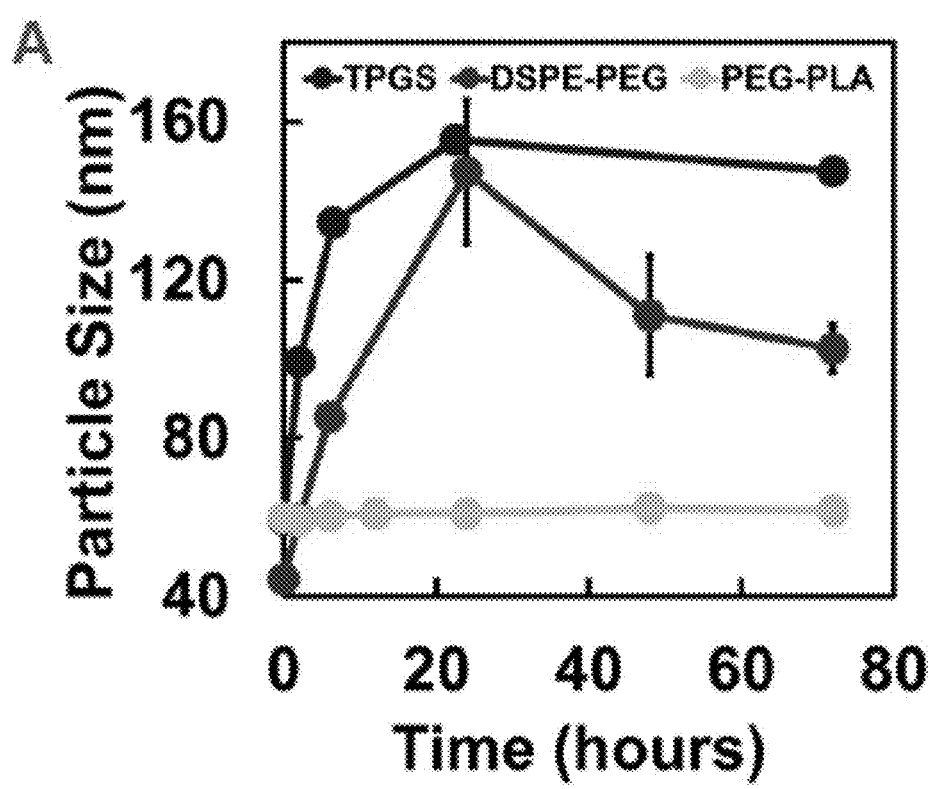
FIGS. 14A-14C show $Cu(DDC)_2$ nanoparticle complex stability. nanoparticle complexes prepared with different stabilizers were incubated in 10% FBS in PBS solution. Particle size (A) and PDI (B) was determined at different time points. (C) Storage stability of $Cu(DDC)_2$ nanoparticle complexes. Nanoparticle complexes were kept at room temperature and $Cu(DDC)_2$ concentration was determined at different time points. Results are the mean±SD (n=3).
Figure 14B:
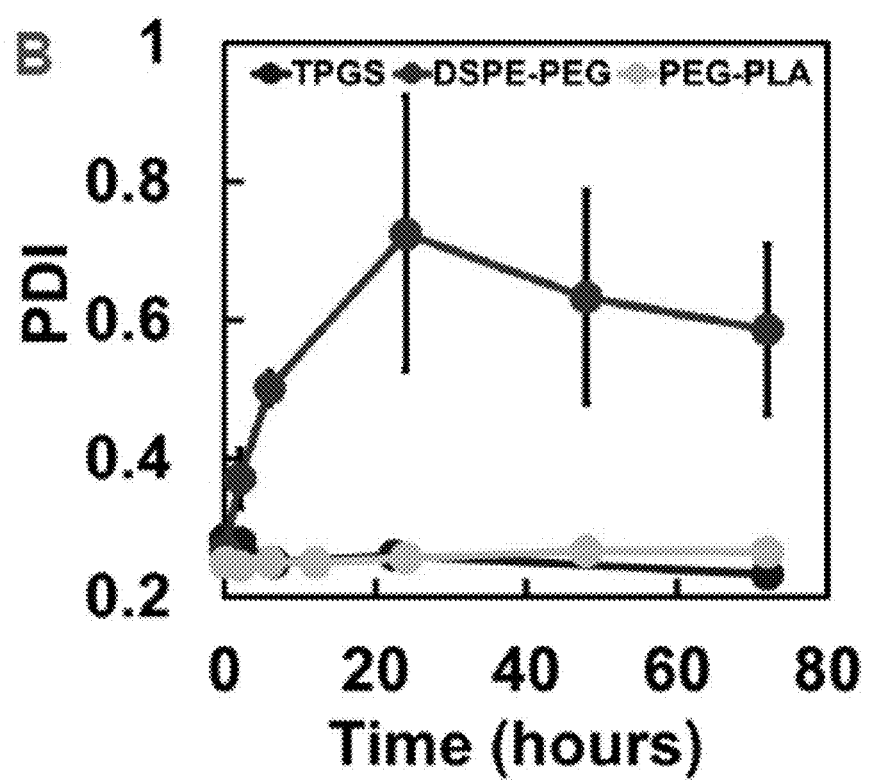

Various stabilizers influenced the nanoparticle complex stability. The stability of nanoparticle complexes was evaluated in the presence of 10% serum. PEG-PLA/Cu(DDC)$_2$ nanoparticle complexes showed excellent stability and did not have a significant change in particle size and PDI after incubation for at least 72 hours. Although there was no obvious precipitation in TPGS and DSPE-PEG Cu(DDC)$_2$ nanoparticle complex groups, particle sizes significantly increased over time (FIGS. 14A and 14B).

Figure 14C:
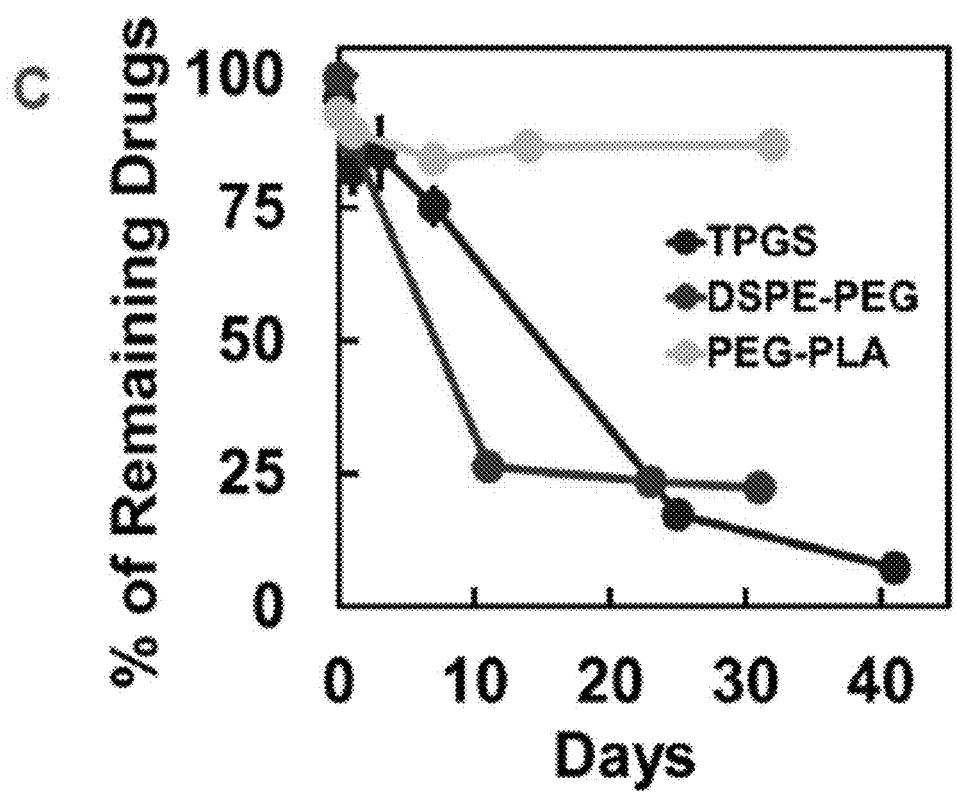

The long-term stability of Cu(DDC)$_2$ nanoparticle complexes prepared with various stabilizers, including TPGS, DSPE-PEG, and PEG-PLA, was also evaluated. Nanoparticle complexes were kept at room temperature and changes in drug concentration were determined. As shown in FIG. 14C, PEG-PLA/Cu(DDC)$_2$ nanoparticle complexes demonstrated excellent stability with a minor decrease of drug concentration after 30 days of storage at room temperature. In contrast, the drug concentrations of DSPE-PEG and TPGS nanoparticle complexes were significantly decreased, indicating reduced storage stability.

EXAMPLE 11

MTT Cytotoxicity Assay Evaluation Using Nanoparticle Complexes

In this example, Cu(DDC)$_2$ nanoparticle complexes were evaluated. MCF-7 breast cancer cells (ATCC) were cultured in a medium composed of Roswell Park Memorial Institute (RPMI) 1640 with 10% FBS and 1% Antibiotic-Antimycotic. MDA-MB-231 cells (ATCC) were cultured in a 1:1 mixture of Dulbecco's Modified Eagle's Medium (DMEM) and Ham's F-12 Medium, with 10% FBS and 1% Antibiotic-Antimycotic. DU145-TXR drug-resistant prostate cancer cells were obtained and cultured in a RPMI 1640 media supplemented with 10% FBS, 1% Antibiotic-Antimycotic, and 40 nM paclitaxel. Cells were cultured at 37° C. in a humidified atmosphere containing 5% CO$_2$.

Cells were seeded into a 96-well plate at a density of 5000 cells/well and incubated overnight. Then, a series of different concentrations of Cu(DDC)$_2$ nanoparticle complexes diluted in a cell culture medium was prepared and added to each well (100 µL/well). At different time points, cytotoxicity was determined with the 3-(4,5-dimethyl-thiazol-2-yl)-2, 5-diphenyl tetrazolium bromide (MTT) assay. The absorbance was determined with a microplate spectrophotometer at a wavelength of 570 nm and a reference wavelength of 670 nm. Cytotoxicity was calculated using the following equation:

Cell Viability (%)=$(A_{Test}/A_{control})\times 100\%$.

Furthermore, IC$_{50}$ was calculated with SigmaPlot software based on a dose-response curve.

Figure 15A:
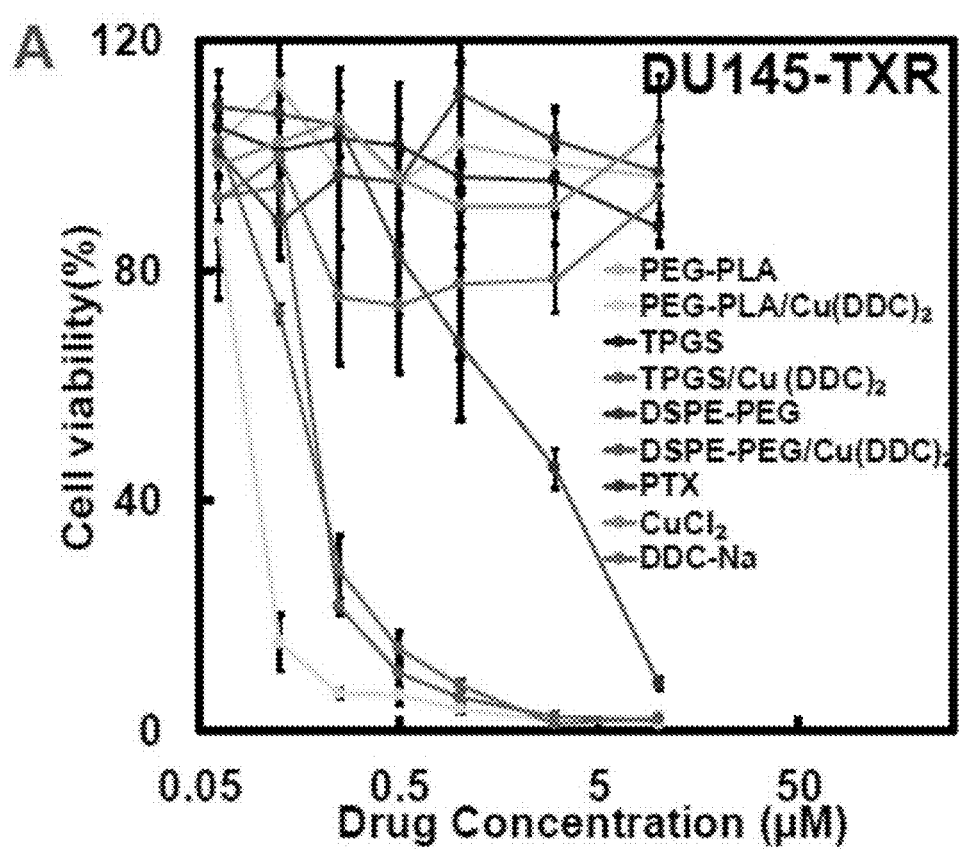
FIGS. 15A-15D show the results of a MTT assay. (A) DU145-TXR cells were treated with different formulations for 48 hours. DU145-TXR treated with DSPE-PEG/Cu (DDC)$_2$ nanoparticle complexes (B) and TPGS/$Cu(DDC)_2$ (C) for 24, 48, and 72 hours. (D) MDA-MB-231 cells treated with $Cu(DDC)_2$ nanoparticle complexes for 48 hours. Results are the mean±SD (n=4).

The anticancer activity of Cu(DDC)$_2$ nanoparticle complexes in drug-resistant DU145-TXR cells was determined using the MTT Assay. As shown in FIG. 15A, the DU145-TXR cell is resistant to paclitaxel with an IC$_{50}$ of 2575 nM. However, Cu(DDC)$_2$ nanoparticle complexes prepared with PEG-PLA, TPGS, and DSPE-PEG all showed potent anticancer activities after 48 hours of treatment. The IC$_{50}$ determinations for the various stabilizers were demonstrated to be 85 nM, 172 nM, and 193 nM, respectively. The treatment of equivalent concentrations of CuCl$_2$, DDC-Na, blank PEG-PLA, blank DSPE-PEG, or TPGS did not show significant cell toxicity.

Figure 15B:
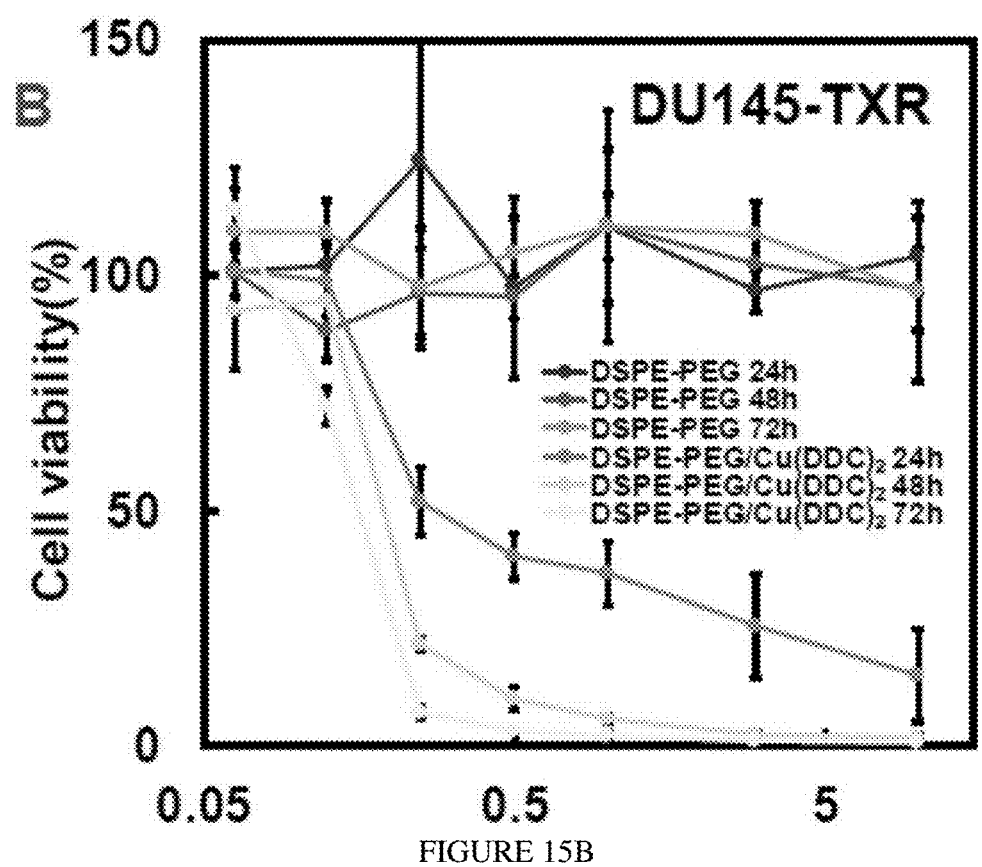
Figure 15C:
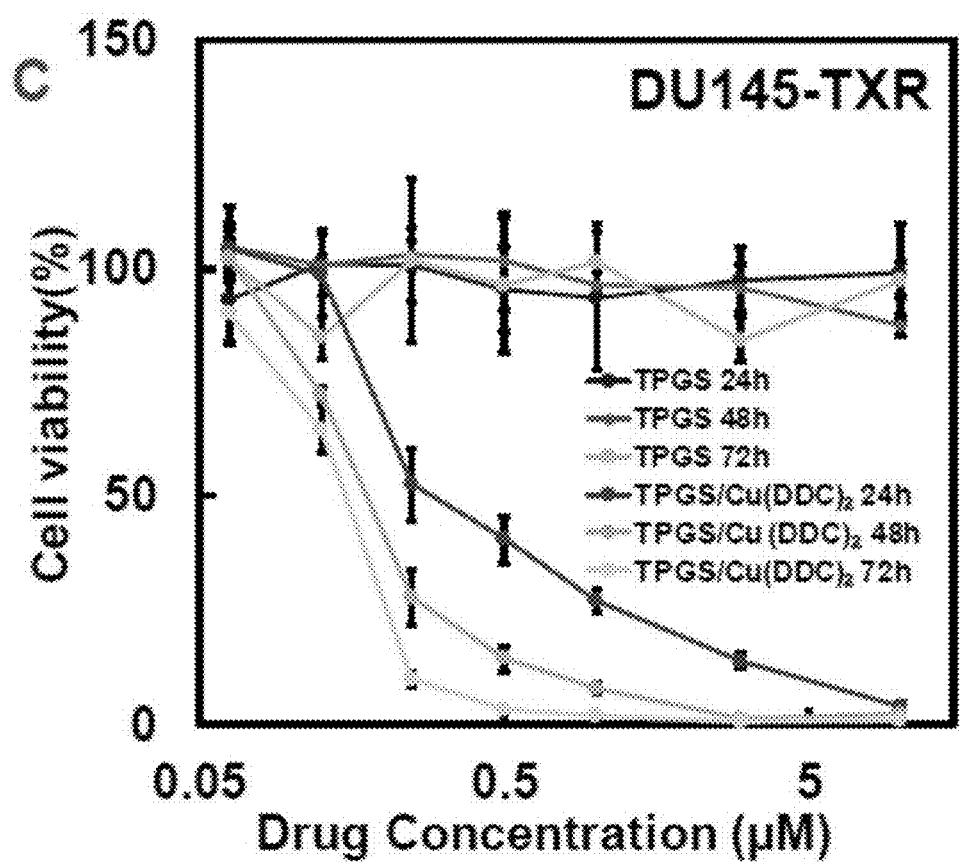
Figure 15D:
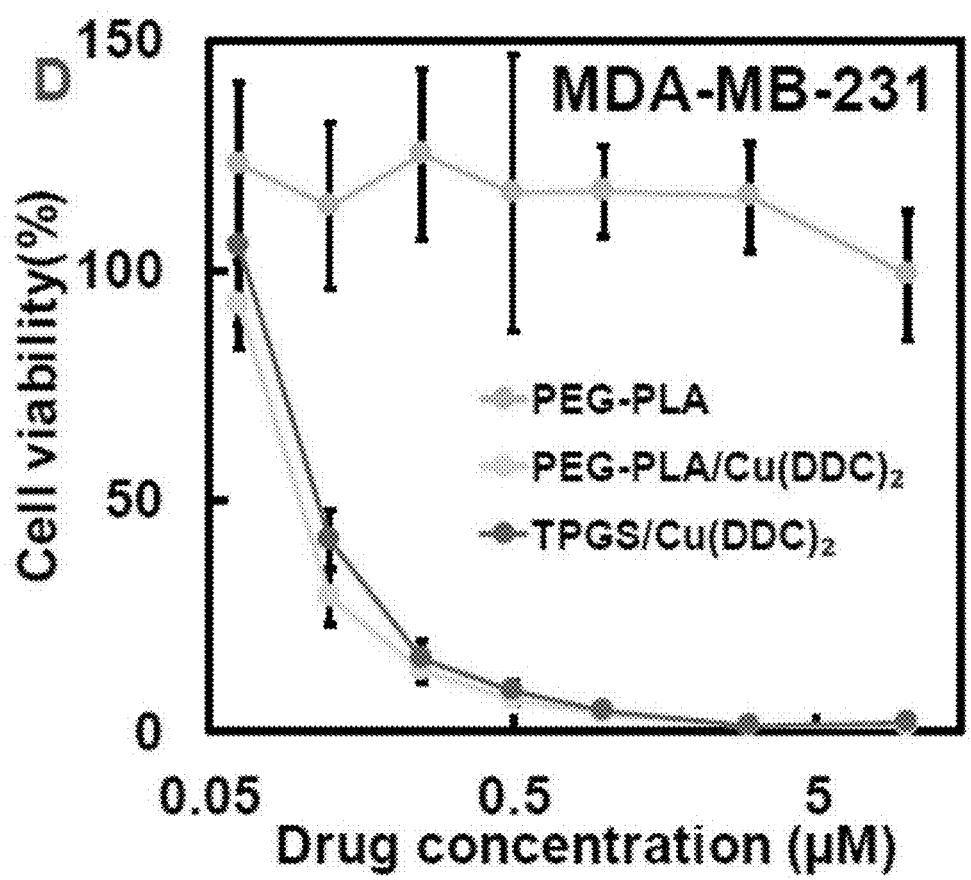

The anticancer effects also depended on the treatment time with increased anticancer effects occurring after prolonged treatment. Cells treated with DSPE-PEG/Cu(DDC)$_2$ nanoparticle complexes indicated an IC$_{50}$ of 216 nM at 24 hours and 138 nM at 72 hours (FIG. 15B). Similarly, cells treated with TPGS/Cu(DDC)$_2$ nanoparticle complexes showed an IC$_{50}$ of 280 nM at 24 hours and 149 nM at 72 hours (FIG. 15C). Cu(DDC)$_2$ nanoparticle complexes also demonstrated excellent anticancer activity in other cancer cells including MDA-MB-231 cells and MCF-7 cells. The IC$_{50}$ of TPGS/Cu(DDC)$_2$ nanoparticle complexes and PEG-PLA Cu(DDC)$_2$ nanoparticle complexes on MDA-MB-231 cells were 123 nM and 104 nM, respectively (FIG. 15D).

EXAMPLE 12

Colony-Forming Assay Evaluation Using Nanoparticle Complexes

In this example, the anticancer effects of Cu(DDC)$_2$ nanoparticle complexes were evaluated using a colony formation assay. Cells were seeded in a 24-well plate at a density of 500 cells per well and incubated overnight. Then, cells were treated with different formulations for 2 hours and further cultured in fresh cell culture medium for one week. Colonies were fixed with 100% methanol and stained with crystal violet.

Figure 16A:
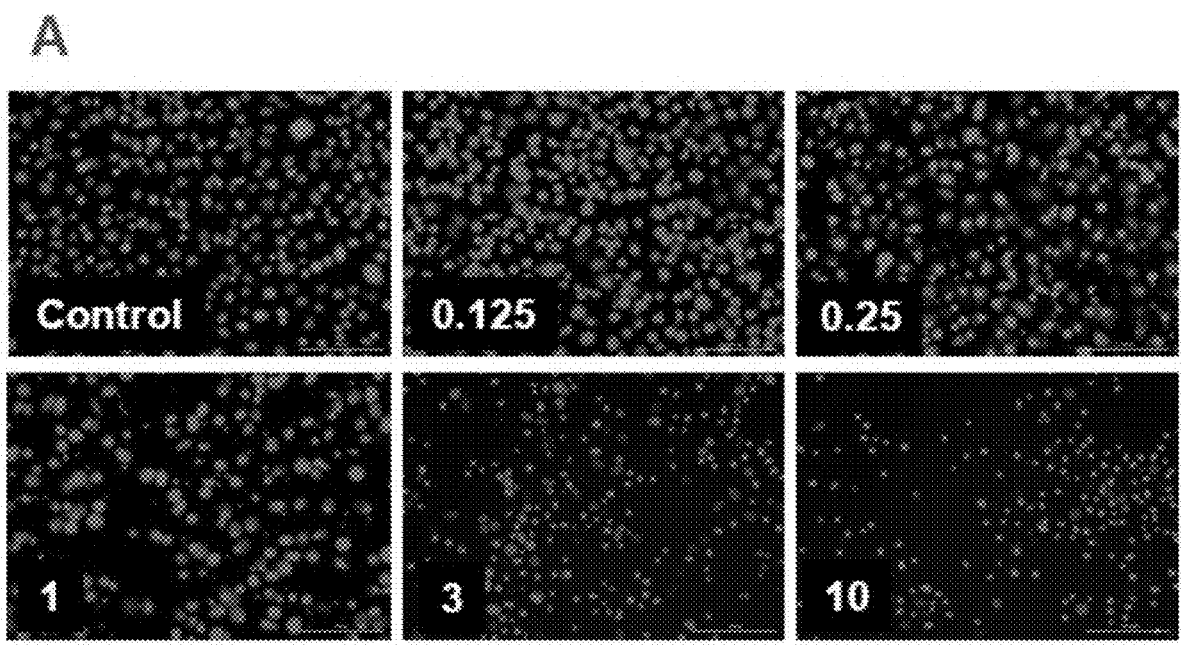
FIGS. 16A-16C show calcein-AM/PI staining. DU145-TXR cells in a 96-well plate were treated with various concentrations (μM) of TPGS/$Cu(DDC)_2$ nanoparticle complexes as well as a negative control (TPGS only). Twenty-four hours after treatment, cells were stained with Calcein-AM and PI, then analyzed by using fluorescence imaging (A) and by determining fluorescence intensity (B). Results are the mean±SD (n=4). (C) Cell colony assay. DU145-TXR cells were seeded at a density of 500 cells per well. The following day, cells were treated with 0.2 μM or 0.1 μM PEG-PLA/$Cu(DDC)_2$, and blank PEG-PLA for 2 hours. Cells were cultured for one additional week. Cell colonies were fixed with methanol and visualized with crystal violet staining.
Figure 16B:
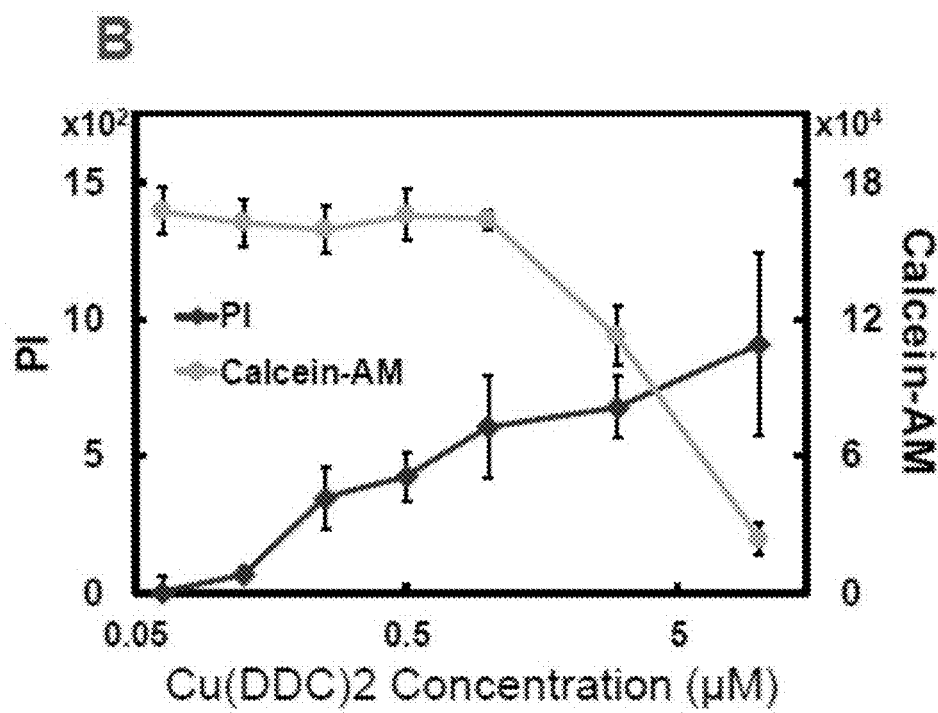
Figure 16C:
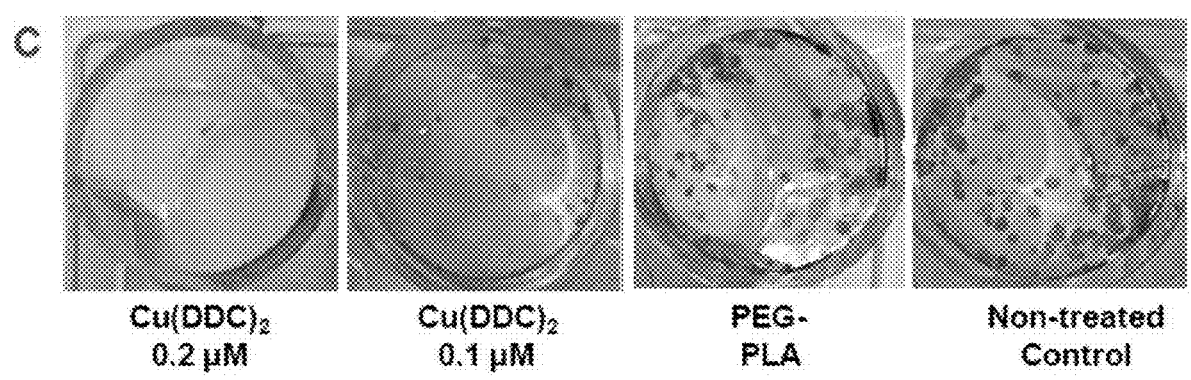

The treatment of blank PEG-PLA did not show any noticeable effects on colony formation by DU145-TXR cells. In contrast, treatment of PEG-PLA/Cu(DDC)$_2$ nanoparticle complexes showed significant inhibition of colony formation. The inhibition effects were significantly enhanced with the increased nanoparticle complex concentration. The colony formation was almost completely inhibited at Cu(DDC)$_2$ nanoparticle complex concentration of 0.2 µM (FIG. 16C).

EXAMPLE 13

Intracellular Reactive Oxygen Species (ROS) Evaluation Using Nanoparticle Complexes In this example, Cu(DDC)$_2$ nanoparticle complexes were evaluated. The generation of ROS was determined with a 2',7'-dichlorodihydrofluorescein diacetate (H2DCFDA) dye method. Briefly, cells were seeded in a dark-walled, clear-bottomed 96-well plate with 50,000 cells per well and incubated at 37° C. overnight before study. Cells were incubated with 20 µM H2DCFDA in Hank's Buffered Salt Solution (HBSS, pH=7.4) for 30 minutes at 37° C. in the dark, and treated with different formulations. Then, fluorescence was determined with a CYTATION 5 Imaging Reader at $EX_{485nm}/EM_{535nm}$.

Figure 18A:
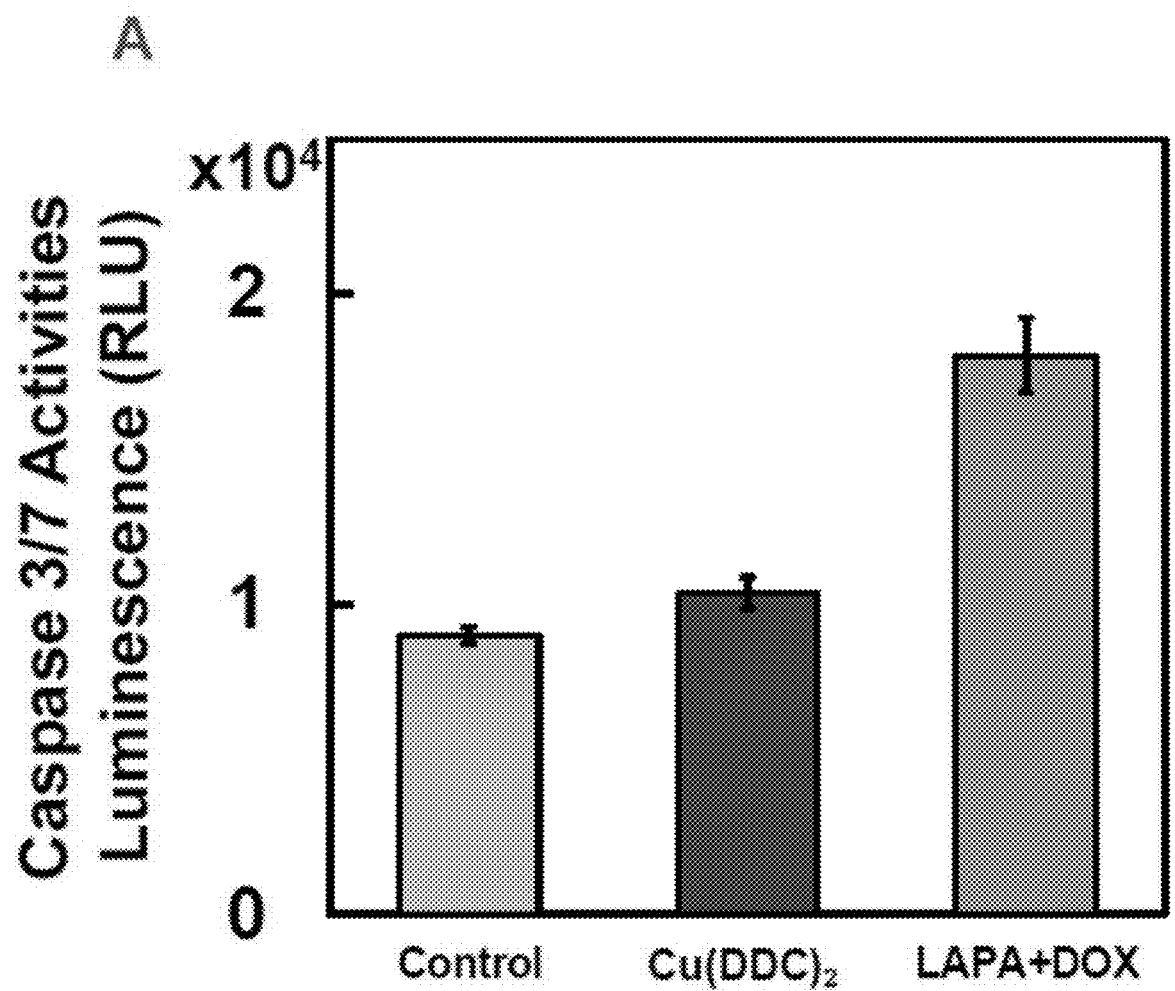
FIGS. 18A-18B show (A) the effects of $Cu(DDC)_2$ nanoparticle complex treatment on Caspase 3/7 activation. Cells were treated with blank PEG-PLA, $Cu(DDC)_2$ nanoparticle complexes (0.5 μM), and Lapatinib (10M)+Doxorubicin (20 μM) for 24 hours. Caspase 3/7 activities were determined with Caspase-Glo® 3/7 Assay. Results are the mean±SD (n=4). (B) The effects of $Cu(DDC)_2$ nanoparticle complex treatment on ROS generation. DU145-TXR cells were treated with 5.5 μM $Cu(DDC)_2$ nanoparticle complexes, 0.55 μM $Cu(DDC)_2$ nanoparticle complexes, 100 μM $H_2O_2$ (positive control), and PBS (negative control). ROS was determined with 2',7'-dichlorofluorescein diacetate method after treating cells with different formulations for different lengths of time. Results are the mean±SD (n=4).
Figure 18B:
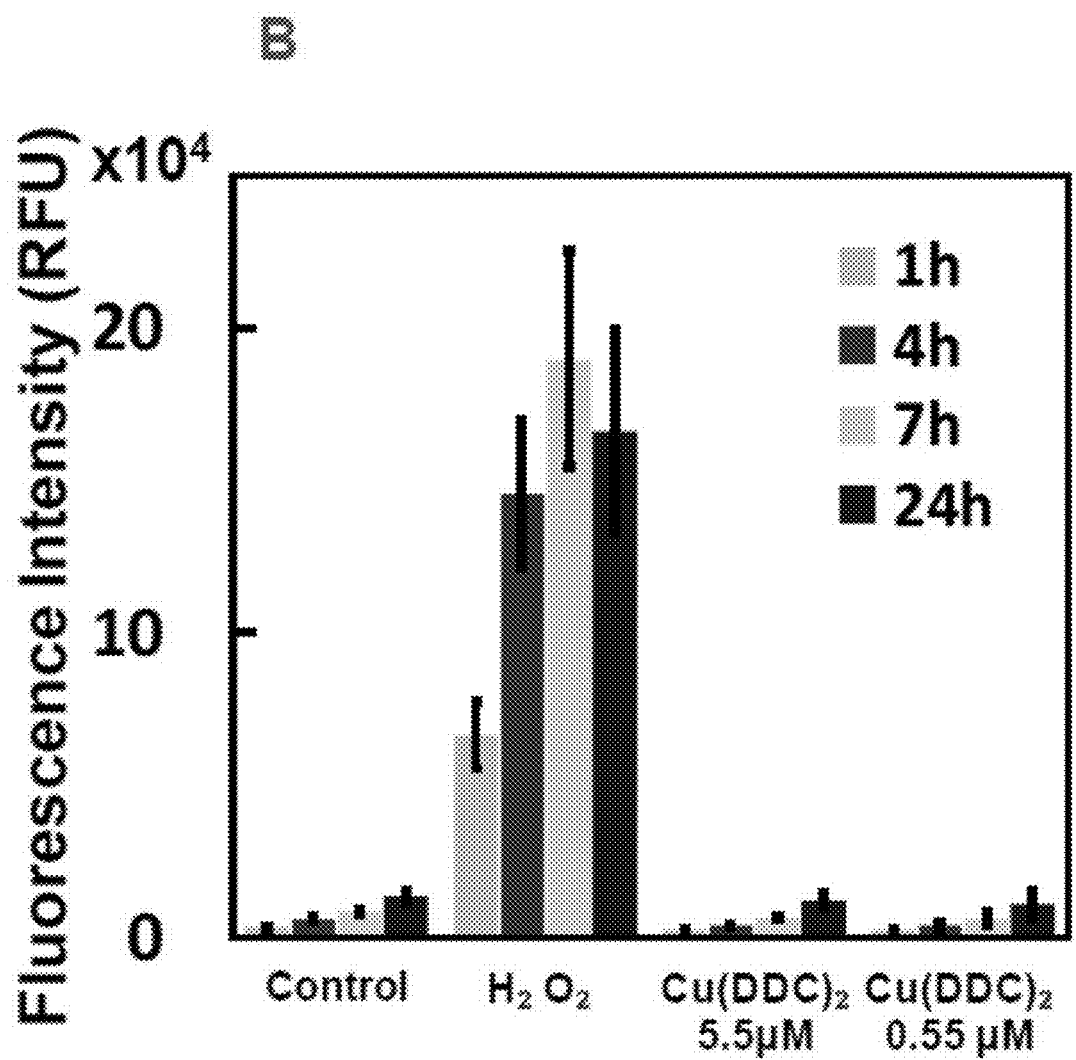
Figures 19A, 19B:
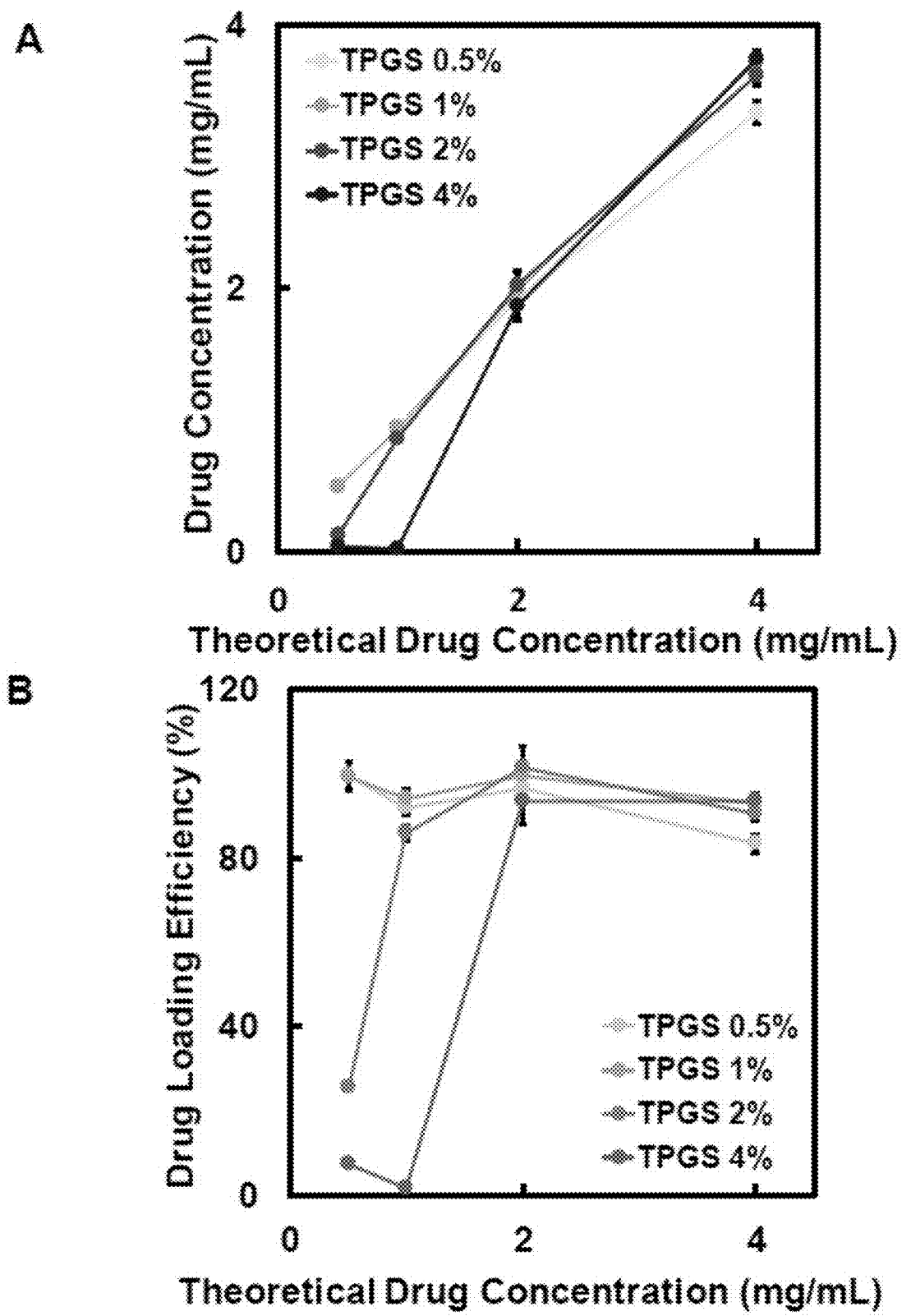
FIGS. 19A-19B show the effects of theoretical drug concentration and TPGS concentration on actual $Cu(DDC)_2$ drug concentration (A) and drug loading efficiency (B). Results are the mean±SD (n=3).
Figures 20A, 20B:
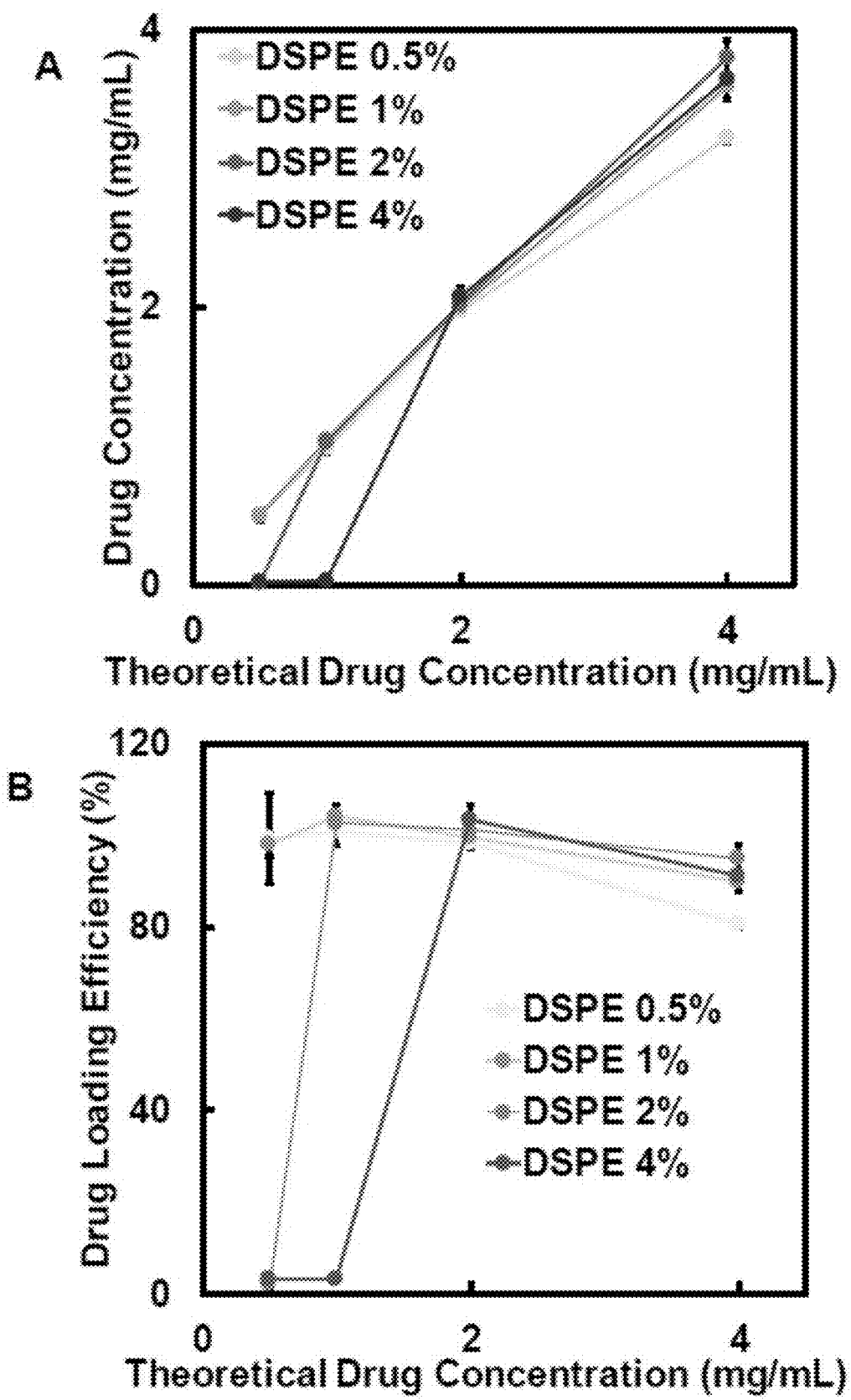
FIGS. 20A-20B show the effects of theoretical drug concentration and DSPE-PEG concentration on actual $Cu(DDC)_2$ drug concentration (A) and drug loading efficiency (B). Results are the mean±SD (n=3).

Induction of intracellular ROS was evaluated in DU145-TXR cells. As shown in FIG. 18B, the treatment of Cu(DDC)$_2$ nanoparticle complexes (5.5 µM or 0.55 µM) did not increase the ROS levels compared with the negative control HBSS-treated group, though the ROS level was increased in the H$_2$O$_2$ (100 µM) positive control treated group.

EXAMPLE 14

Live/Dead Staining with Calcein-AM/Propidium Iodide (PI)

In this example, cell viability based on Calcein AM and PI staining of cancer cells treated with Cu(DDC)$_2$ nanoparticle complexes was evaluated. Cells were seeded at a density of 5,000 cells per well in a 96-well plate. After overnight incubation, cells were treated with different formulations for 24 hours, then stained with a solution composed of Calcein-AM and PI in pH 7.4 phosphate-buffered saline (PBS). Cell samples were analyzed with the Cytation 5 Cell Imaging Multi-Mode Reader. Viable and dead cells can be identified by the green fluorescence (viable) and the red fluorescence (dead), respectively. The fluorescence intensities were determined quantitatively at $EX_{480nm}/EM_{530nm}$ (viable cells) and $EX_{530nm}/EM_{620nm}$ (dead cells).

Figure 25:
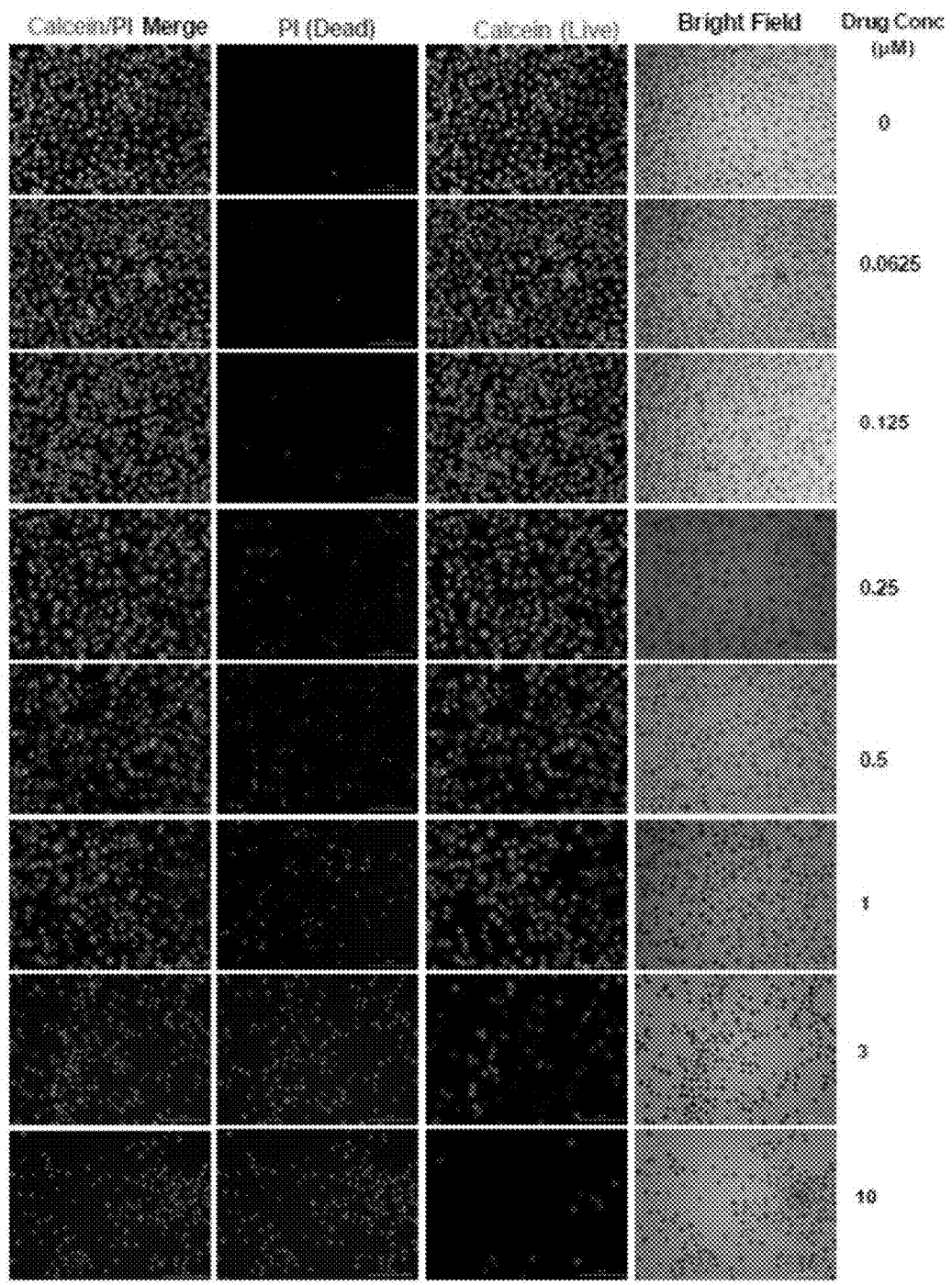
FIG. 25 shows calein AM/PI Staining of DU145-TXR cells treated with TPGS/Cu(DDC)$_2$ nanoparticle complexes.
Figures 26A, 26B, 26C, 26D:
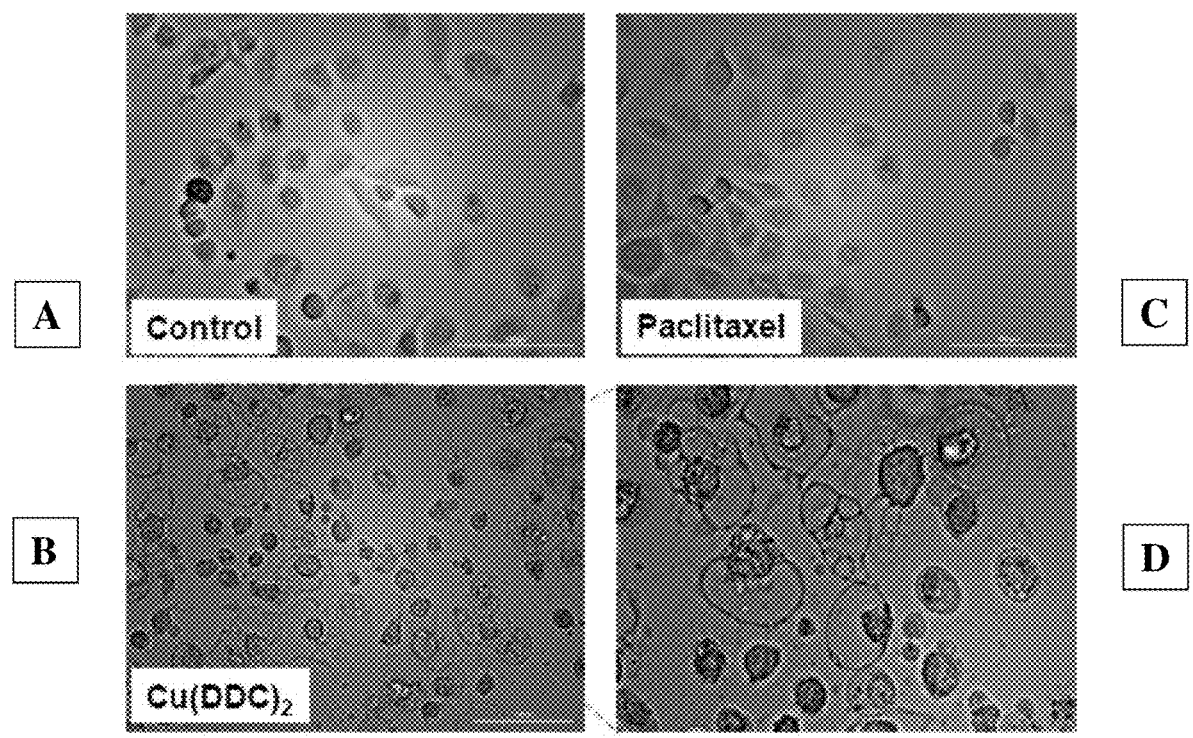
FIGS. 26A-26D show the morphology of DU145-TXR cells in (A) control, (B) treated with PEG-PLA/Cu(DDC)$_2$ nanoparticle complexes (0.5 µM), (C) treated with paclitaxel (0.5 µM), and (D) blank PEG-PLA for 24 hours.

The treatment with Cu(DDC)$_2$ nanoparticle complexes caused a dose-dependent increase in cell membrane permeability. The red staining of dead cells increased with increasing drug concentrations. Concurrently, the green florescence signal of living cells decreased with increasing drug concentrations. These were evaluated qualitatively with fluorescence imaging (FIG. 16A and FIG. 25) and quantitatively by determining green and red fluorescence intensities, respectively (FIG. 16B).

EXAMPLE 15

Caspase 3/7 Activity Evaluation Using Nanoparticle Complexes

Paraptosis is caspase-independent cell death. In this example, caspase 3/7 activities of DU145-RXR cells treated with Cu(DDC)$_2$ nanoparticle complexes were evaluated. Cells were seeded in a 96-well plate at a density of 20,000 cells per well and incubated overnight. After treating cells with different formulations, culture media was removed and 70 μl Caspase Glo 3 reagent (Promega, Madison, Wis.) was added to each well. After gently mixing the content in each well, the plate was incubated at room temperature for 30 minutes under dark conditions. Finally, 50 μl of the reaction solution was measured using a luminometer (CYTATION 5 Imaging Reader).

The treatment with Cu(DDC)$_2$ nanoparticle complexes (0.5 μM) did not cause significant increase of a caspase 3/7 activities compared to a negative control group of cells treated with an equivalent amount of PEG-PLA. However, the doxorubicin (20 μM) and lapatinib (10 μM) combination treated cells showed significant higher caspase 3/7 activity (FIG. 18A).

EXAMPLE 16

Cell Morphology Evaluation Using Nanoparticle Complexes

In this example, Cu(DDC)$_2$ nanoparticle complexes were evaluated. Cells seeded in a 96-well plate were treated with Cu(DDC)$_2$ nanoparticle complexes. Change of cell morphology induced by the nanoparticle complexes was observed with the Cytation 5 Cell Imaging Multi-Mode Reader. Cells were also co-treated with cycloheximide (CHX, a protein synthesis and paraptosis inhibitor) or chloroquine (CQ, an autophagy inhibitor) and observed their effects on Cu(DDC)$_2$ nanoparticle complex-induced cell morphology change.

Figures 27A, 27B, 27C:
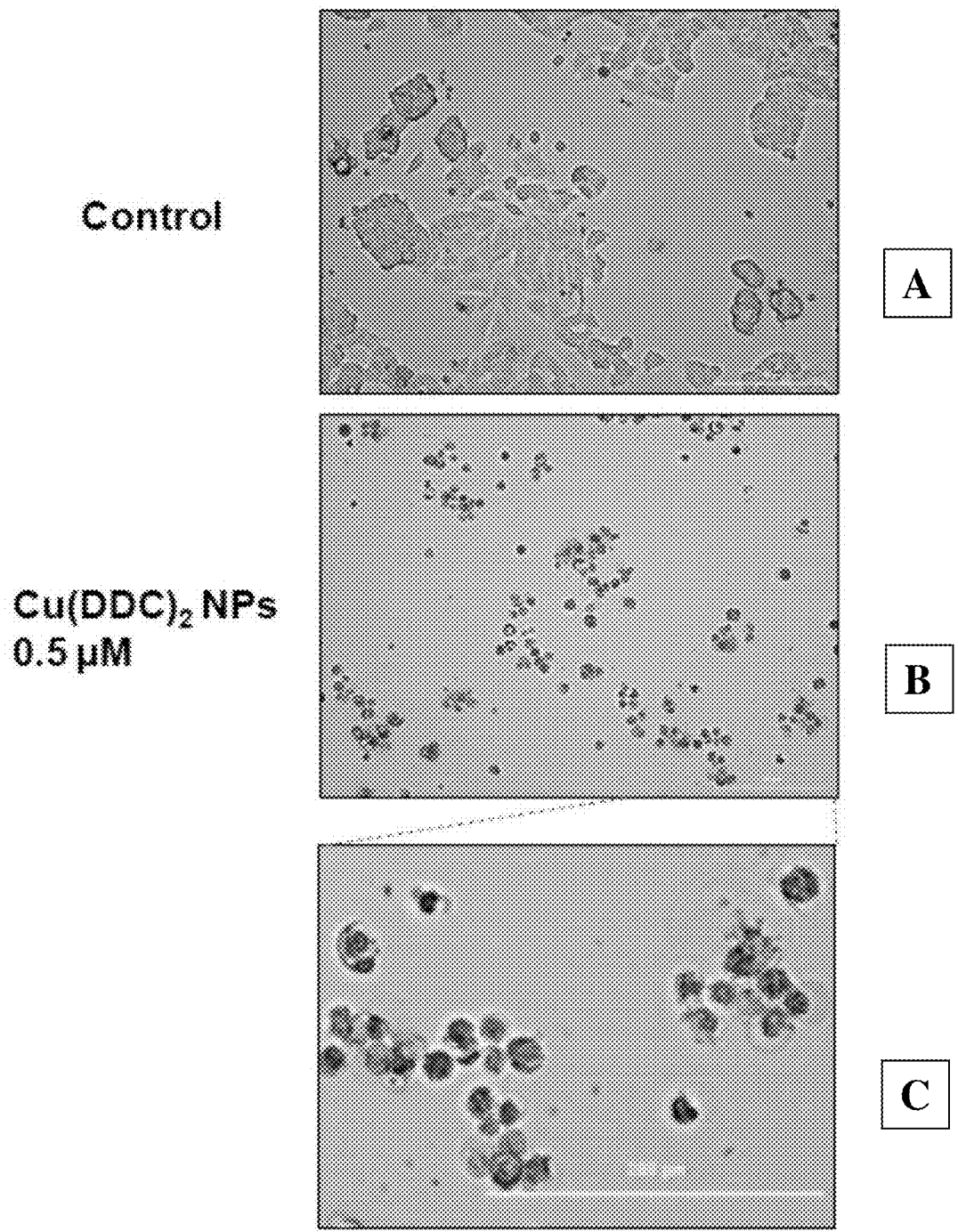
FIGS. 27A-27C show the morphology of MCF-7 Cells (A) control, (B) treated with 0.5 µM DSPE-PEG/Cu(DDC)$_2$ nanoparticle complexes for 72 hours, and (C) a magnification of panel B

Anticancer mechanisms of DSF and the DSF/copper combination have been previously investigated, and the proteasome/poly-Ub protein degradation pathway has been recognized as one of the major targets. The morphology of DU145-TXR cells was observed under bright field microscope. The Cu(DDC)$_2$ nanoparticle complexes included extensive cytoplasmic vacuolation in DU145-TXR cells (FIGS. 26A-26D). The vacuoles could be observed as early as 8 hours after the treatment and continuously increased in size. Cytoplasmic vacuolation was also observed in Cu(DDC)$_2$ nanoparticle complex-treated MCF-7 cells (FIGS. 27A-27C).

EXAMPLE 17

Endoplasmic Reticulum (ER) Staining Evaluation Using Nanoparticle Complexes

In this example, Cu(DDC)$_2$ nanoparticle complexes were evaluated. Cells were stained with ER specific dye and Hoechst 33342 prior to microscopy. Briefly, cells were seeded in a clear-bottomed, black-walled 96-well plate at a density of 20,000 cells per well. After treatment with different formulations for 8 hours, cells were incubated with a staining solution containing ER track dye (ER-ID green, Enzo Life Sciences Inc.) and Hoechst 33342 for 30 minutes at 37° C. avoiding light. Then, cells were washed with PBS and observed under a fluorescence microscope.

Figure 17A:
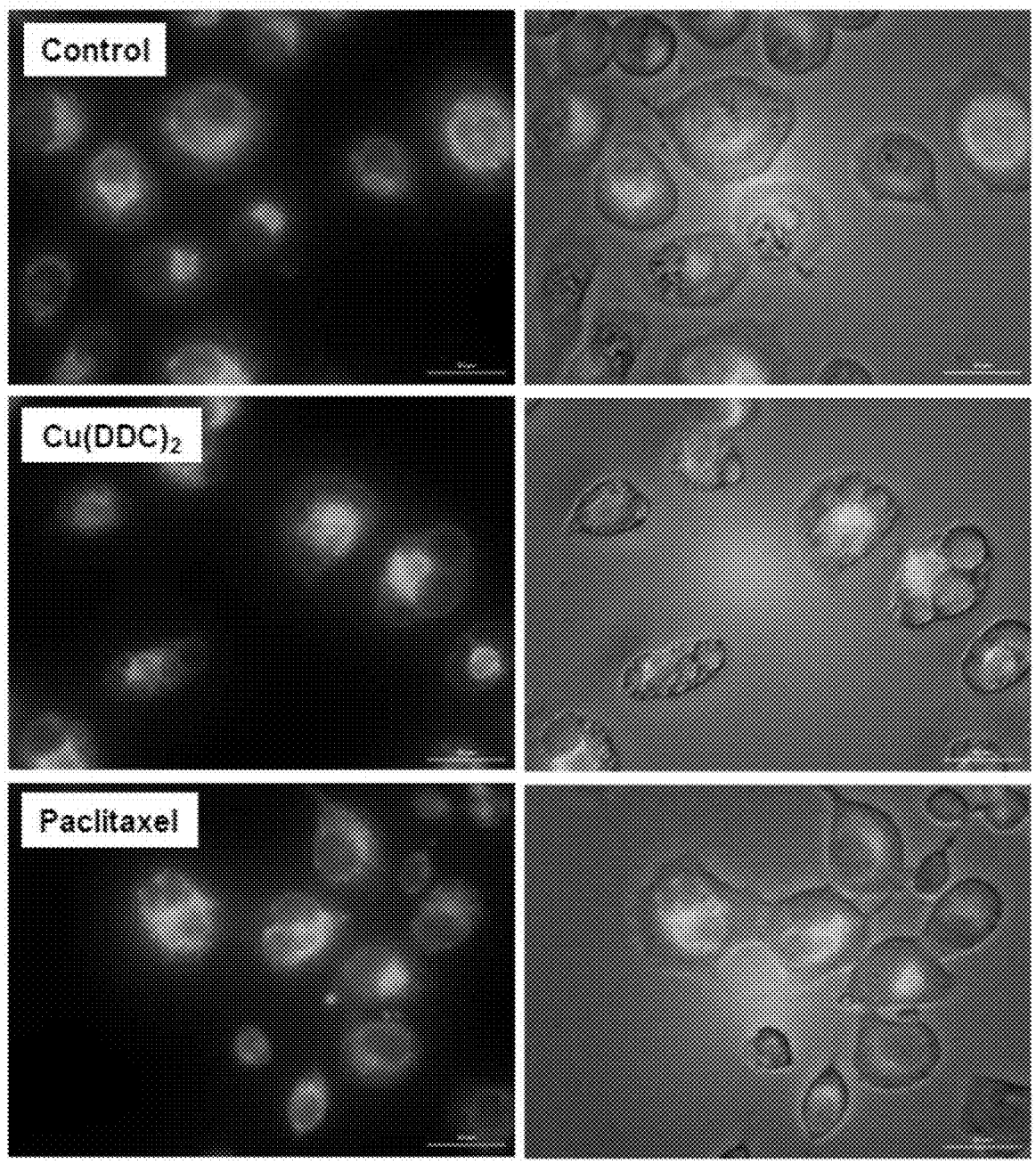
FIGS. 17A-17B show $Cu(DDC)_2$ nanoparticle complexes induced cell paraptosis. (A) DU145-TXR cells were treated with blank PEG-PLA, Paclitaxel (0.5 μM), or PEG-PLA/$Cu(DDC)_2$ nanoparticle complexes (0.5 μM) for 8 hours, stained with ER-ID green dye and Hoechst 33342. PEG-PLA/$Cu(DDC)_2$ nanoparticle complexes treatment induced cytoplasmic vacuolation resulted from dilated ER. (B) Morphology of Du145-TXR cells treated with $Cu(DDC)_2$ nanoparticle complexes (0.5 μM) alone and in combination with cycloheximide (CHX, 20 μM) or chloroquine (CQ 20 μM) for 8 hours.
Figure 17B:
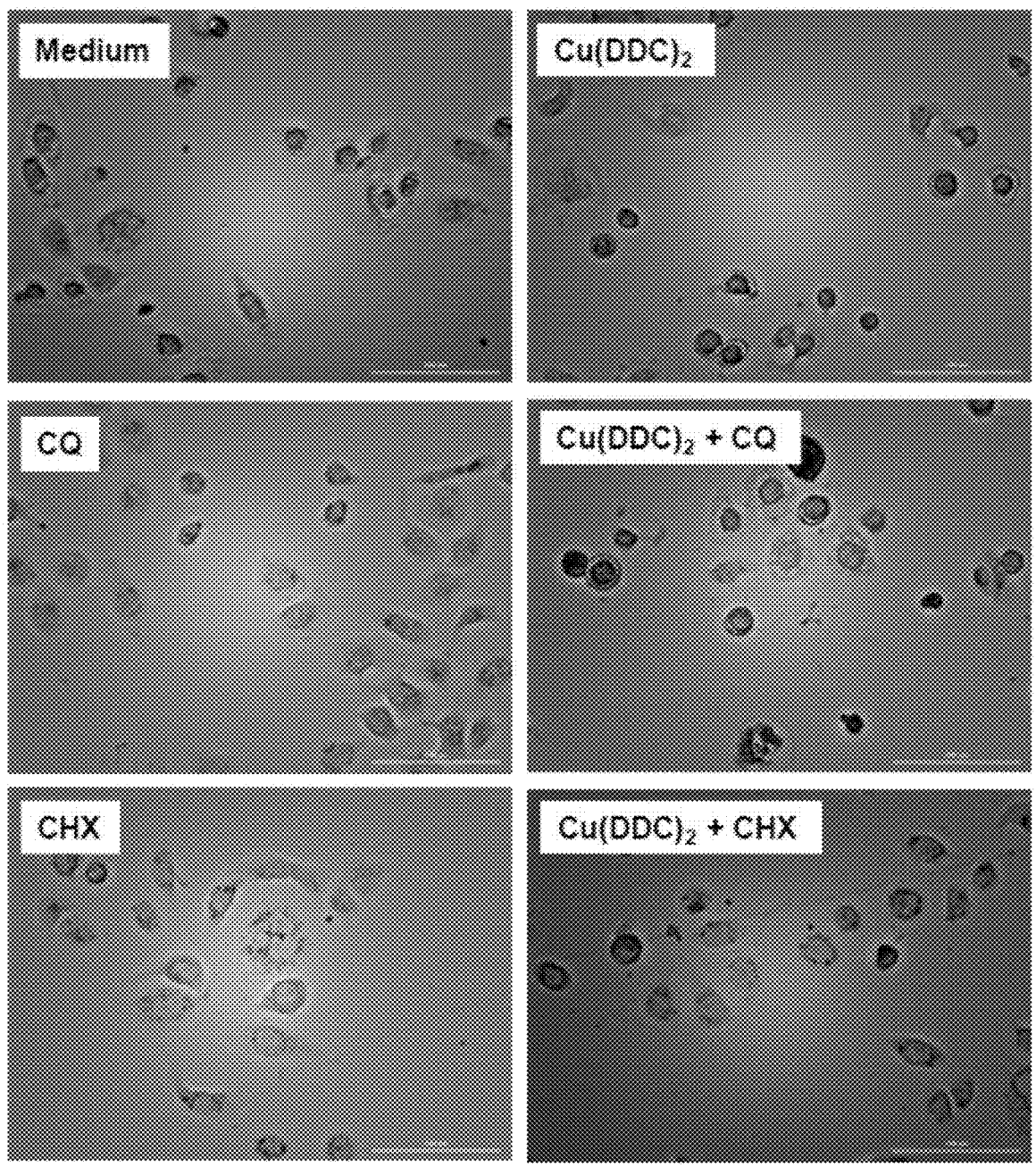
Figure 28:
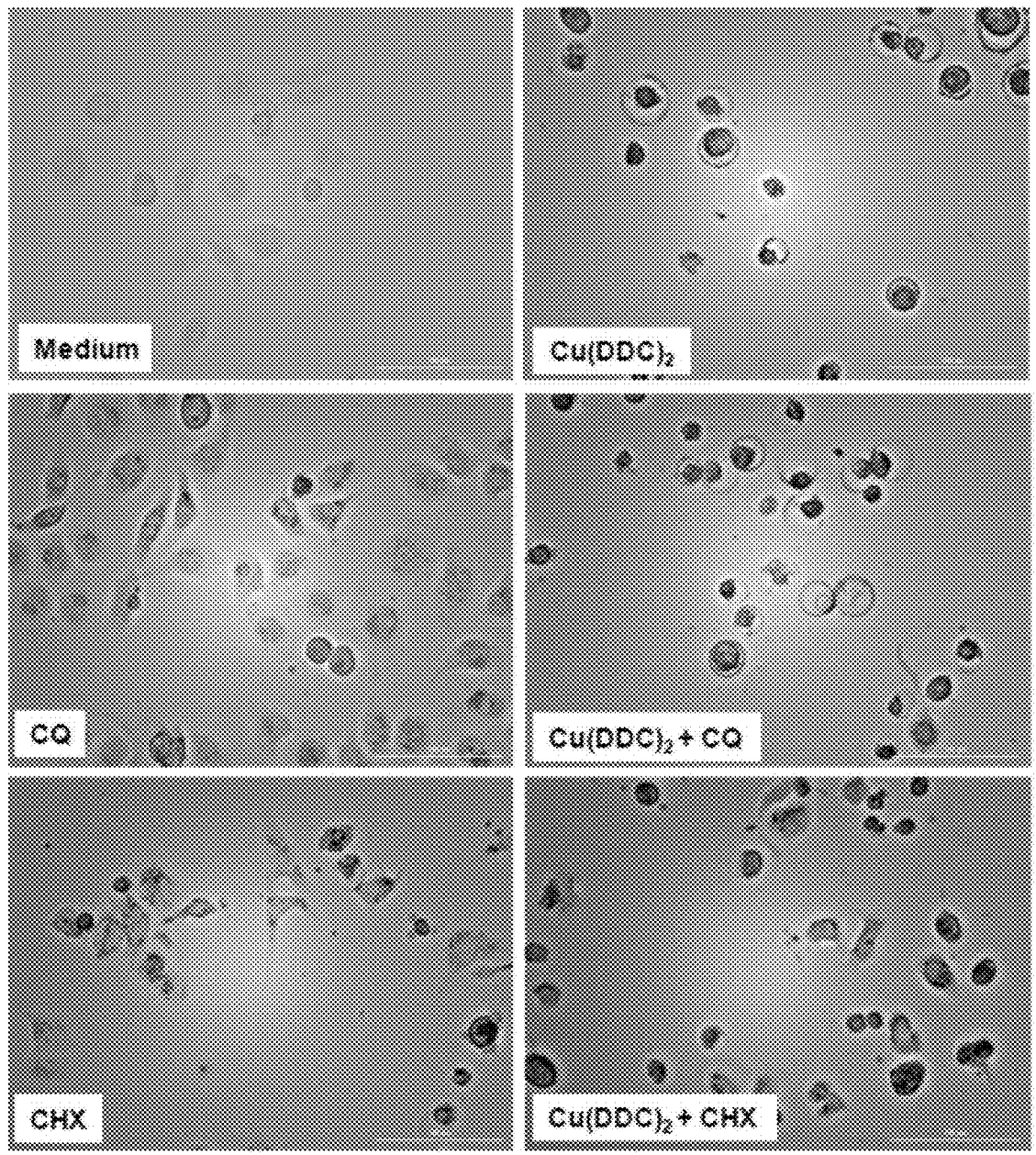
FIG. 28 shows Morphology of DU145-TXR cells treated with PEG-PLA/Cu(DDC)$_2$ nanoparticle complexes (0.5 µM) alone and in combination with cycloheximide (CHX, 20 µM) or chloroquine (CQ 20 µM) for 24 hours.

To examine the origin of the vacuoles, cells were stained with ER-Tracker dyes. As shown in FIG. 17A, ER in the control cells or cells treated with paclitaxel (0.5 μM) had a typical reticulate structure. The treatment of Cu(DDC)$_2$ nanoparticle complexes induced the formation of cytoplasmic vacuoles which were positive for ER-specific markers, indicating that they originated from the ER. The treatment of an autophagy inhibitor, chloroquine (CQ), did not show any significant effects on Cu(DDC)$_2$ nanoparticle complexes induced cytoplasmic vacuolation, indicating that cytoplasmic vacuolization was not caused by autophagosome accumulation (FIG. 17B). In contrast, cytoplasmic vacuolation was inhibited by the co-treatment with CHX, an inhibitor of paraptosis (FIG. 17B). The inhibition of cytoplasmic vacuolization was also observed after 24 hours of treatment (see FIG. 28).

EXAMPLE 18

Preparation of Cu— H3BTC Nanoparticle Complexes

In this example, Cu— H3BTC nanoparticle complexes were formed. First, approximately 46.7 mg of 1,3,5-benzenetricarboxylic acid (H3BTC) was dispersed into water containing 1% Pluronic F-127. Then, copper chloride (15 mg/mL) was slowly added in 1% Plutonic F-127 aqueous solution. After stirring for 24 hours, Cu— H3BTC nanoparticle were generated and collected by high speed centrifugation (10,000 rpm) for 10 minutes.

EXAMPLE 19

Preparation of Paclitaxel Cu(DDC)$_2$ Nanoparticle Complexes

Figure 29:
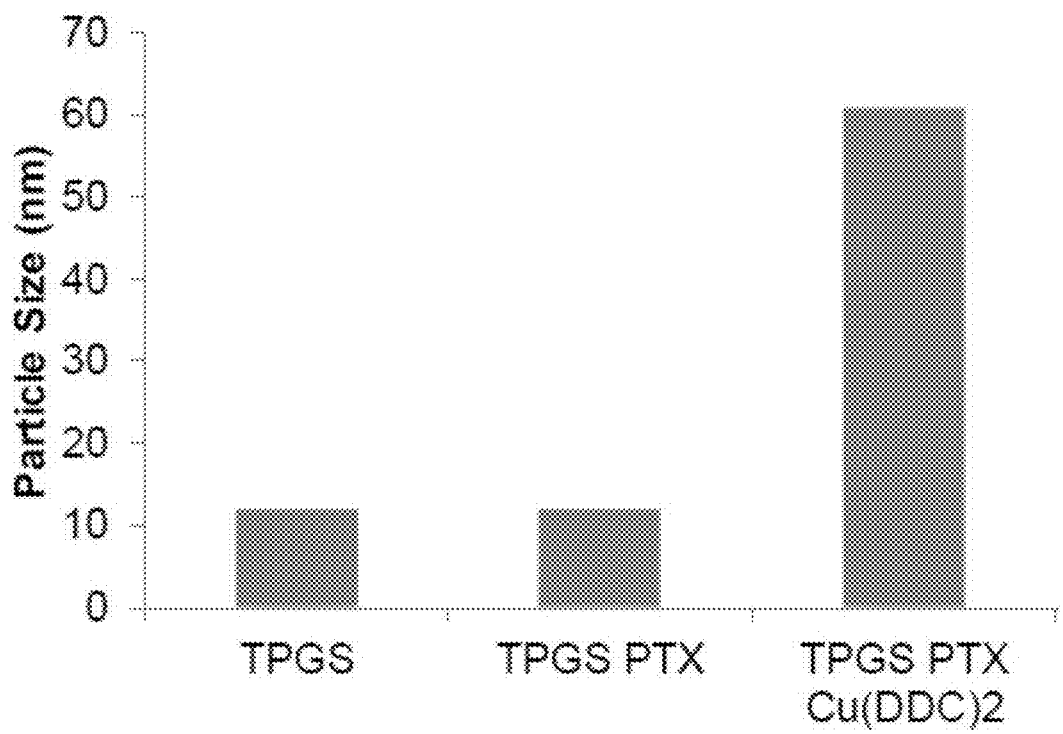
FIG. 29 shows the Particle size of Cu(DDC)$_2$ nanoparticle complexes using paclitaxel/TPGS as stabilizer. Paclitaxel/TPGS micelle was first prepared and then used as the stabilizer to prepare Cu(DDC)$_2$ nanoparticle complexes. These nanoparticle complexes can be utilized for combination therapy.

In this example, paclitaxel and Cu(DDC)$_2$ were used to form a nanoparticle complex comprising two therapeutic agents. D-α-Tocopherol polyethylene glycol 1000 succinate (TPGS, 11 mg) and paclitaxel (PTX, 1.1 mg) were dispersed in 1 mL of water to form nanoparticles. DDC-Na and $CuCl_2$ were dissolved as described in the TPGS/PTX nanoparticle to obtain a DDC-Na solution and a $CuCl_2$ solution, respectively. Thereafter, the DDC-Na solution and the $CuCl_2$ solution were mixed and vortexed for 1 minute to form $Cu(DDC)_2$ nanoparticle complexes. The resulting nanoparticle complex formulation was centrifuged at 10,000 rpm for 10 minutes and filtered with the 0.45 uM membrane to remove large aggregations (see FIG. 29).

EXAMPLE 20

Preparation of DiI dye $Cu(DDC)_2$ Nanoparticle Complexes

Figure 36A:
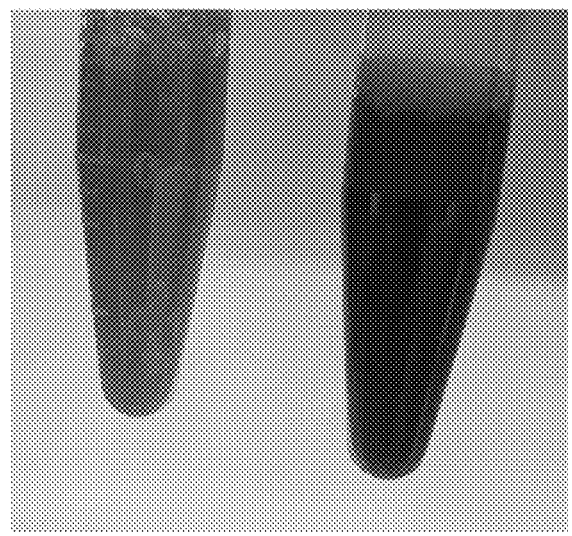
FIGS. 36A-36B show a TPGS Cu(DDC)2 nanoparticle complex labeled with DiI fluoresce dyes. (A) shows exemplary photos; (B) shows particle size.
Figure 36B:
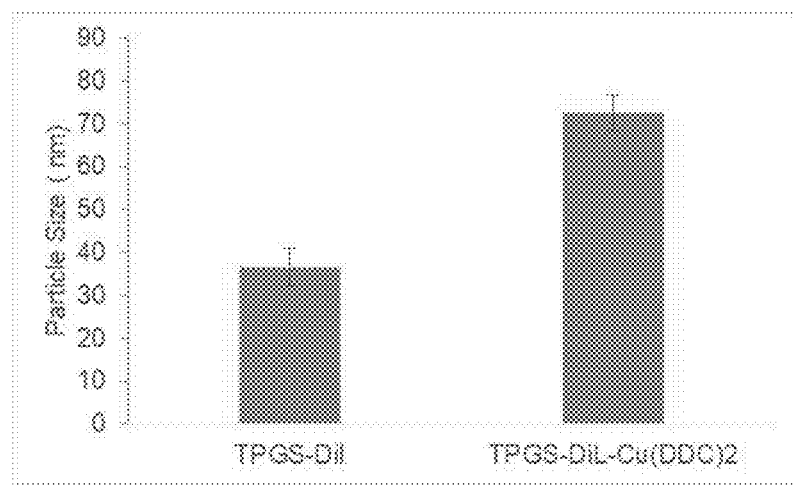

In this example, DiI dye and $Cu(DDC)_2$ were used to form a nanoparticle complex comprising a therapeutic agent and an imaging agent. D-α-Tocopherol polyethylene glycol 1000 succinate (TPGS, 11 mg) and 1,1'-Dioctadecyl-3,3,3',3'-tetramethylindocarbocyanine perchlorate (DiI, 1.1 mg) were dispersed in 1 mL of water to form nanoparticles. DDC-Na and $CuCl_2$ were dissolved as described in the TPGS/PTX nanoparticle to obtain a DDC-Na solution and a $CuCl_2$ solution, respectively. Thereafter, DDC-Na solution and $CuCl_2$ solution were mixed and vortexed for 1 minute to form $Cu(DDC)_2$ nanoparticle complexes. The resulting nanoparticle complex formulation was centrifuged at 10,000 rpm for 10 minutes and filtered with the 0.45 uM membrane to remove large aggregations. (see FIGS. 36A-36B).

EXAMPLE 21

Preparation of $Cu(PDTC)_2$ Nanoparticle Complexes

In this example, $Cu(PDTC)_2$ nanoparticle complexes were prepared by combining 1-pyrrolidinecarbodithioic acid ammonium salt (PDTC) and copper chloride aqueous ($CuCl_2$) solution containing 1% Pluronic F-127. The molar ratio between PDTC and $CuCl_2$ was 2:1. Briefly, PDTC and $CuCl_2$ were dissolved in 1% Pluronic F-127 to get a PDTC solution and a $CuCl_2$ solution, respectively. Then, PDTC solution and $CuCl_2$ solution were combined and vortexed for 1 minute to form $Cu(PDTC)_2$ nanoparticle complexes. The resulting nanoparticle complex formulation was centrifuged at 10,000 rpm for 10 minutes and filtered with the 0.45 uM membrane to remove large aggregations. (see FIGS. 30A-30B).

EXAMPLE 22

Preparation of $Cu(DMTC)_2$ Nanoparticle Complexes

In this example, $Cu(DMTC)_2$ nanoparticle complexes were prepared by combining sodium dimethyldithiocarbamate dihydrate (DMTC) and copper chloride aqueous ($CuCl_2$) solution containing 1% Pluronic F-127. The molar ratio between DMTC and $CuCl_2$ was 2:1. Briefly, DMTC and $CuCl_2$ were dissolved in 1% Pluronic F-127 to get a DMTC solution and a $CuCl_2$ solution, respectively. Then, DMTC solution and $CuCl_2$ solution were combined and vortexed for 1 minute to form $Cu(DMTC)_2$ nanoparticle complexes. The resulting nanoparticle complex formulation was centrifuged at 10,000 rpm for 10 minutes and filtered with the 0.45 uM membrane to remove large aggregations. (see FIGS. 30A-30B).

EXAMPLE 23

Preparation of Nanoparticle Complexes of DDC and other Metal Ions

Figure 31A:
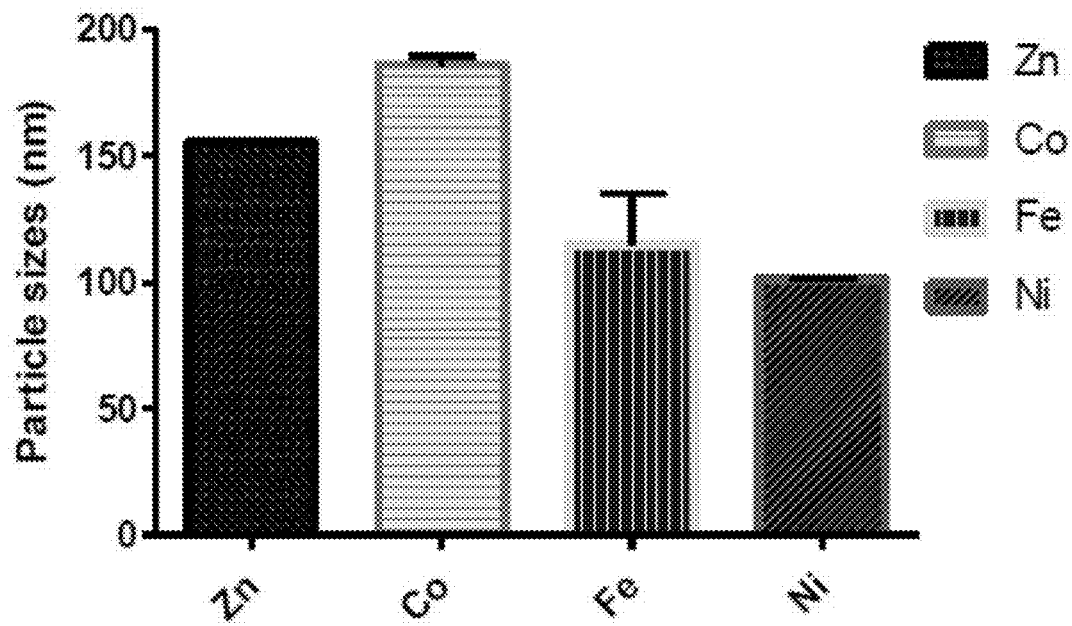
FIGS. 31A-31B show nanoparticle complexes prepared according to the disclosed methods using sodium diethyldithiocarbamatetrihydrate (DDC-Na) and various metal ions including Zinc Chloride ($Zn^{2+}$), Cobalt Chloride ($Co^{2+}$), Iron Chloride ($Fe^{2+}$), and Nickel Chloride ($Ni^{2+}$) with Pluronic® F-127 (1%) as a stabilizer. (A) shows particle size; (B) shows exemplary photos.
Figure 31B:
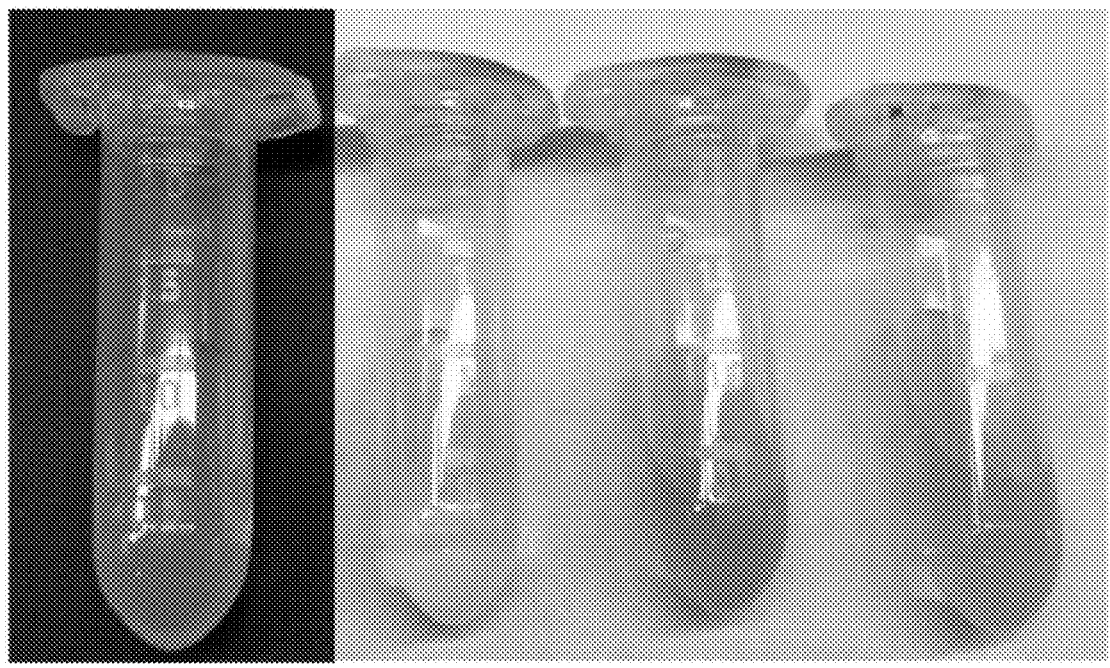
Figure 32:
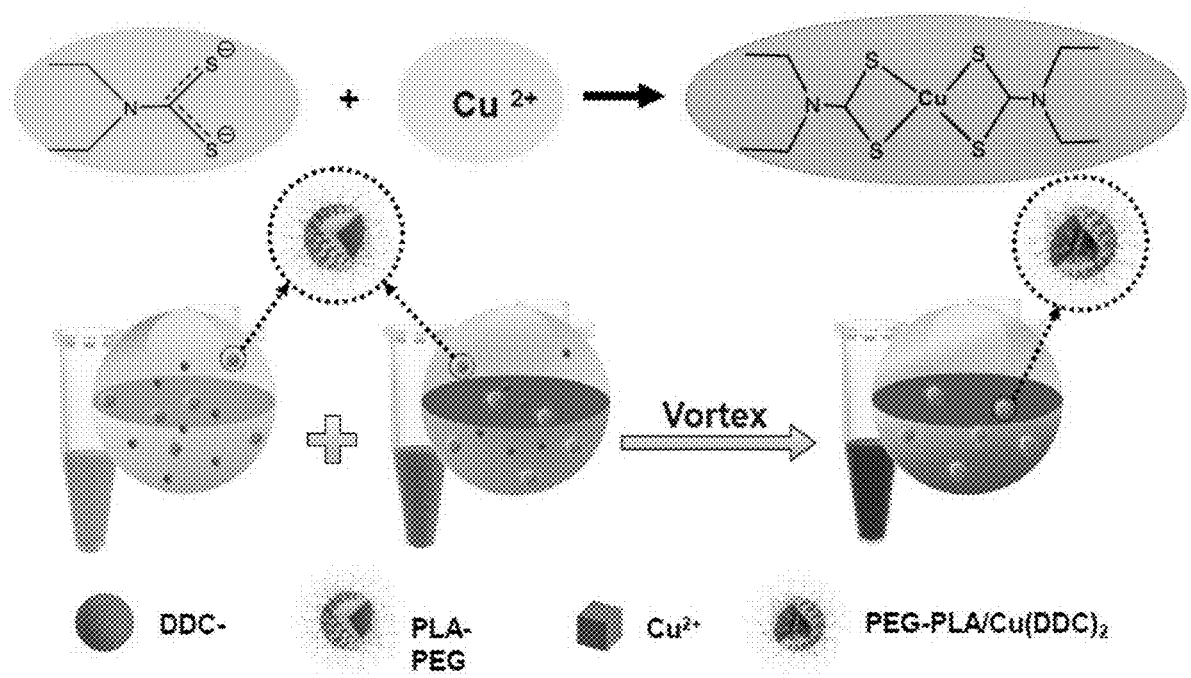
FIG. 32 shows preparation of Cu(DDC)$_2$ nanoparticle complexes with the disclosed vortex mixing methods.

In this example, nanoparticle complexes were prepared by combining DDC-Na with various metal ions including Zinc Chloride ($Zn^{2+}$), Cobalt Chloride ($Co^{2+}$), Iron Chloride ($Fe^{2+}$), and Nickel Chloride ($Ni^{2+}$) containing 1% Pluronic F-127. The molar ratio between DDC-Na and metal ions was 2:1. Briefly, DDC-Na and various metal ions were dissolved in 1% Pluronic F-127 to get a DDC-Na solution and various metal ions solution, respectively. Then, DDC-Na solution and various metal ions solution were combined and vortexed for 1 minute to form various nanoparticle complexes including $Zn(DDC)_2$, $Co(DDC)_2$, $Fe(DDC)_2$, and $Ni(DDC)_2$. The resulting nanoparticle complex formulation was centrifuged at 10,000 rpm for 10 minutes and filtered with the 0.45 uM membrane to remove large aggregations. (see FIGS. 31A-31B).

EXAMPLE 24

Preparation of $Cu(DDC)_2$ Nanoparticle Complexes Using a Microfluidics Mixer

Figure 33:
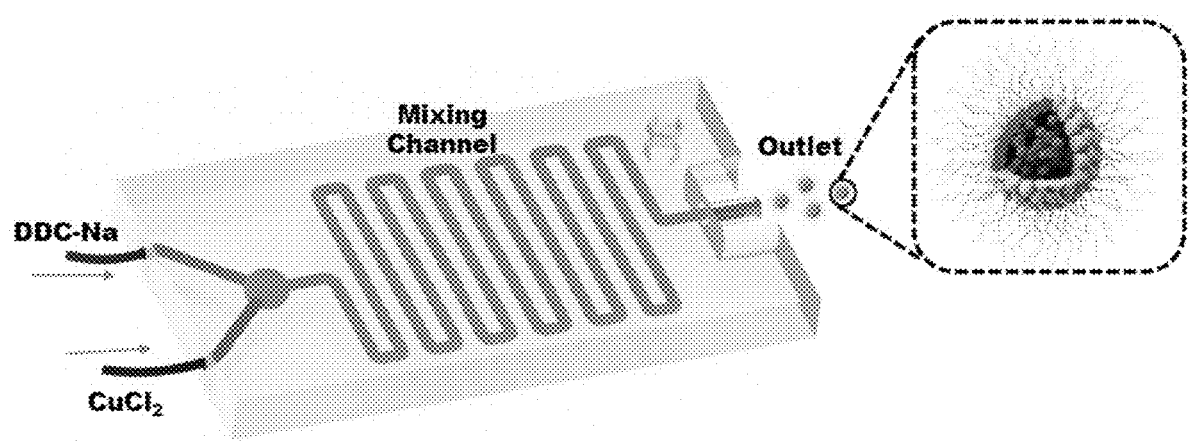
FIG. 33 shows preparation of Cu(DDC)$_2$ nanoparticle complexes with a microfluidics mixer.
Figures 34A, 34B:
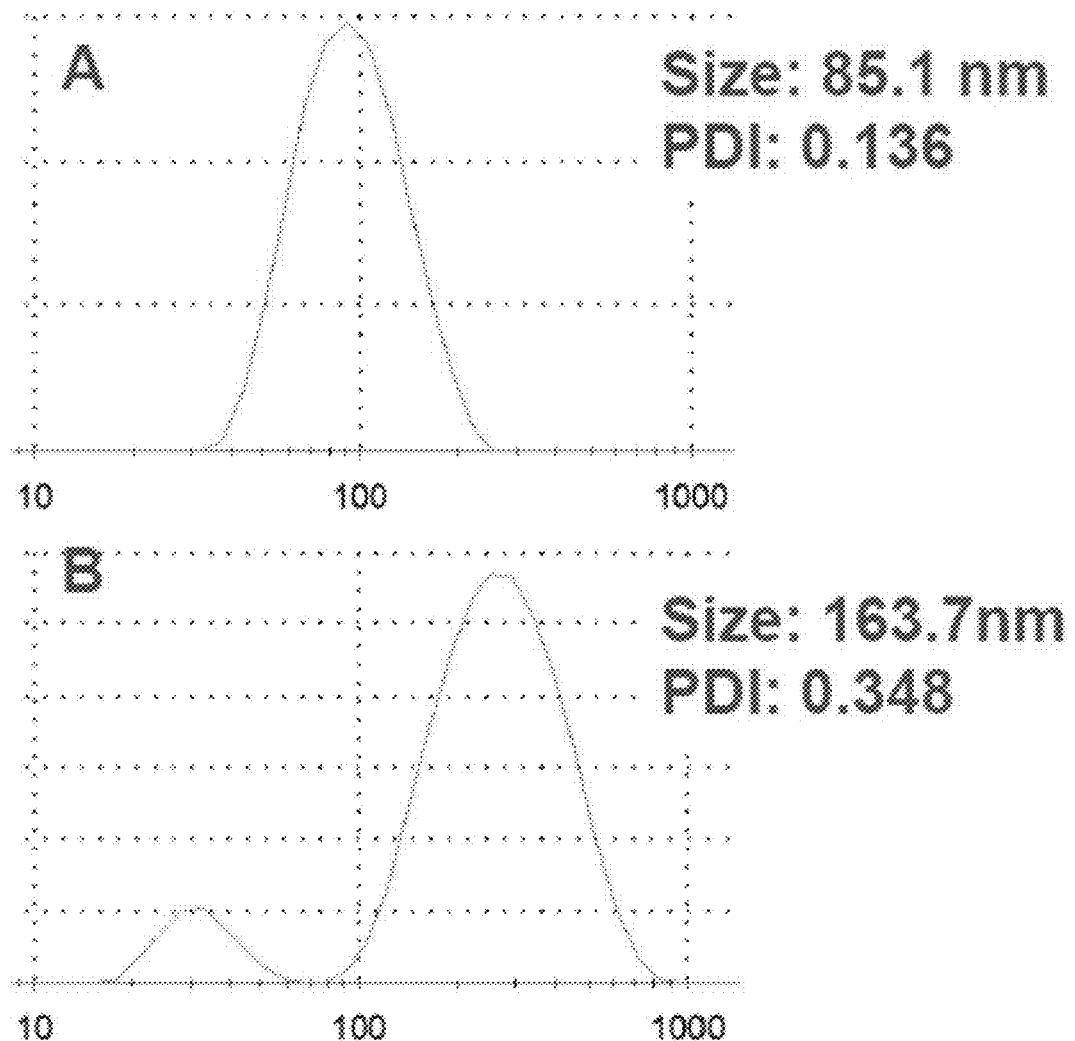
FIGS. 34A-34B shows particle size of Cu(DDC)$_2$ nanoparticle complexes prepared with microfluidics mixer (A) and vortex mixing (B). Cu(DDC)$_2$ nanoparticle complexes (1 mg/mL) was prepared with poloxamer 188 (10 mg/mL) as a stabilizer.
Figure 35:
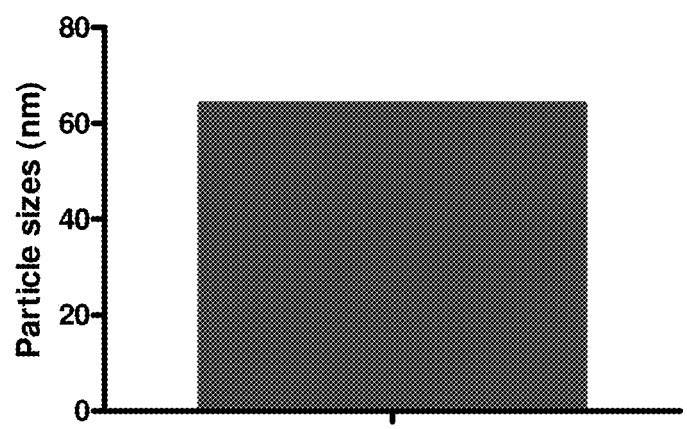
FIG. 35 shows particle size of Cu(DDC)$_2$ nanoparticle complexes prepared using chondroitin sulfate as a stabilizer.

In this example, $Cu(DDC)_2$ nanoparticle complexes were prepared by combining and mixing DDC-Na and copper chloride aqueous ($CuCl_2$) solution containing 1% Pluronic F-127 in a microfluidics mixer device. (see FIG. 33). The molar ratio between DDC-Na and $CuCl_2$ was 2:1. Briefly, DDC-Na and $CuCl_2$ were dissolved in 1% Pluronic F-127 to get a DDC-Na solution and a $CuCl_2$ solution, respectively. Then, DDC-Na solution and $CuCl_2$ solution were transferred into the mixing device with syringe pumps with a controlled flow rate (e.g. 1 ml/minute). DDC-Na solution and $CuCl_2$ solution were combined and mixed in the mixing channel of the device. The resulting nanoparticle complex formulation was collected from the outlet, centrifuged at 10,000 rpm for 10 minutes, and filtered with the 0.45 uM membrane to remove large aggregations. This microfluidics method could produce $Cu(DDC)_2$ nanoparticle complexes with a narrower distribution of particle size (smaller PDI number) compared with $Cu(DDC)_2$ nanoparticle complexes prepared with the vortex method when using 1% poloxamer 188 as the stabilizer. (see FIGS. 34A-34B).

EXAMPLE 25

Preparation of $Cu(DDC)_2$ Nanoparticle Complexes with Chondroitin Sulfate as a Stabilizer In this example, $Cu(DDC)_2$ nanoparticle complexes were prepared by combining DDC-Na and copper chloride aqueous ($CuCl_2$) solution containing 1% Chondroitin Sulfate. The molar ratio between DDC-Na and $CuCl_2$ was 2:1. Briefly, DDC-Na and $CuCl_2$ were dissolved in 1% Chondroitin Sulfate to get a DDC-Na solution and a $CuCl_2$ solution, respectively. Then, DDC-Na solution and $CuCl_2$ solution were combined and vortexed for 1 minute to form $Cu(DDC)_2$ nanoparticle complexes. The resulting nanoparticle complex formulation was centrifuged at 10,000 rpm for 10 minutes and filtered with the 0.45 uM membrane to remove large aggregations. (see FIG. 35).

EXAMPLE 26

Preparation of Cu(DDC)$_2$ Nanoparticle Complexes with Polyethylenimine (PEI) as a Stabilizer In this example, Cu(DDC)$_2$ nanoparticle complexes were prepared by combining DDC-Na and copper chloride aqueous (CuCl$_2$) solution containing 1% PEI (linear, MW 10,000). The molar ratio between DDC-Na and CuCl$_2$ was 2:1. Briefly, DDC-Na and CuCl$_2$ were dissolved in 1% PEI to get a DDC-Na solution and a CuCl$_2$ solution, respectively. Then, DDC-Na solution and CuCl$_2$ solution were combined and vortexed for 1 minute to form Cu(DDC)$_2$ nanoparticle complexes. The resulting nanoparticle complex formulation was centrifuged at 10,000 rpm for 10 minutes and filtered with the 0.45 uM membrane to remove large aggregations.

EXAMPLE 27

Preparation of Cu(DDC)$_2$ Nanoparticle Complexes with PEG2000-Paclitaxel Conjugate (PEG-PTX) as a Stabilizer In this example, Cu(DDC)$_2$ nanoparticle complexes were prepared by combining DDC-Na and copper chloride aqueous (CuCl$_2$) solution containing 1% PEG-PTX. PEG-PTX was synthesize by conjugate mPEG2000-COOH with paclitaxel through an ester bond. The molar ratio between DDC-Na and CuCl$_2$ was 2:1. Briefly, DDC-Na and CuCl$_2$ were dissolved in 1% PEG-PTX to get a DDC-Na solution and a CuCl$_2$ solution, respectively. Then, DDC-Na solution and CuCl$_2$ solution were combined and vortexed for 1 minute to form Cu(DDC)$_2$ nanoparticle complexes. The resulting nanoparticle complex formulation was centrifuged at 10,000 rpm for 10 minutes and filtered with the 0.45 uM membrane to remove large aggregations.

What is claimed is:

1. A method of making a nanoparticle complex, said method comprising the steps of:
   providing a first composition, wherein the first composition comprises at least one ligand;
   providing a second composition, wherein the second composition comprises a salt of the formula M$_n$X$_y$, wherein M is a metal cation and X is counterion, and wherein n is an integer from 1 to 3 and y is an integer from 1 to 5; and
   combining the first composition and the second composition to obtain the nanoparticle complex, wherein the nanoparticle complex comprises the ligand and M, wherein the step of combining the first composition and the second composition is performed using a mixing device, wherein the mixing device is a microfluidics mixer, and
   wherein the method further comprises a step of providing a third composition comprising one or more stabilizers, wherein the stabilizer is attached to the surface of the nanoparticle complex.

2. The method of claim 1, wherein the ligand is an organic molecule is capable of forming a complex with the metal cation, wherein the organic molecule comprises an atom or a functional group capable of donating an electron pair to the metal cation, and wherein the atom or the functional group is selected from the group consisting of S-donor, O-donor, N,O-donor, N-donor, P-donor, Lewis base, Shiff base, macrocycle, and N—N dimine donor.

3. The method of claim 1, wherein the ligand is a therapeutic agent, and wherein the therapeutic agent is diethyldithiocarbamatetrihydrate (DDC).

4. The method of claim 1, wherein the ligand is a therapeutic agent and wherein the therapeutic agent is selected from the group consisting of paclitaxel, docetaxel, and doxorubicin.

5. The method of claim 1, wherein the ligand is an imaging agent.

6. The method of claim 1, wherein M is selected from the group consisting of titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, and mercury.

7. The method of claim 1, wherein M is selected from the group consisting of Sc-44, Ti-46, V-48, Mn-52, Co-55, Cu-64, Ga-68, and Zr-89.

8. The method of claim 1, wherein the first or second or both compositions further comprise one or more stabilizers.

9. The method of claim 1, wherein the method further comprises a step of combining the third composition with the first composition and the second composition.

10. The method of claim 9, wherein the stabilizer is a hydrophilic material, and wherein the hydrophilic material is selected from the group consisting of Poly(N-isopropylacrylamide) (PNIPAM) and Polyacrylamide (PAM), Poly(-oxazoline) and Polyethylenimine (PEI), Poly(acrylic acid), Polymethacrylate and Other Acrylic Polymers, Poly(ethylene glycol) and Poly(ethylene oxide), Poly(vinyl alcohol) (PVA) and Copolymers, Poly(vinylpyrrolidone) (PVP) and Copolymers, Polyelectrolytes, hyaluronic acid, heparin, chondroitin sulfate, chitosan, polyglutamate, poly-lysine, poly-histidine, hydrophilic peptide, hydrophilic protein, nucleic acid, and poly-saccharide.

11. The method of claim 1, wherein the stabilizer is an amphiphilic composition and wherein the amphiphilic composition comprises a copolymer comprising an A-B type, an A-B-A type, or a B-A-B type.

12. The method of claim 11, wherein the amphiphilic composition is an amphiphilic peptide or an amphiphilic protein.

13. The method of claim 1, wherein the step of combining the first composition and the second composition is performed via vortexing.

14. The method of claim 1, wherein the combining of the first composition and the second composition is performed prior to the combination with the third composition.

15. The method of claim 1, wherein the combining of the first composition and the second composition is performed simultaneously with the combination with the third composition.

16. The method of claim 1 wherein dimethyl sulfoxide (DMSO) is not used for making the nanoparticle complex.

17. The method of claim 1, wherein the mixing device is a vortex device.

18. The method of claim 1, wherein the nanoparticle complex has a concentration of the ligand between about 1 mg/ml and about 5 mg/ml.

* * * * *